(12) United States Patent
Weiss et al.

(10) Patent No.: US 12,203,069 B2
(45) Date of Patent: Jan. 21, 2025

(54) ENGINEERED POST-POLY A SIGNAL RNA AND USES THEREOF

(71) Applicant: Massachusetts Institute of Technology, Cambridge, MA (US)

(72) Inventors: Ron Weiss, Newton, MA (US); James J. Collins, Newton, MA (US); Elvira Vitu, Brookline, MA (US); Casper Enghuus, Somerville, MA (US); Jeremy Jonathan Gam, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 791 days.

(21) Appl. No.: 16/875,257

(22) Filed: May 15, 2020

(65) Prior Publication Data
US 2020/0362345 A1 Nov. 19, 2020

Related U.S. Application Data

(60) Provisional application No. 62/849,424, filed on May 17, 2019.

(51) Int. Cl.
| | | |
|---|---|---|
| C07H 21/04 | (2006.01) | |
| C12N 5/071 | (2010.01) | |
| C12N 15/113 | (2010.01) | |
| C12N 15/90 | (2006.01) | |

(52) U.S. Cl.
CPC .......... *C12N 15/113* (2013.01); *C12N 5/0677* (2013.01); *C12N 15/907* (2013.01); *C12N 2310/141* (2013.01); *C12N 2310/20* (2017.05); *C12N 2506/03* (2013.01); *C12N 2800/80* (2013.01); *C12N 2830/50* (2013.01)

(58) Field of Classification Search
None
See application file for complete search history.

(56) References Cited

FOREIGN PATENT DOCUMENTS

| | | |
|---|---|---|
| WO | WO 2001/004313 A1 | 1/2001 |
| WO | WO 2019/028032 A1 | 2/2019 |

OTHER PUBLICATIONS

Banerjee et al., A novel tandem reporter quantifies RNA polymerase II termination in mammalian cells. PLoS One. Jul. 9, 2009;4(7):e6193.
Batista et al., Regulation of miR-200c/141 expression by intergenic DNA-looping and transcriptional read-through. Nat Commun. Jan. 4, 2016;7:8959.
Chadalavada et al., Wild-type is the optimal sequence of the HDV ribozyme under cotranscriptional conditions. RNA. Dec. 2007;13(12):2189-201. doi: 10.1261/rna.778107. Epub Oct. 23, 2007.
Chang et al., TAIL-seq: genome-wide determination of poly(A) tail length and 3' end modifications. Mol Cell. Mar. 20, 2014;53(6):1044-52. doi: 10.1016/j.molcel.2014.02.007. Epub Feb. 27, 2014.
Chylinski et al., The tracrRNA and Cas9 families of type II CRISPR-Cas immunity systems. RNA Biol. May 2013;10(5):726-37.
Deng et al., Useful Bicistronic Reporter System for Studying Poly(A) Site-Defining cis Elements and Regulation of Alternative Polyadenylation. Int J Mol Sci. Jan. 17, 2018;19(1):279.
Donello et al., Woodchuck hepatitis virus contains a tripartite posttranscriptional regulatory element. J Virol. Jun. 1998;72(6):5085-92.
Dower et al., A synthetic A tail rescues yeast nuclear accumulation of a ribozyme-terminated transcript. RNA. Dec. 2004;10(12):1888-99.
Fellmann et al., An optimized microRNA backbone for effective single-copy RNAi. Cell Rep. Dec. 26, 2013;5(6):1704-13. doi: 10.1016/j.celrep.2013.11.020. Epub Dec. 12, 2013.
Ferretti et al., Complete genome sequence of an M1 strain of *Streptococcus pyogenes*. Proc Natl Acad Sci U S A. Apr. 10, 2001;98(8):4658-63.
Guo et al., Poly(A) signals located near the 5' end of genes are silenced by a general mechanism that prevents premature 3'-end processing. Mol Cell Biol. Feb. 2011;31(4):639-51.
Ismail et al., Use of intron-disrupted polyadenylation sites to enhance expression and safety of retroviral vectors. J Virol. Jan. 2001;75(1):199-204.
Jinek et al., A programmable dual-RNA-guided DNA endonuclease in adaptive bacterial immunity. Science. Aug. 17, 2012;337(6096):816-21.
Kempf et al., Poliovirus 2A(Pro) increases viral mRNA and polysome stability coordinately in time with cleavage of eIF4G. J Virol. Jun. 2008;82(12):5847-59. doi: 10.1128/JVI.01514-07. Epub Apr. 9, 2008.
Muniz et al., Poly(A) Polymerase and the Nuclear Poly(A) Binding Protein, PABPN1, Coordinate the Splicing and Degradation of a Subset of Human Pre-mRNAs. Mol Cell Biol. Jul. 2015;35(13):2218-30. doi: 10.1128/MCB.00123-15. Epub Apr. 20, 2015.
Nissim et al., Multiplexed and programmable regulation of gene networks with an integrated RNA and CRISPR/Cas toolkit in human cells. Mol Cell. May 22, 2014;54(4):698-710. doi: 10.1016/j.molcel.2014.04.022. Epub May 15, 2014.
Qi et al., Repurposing CRISPR as an RNA-guided platform for sequence-specific control of gene expression. Cell. Feb. 28, 2013;152(5):1173-83.
Terhune et al., Early polyadenylation signals of human papillomavirus type 31 negatively regulate capsid gene expression. J Virol. Sep. 2001;75(17):8147-57.
Tian et al., Independent and high-level dual-gene expression in adult stem-progenitor cells from a single lentiviral vector. Gene Ther. Jul. 2009;16(7):874-84.

(Continued)

*Primary Examiner* — Kimberly Chong
(74) *Attorney, Agent, or Firm* — Wolf, Greenfield & Sacks, P.C.

(57) ABSTRACT

The present disclosure is related to an engineered nucleic acid encoding a post-poly A signal RNA 3' to a terminator for expression of protein, and/or non-coding RNA. Also provided herein are methods for reducing epigenetic silencing, genetic modification, transcriptional regulation of the engineered nucleic acid described herein.

17 Claims, 54 Drawing Sheets
Specification includes a Sequence Listing.

(56) References Cited

OTHER PUBLICATIONS

Visa et al., A nuclear cap-binding complex binds Balbiani ring pre-mRNA cotranscriptionally and accompanies the ribonucleoprotein particle during nuclear export. J Cell Biol. Apr. 1996;133(1):5-14.

Zhao et al., Formation of mRNA 3' ends in eukaryotes: mechanism, regulation, and interrelationships with other steps in mRNA synthesis. Microbiol Mol Biol Rev. Jun. 1999;63(2):405-45.

Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.

Deltcheva et al., CRISPR RNA maturation by trans-encoded small RNA and host factor RNase III. Nature. Mar. 31, 2011;471(7340):602-7.

Sarkar, Polyadenylation of mRNA in prokaryotes. Annu Rev Biochem. 1997;66:173-97.

Wickens et al., Role of the conserved AAUAAA sequence: four AAUAAA point mutants prevent messenger RNA 3' end formation. Science. Nov. 30, 1984;226(4678):1045-51.

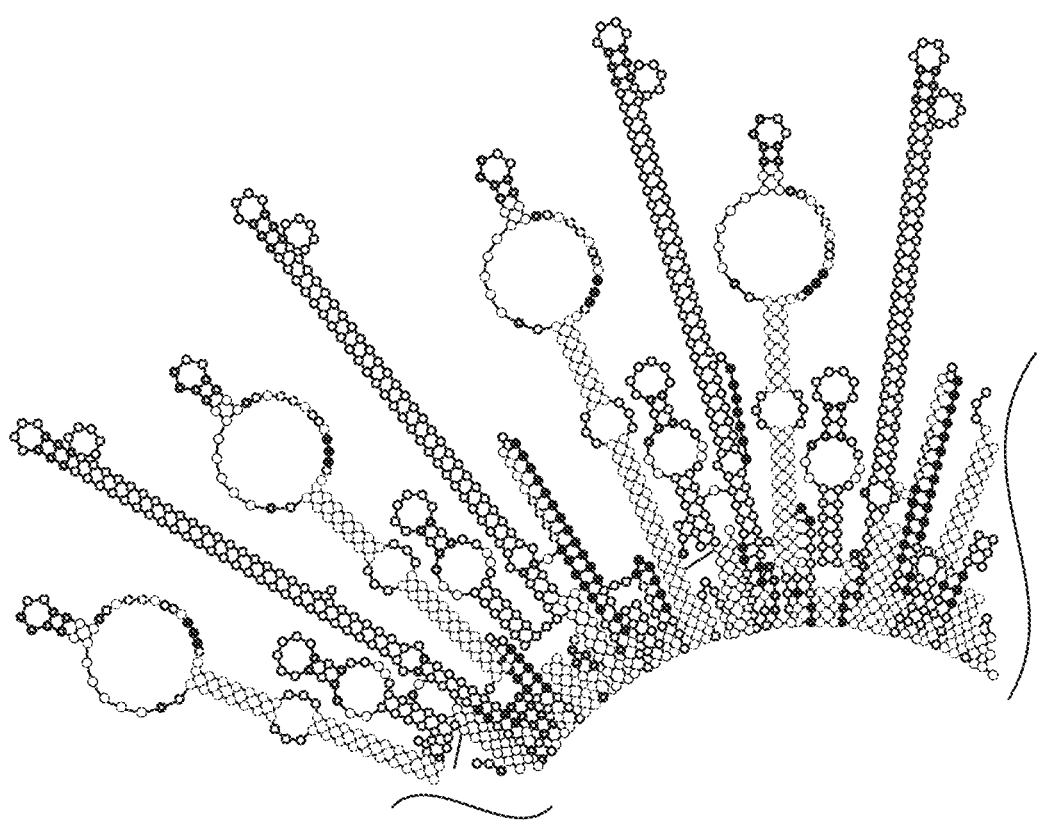

```
                          SEQUENCE LISTING

<160> NUMBER OF SEQ ID NOS: 15

<210> SEQ ID NO 1
<211> LENGTH: 111
<212> TYPE: DNA
<213> ORGANISM: Artificial Sequence
<220> FEATURE:
<223> OTHER INFORMATION: Synthetic polynucleotide

<400> SEQUENCE: 1
gattcgtcag tagggttgta aaggttttc ttttcctgag aaaacaacct tttgttttct      60
caggttttgc tttttggcct ttccctagct ttaaaaaaaa aaaagcaaaa c             111

<210> SEQ ID NO 2
<211> LENGTH: 2615
<212> TYPE: DNA
<213> ORGANISM: Artificial Sequence
<220> FEATURE:
<223> OTHER INFORMATION: Synthetic polynucleotide

<400> SEQUENCE: 2
actttaagta gaaggggatg tccaagtaat tttggttttc taactgttga atcataagct      60
tgacctgccc ccagaggctt tttggatgtt tttatctgtg ttttgccatc tctttacact    120
cctcgacatt cagtttacct taatcttcac atttttacac cttgggaagt ggcaagcatc    180
gctgggttta agataaagga gtcacaaaaa ctaatcaaaa taaatttgc attatgacaa     240 cttttaatac actttagcat tttatttgat tggttttttt ttttttgct tttagattta     300 atacatatac ggacgattgc acagacttgg ggacctgatg agtccgtgag gacgaaacga    360
gtaagctcgt cttaaaacag ctctggggtt gtacccaccc cagaggccca cgtggcggct    420
agtactccgg tattgcggta cccttgtacg cctgttttat actcccttcc cgtaacttag    480
acgcacaaaa ccaagttcaa tagaaggggg tacaaaccag taccaccacg aacaagcact    540
tctgtttccc cggtgatgtc gtatagactg cttgcgtggt tgaaagcgac ggatccgtta    600
tccgcttatg tacttcgaga agcccagtac cacctcggaa tcttcgatgc gttgcgctca    660
gcactcaacc ccagagtgta gcttaggctg atgagtctgg acatccctca ccggtgacgg    720
tggtccaggc tgcgttggcg gcctacctat ggctaacgcc atgggacgct agttgtgaac    780
aaggtgtgaa gagcctattg agctacataa gaatcctccg gcccctgaat gcggctaatc    840
ccaacctcgg agcaggtggt cacaaaccag tgattggcct gtcgtaacgc gcaagtccgt    900
ggcggaaccg actactttgg gtgtccgtgt ttccttttat tttattgtgg ctgcttatgg    960
tgacaatcac agattgttat cataaagcga aggtgccacc atggtgagcg agctgattaa   1020
ggagaacatg cacatgaagc tgtacatgga gggcaccgtg aacaaccacc acttcaagtg   1080
```

| | |
|---|---:|
| cacatccgag ggcgaaggca agccctacga gggcacccag accatgagaa tcaaggcggt | 1140 |
| cgagggcggc cctctcccct tcgccttcga catcctggct accagcttca tgtacggcag | 1200 |
| caaaaccttc atcaaccaca cccagggcat ccccgacttc tttaagcagt ccttccccga | 1260 |
| gggcttcaca tgggagagag tcaccacata cgaagatggg ggcgtgctga ccgctaccca | 1320 |
| ggacaccagc tccaggacg gctgcctcat ctacaacgtc aagatcagag gggtgaactt | 1380 |
| cccatccaac ggccctgtga tgcagaagaa aacactcggc tgggaggcct ccaccgagac | 1440 |
| actgtacccc gctgacggcg gcctggaagg cagagccgac atggccctga gctcgtggg | 1500 |
| cggggccac ctgatctgca accttaagac cacatacaga tccaagaaac ccgctaagaa | 1560 |
| cctcaagatg cccggcgtct actatgtgga caggagactg gaaagaatca aggaggccga | 1620 |
| caaagagaca tacgtcgagc agcacgaggt ggctgtggcc agatactgcg acctccctag | 1680 |
| caaactgggg cacaaactta attgagctta atcaacctct ggattacaaa atttgtgaaa | 1740 |
| gattgactgg tattcttaac tatgttgctc cttttacgct atgtggatac gctgctttaa | 1800 |
| tgcctttgta tcatgctatt gcttcccgta tggctttcat tttctcctcc ttgtataaat | 1860 |
| cctggttgct gtctctttat gaggagttgt ggcccgttgt caggcaacgt ggcgtggtgt | 1920 |
| gcactgtgtt tgctgacgca acccccactg gttgggcat gccaccacc tgtcagctcc | 1980 |
| tttccgggac tttcgctttc cccctcccta ttgccacggc ggaactcatc gccgcctgcc | 2040 |
| ttgcccgctg ctggacaggg gctcggctgt tgggcactga caattccgtg tgttgtcgg | 2100 |
| ggaagctgac gtcctttcca tggctgctcg cctgtgttgc cacctggatt ctgcgcggga | 2160 |
| cgtccttctg ctacgtccct tcggccctca atccagcgga ccttccttcc gcggcctgc | 2220 |
| tgccggctct gcggcctctt ccgcgtcttc gccttcgccc tcagacgagt cggatctccc | 2280 |
| tttgggccgc ctccccgcct gtttcgcctc ggcgtccggt ccgtgttgct ggtcttcac | 2340 |
| ctgtgcagac ttgcgaacca tggattcaat tgttgttgtt aaccggtgat tcgtcagtag | 2400 |
| ggttgtaaag gttttttcttt tcctgagaaa acaaccttt gttttctcag gttttgcttt | 2460 |
| ttggcctttc cctagcttta aaaaaaaaaa agcaaaactc accgaggcag ttccatagga | 2520 |
| tggcaagatc ctggtattgg tctgcgaggc cggcatggtc ccagcctcct cgctggcgcc | 2580 |
| ggctgggcaa catgcttcgg catggcgaat gggac | 2615 |

<210> SEQ ID NO 3
<211> LENGTH: 88
<212> TYPE: DNA
<213> ORGANISM: Artificial Sequence
<220> FEATURE:
<223> OTHER INFORMATION: Synthetic polynucleotide

<400> SEQUENCE: 3

| | |
|---|---:|
| ttaaaacagc tctggggttg tacccacccc agaggcccac gtggcggcta gtactccggt | 60 |
| attgcggtac ccttgtacgc ctgtttta | 88 |

<210> SEQ ID NO 4
<211> LENGTH: 497
<212> TYPE: DNA
<213> ORGANISM: Artificial Sequence
<220> FEATURE:
<223> OTHER INFORMATION: Synthetic polynucleotide

<400> SEQUENCE: 4

| | |
|---|---:|
| agttcaatag aaggggggtac aaaccagtac caccacgaac aagcacttct gtttccccgg | 60 |
| tgatgtcgta tagactgctt gcgtggttga aagcgacgga tccgttatcc gcttatgtac | 120 |

```
ttcgagaagc ccagtaccac ctcggaatct tcgatgcgtt gcgctcagca ctcaacccca    180
gagtgtagct taggctgatg agtctggaca tccctcaccg gtgacggtgg tccaggctgc    240
gttggcggcc tacctatggc taacgccatg ggacgctagt tgtgaacaag gtgtgaagag    300
cctattgagc tacataagaa tcctccggcc cctgaatgcg gctaatccca acctcggagc    360
aggtggtcac aaaccagtga ttggcctgtc gtaacgcgca agtccgtggc ggaaccgact    420
actttgggtg tccgtgtttc cttttatttt attgtggctg cttatggtga caatcacaga    480
ttgttatcat aaagcga                                                  497
```

<210> SEQ ID NO 5
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 5

```
ggccggcatg gtcccagcct cctcgctggc gccggctggg caacatgctt cggcatggcg    60
aatgggac                                                             68
```

<210> SEQ ID NO 6
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 6

```
ggggacctga tgagtccgtg aggacgaaac gagtaagctc gtc                      43
```

<210> SEQ ID NO 7
<211> LENGTH: 658
<212> TYPE: DNA
<213> ORGANISM: Artificial Sequence
<220> FEATURE:
<223> OTHER INFORMATION: Synthetic polynucleotide

<400> SEQUENCE: 7

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg gctcggctg   360 ttgggcactg acaattccgt ggtgttgtcg gggaagctga cgtcctttcc atggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tgtttcgcct   600
cggcgtccgg tccgtgttgc ttggtcttca cctgtgcaga cttgcgaacc atggattc     658
```

<210> SEQ ID NO 8
<211> LENGTH: 420
<212> TYPE: DNA
<213> ORGANISM: Artificial Sequence
<220> FEATURE:

<223> OTHER INFORMATION: Synthetic polynucleotide

<400> SEQUENCE: 8

| taaagcttga ggtgagtatg tgctcgcttc ggcagcacat atactatgtt gaatgaggct | 60 |
| tcagtacttt acagaatcgt tgcctgcaca tcttggaaac acttgctggg attacttctt | 120 |
| caggttaacc caacagaagg ctcgagtgct gttgacagtg agcgccgctt gaagttttta | 180 |
| attaaatagt gaagccacag atgtatttaa ttaaagactt caagcggtgc ctactgcctc | 240 |
| ggagaattca aggggctact ttaggagcaa ttatcttgtt tactaaaact gaataccttg | 300 |
| ctatctcttt gatacatttt tacaaagctg aattaaaatg gtataaatta aatcactttt | 360 |
| ttcaattgtt tcctttttt tcctcagggt acccagcttt cttgtacaaa gtggtacgcg | 420 |

<210> SEQ ID NO 9
<211> LENGTH: 100
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (80)..(100)
<223> OTHER INFORMATION: may be absent

<400> SEQUENCE: 9

| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa | 100 |

<210> SEQ ID NO 10
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 10

| aaaaaaaaaa aaaa | 14 |

<210> SEQ ID NO 11
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 11

| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa | 100 |

<210> SEQ ID NO 12
<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 12

| ctcaccgagg acactggggg caaggggggac ctgatgagct ttttgcgaa acgagtaagc | 60 |
| tcgtc | 65 |

<210> SEQ ID NO 13
<211> LENGTH: 156

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (58)..(79)
<223> OTHER INFORMATION: n is a, c, g, t or u
<220> FEATURE:
<221> NAME/KEY: misc_feature
<222> LOCATION: (98)..(119)
<223> OTHER INFORMATION: n is a, c, g, t or u

<400> SEQUENCE: 13
ucgacuuguu aacccaacag aaggcucgag aagguauauu gcuguugaca gugagcgnnn        60
nnnnnnnnnn nnnnnnnnna gugaagccac agauguannn nnnnnnnnnn nnnnnnnnnu       120
gccuacugcc ucggacuuca aggggcuaga auugga                                 156

<210> SEQ ID NO 14
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 14
aaaaaaaaaa                                                               10

<210> SEQ ID NO 15
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 15
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
```

ENGINEERED POST-POLY A SIGNAL RNA AND USES THEREOF

RELATED APPLICATION

This application claims priority under 35 U.S.C. § 119(e) to U.S. Provisional Application Ser. No. 62/849,424, filed May 17, 2019, the entire contents of which are incorporated by reference herein.

FEDERALLY SPONSORED RESEARCH

This invention was made with Government support under Grant No. CBET0939511 awarded by the National Science Foundation (NSF). The Government has certain rights in the invention.

BACKGROUND

Gene silencing that occur when a synthetic gene circuit is introduced into an endogenous network is a long standing problem in synthetic biology and genetic engineering. Gene silencing is especially problematic for circuits that are integrated into a mammalian genome and the problem is worse for large and/or complex genetic circuits.

SUMMARY

There is a need to embed synthetic control elements into endogenous transcriptional genetic circuits that can effectively "re-wire" endogenous genetic program while avoiding epigenetic silencing problems of newly introduced control elements.

In eukaryotes, following recognition of the poly-A-signal and a successful termination signal, the transcription complex does not immediately dissociate from the template strand, but continues transcription of several thousand nucleotides downstream of the PAS, which leads to the production of a residual, immature and unprotected RNA transcript. There are no known cases where this residual transcript leads to functional RNA, and the residual RNA is expected to be short-lived due to unprotected 5' and 3' ends which are recognized by exonucleases.

Aspects of the present disclosure relates to an engineered nucleic acid including, from 5' to 3': a nucleotide sequence encoding a post-poly A signal (post-PAS) RNA 3' to a terminator. In some embodiments, the terminator is derived from a terminator region of a gene. In some embodiments, the terminator region is a SRY-Box 17 (Sox17) terminator region, a ribosomal protein S14 (RPS14) terminator region, a Serine And Arginine Rich Splicing Factor 3 (SRSF3) terminator region, or a Glyoxalase I (GLO1) terminator region.

In some embodiments, the terminator includes a nucleotide sequence encoding a poly A signal. In some embodiments, the poly A signal is a poly A signal having a nucleotide sequence of AAUAAA. In some embodiments, the terminator further includes a poly A tail or a synthetic poly A mimic 3' to the poly A signal. In some embodiments, the terminator comprises a nucleotide sequence encoding a RNA cleavage site between the poly A signal and the poly A tail or the synthetic poly A mimic, wherein the RNA cleavage site is capable of being cleaved by Cleavage and polyadenylation specificity factor (CPSF). In some embodiments, a nucleotide sequence $(N)_x$ is present poly A signal and the poly A tail or the synthetic poly A mimic, N can be any nucleotides, and X is between 10 and 40. In some embodiments, X is 25.

In some embodiments, poly A tail includes a nucleic acid sequence of $(A)_N$. In some embodiments, N is between 1-1000. In other examples, the synthetic poly A mimic is a triplex. In some embodiments, the post-PAS RNA is 100 nucleotides, 200 nucleotides, 300 nucleotides, 500 nucleotides, 1000 nucleotides or more 3' to the poly A signal.

In some embodiments, the engineered nucleic acid encoded post-PAS RNA includes a protein-coding cassette. In some embodiments, the post-PAS RNA comprises one or more protein-coding cassette. In some embodiments, the protein-coding cassette from 5' to 3' includes: a nucleotide sequence encoding a first RNA cleavage site, a nucleotide sequence encoding a 5' cap, a nucleotide sequence encoding an internal ribosome entry site (IRES), a nucleotide sequence encoding the protein, a nucleotide sequence encoding a 3' cap, and a nucleotide sequence encoding a second RNA cleavage site. In some embodiments, the protein coding cassette encodes a therapeutic protein, a reporter protein, regulatory proteins, activators or repressors of transcription or translation, DNA editing proteins, signaling proteins, enzymes, biosynthetic pathway components, cytotoxic proteins, or antibodies.

In some embodiments, the 5' cap is a clover-leaf. In some embodiments, the clover-leaf is derived from poliovirus mRNA. In some embodiments, the 3' cap is a poly A tail or a poly-A tail mimic. In some embodiments, the poly-A tail mimic is a triplex. In some embodiments, the triplex is derived from metastasis associated lung adenocarcinoma transcript 1 long non-coding RNA (MALAT1 lnc-RNA). In some embodiments the protein cassette further a nucleotide sequence encoding a woodchuck hepatitis virus posttranscriptional regulatory element (WPRE) between the nucleotide sequence encoding the protein coding RNA and the nucleotide sequence encoding the 3' cap.

In some embodiments, the nucleotide sequence encoding the post-PAS RNA comprises a non-coding RNA cassette. In some embodiments, the non-coding RNA cassette is an RNA encoding a miRNA cassette comprising a nucleotide sequence encoding a primary micro-RNA (pri-miRNA). In some embodiments, the nucleotide sequence encoding the post-PAS RNA comprises one or more miRNA cassette. In some embodiments, the miRNA cassette from 5' to 3' comprises: a nucleotide sequence encoding a first RNA cleavage site, the nucleotide sequence encoding the pri-miRNA, and a nucleotide sequence encoding a second RNA cleavage site. In some embodiments, the one or more miRNA cassette encodes the same miRNA. In other embodiments, the one or more miRNA cassette encodes different miRNAs. In some embodiments, the pri-miRNA further includes a miR-E element at the 3' end of the pri-miRNA.

In some embodiments the non-coding RNA cassette is gRNA cassette comprising a nucleotide sequence encoding a guide RNA (gRNA). In some embodiments, the nucleotide sequence encoding the post-PAS RNA comprises one or more gRNA cassette. In some embodiments, the gRNA cassette from 5' to 3' comprises: a nucleotide sequence encoding a first RNA cleavage site, the nucleotide sequence encoding RNA for expressing the gRNA, and a nucleotide sequence encoding a second RNA cleavage site. In some embodiments, the one or more gRNA cassette encodes the same gRNA. In other embodiments, ore or more gRNA cassette encodes different gRNA.

In some embodiments, the first and second RNA cleavage sites are nuclease sites. In other embodiments, the first and second RNA cleavage sites are RNA self-cleavage sites. In some embodiments, the first and second RNA self-cleavage sites are small self-cleaving ribozymes, such as hammerhead ribozyme, hairpin ribozyme, hepatitis delta virus (HDV) ribozyme, Varkud satellite (VS) ribozyme, and glmS ribozyme. In some embodiments, the first RNA self-cleavage site is a hepatitis delta virus (HDV) ribozyme. In some embodiments, the engineered nucleic acid further comprises a nucleotide sequence encoding a Pol III terminator between the HDV ribozyme and the non-coding RNA cassette. In some embodiments, the second RNA self-cleavage site is a hammerhead (HH) ribozyme.

In other embodiments, the engineered nucleic acid encoding post-PAS non-coding RNA further includes a third RNA self-cleavage site between the poly A signal and the first RNA self-cleavage site. In some embodiments, the third RNA self-cleavage site is a hepatitis delta virus (HDV) ribozyme. In some embodiments, the first RNA self-cleavage site is a hammerhead (HH) ribozyme, and the second RNA self-cleavage site is a hepatitis delta virus (HDV) ribozyme. In one example, the first RNA self-cleavage site is a hammerhead_56 ribozyme (HHR_56 ribozyme), the second RNA self-cleavage site is a hepatitis delta virus_84 ribozyme (HDV_84 ribozyme) and the third RNA self-cleavage site is a hepatitis delta virus_140 ribozyme (HDV_140 ribozyme).

Any of the engineered nucleic acid provided herein, may further include a promoter operably linked to a nucleic acid sequence encoding a transgene 5' to the terminator. In some embodiments, the engineered nucleic acid described herein replaces a terminator region of the transgene.

Other aspects of the disclosure relates to a vector including the engineered nucleic acid of the present disclosure. In some embodiments, vector is a plasmid, a RNA replicon, or a viral vector.

Also provided herein are cells including the engineered nucleic acid and/or vectors of the present disclosure. In some embodiments, engineered nucleic acid is located at the terminator region of an endogenous gene. In some embodiments, the endogenous gene is a housekeeping gene or a non-housekeeping gene. In some embodiments, the housekeeping gene is a Glyceraldehyde: 3-phosphate dehydrogenase (GAPDH) gene, a Macrophage Migration Inhibitory Factor (MIF) gene, a Small Nuclear Ribonucleoprotein D2 Polypeptide (SNRPD2) gene or an Eukaryotic Translation Elongation Factor 1 Alpha 1 (EEF1A1) gene. In some embodiments, the cell is a eukaryotic cell or a prokaryotic cell. In some embodiments, the eukaryotic cell is a human cell or a non-human cell.

Other aspects of the disclosure relates to an animal that has the engineered nucleic acid, vector or cells described herein. In some embodiments, the animal is a non-human animal.

In other aspects, the present disclosure provides a method for reducing epigenetic silencing of a targetgene circuit in a cell, the method includes: replacing a terminator region of an endogenous gene of the cell with the engineered nucleic acid described herein.

Another aspect of the disclosure relates to a method for regulating the expression of an exogenous gene circuit in a cell, the method includes replacing a terminator region of an endogenous gene of the cell with the engineered nucleic acid described herein.

Another aspect of the disclosure relates to a method for r for reporting the expression of an endogenous gene, the method includes replacing a terminator region of an endogenous gene of the cell with the engineered nucleic acid described herein.

Another aspect of the disclosure relates to a method for epigenetic silencing of an endogenous gene, the method includes replacing a terminator region of an endogenous gene of the cell with the engineered nucleic acid described herein.

Other aspects of the disclosure relate to a method for introducing a genetic modification in a cell, the method includes: (i) expressing a Cas9 chimera protein in the cell; and (ii) replacing a terminator region of a second endogenous gene of the cell with the engineered nucleic acid encoding gRNA. In some embodiments, the gRNA can direct the Cas9 to a target site for genetic modification.

Other aspects of the disclosure relates to a method for regulation of transcription of a target gene in a cell, the method includes: (i) expressing a Cas9 chimera protein in the cell; and (ii) replacing a terminator region of a second endogenous gene of the cell with the engineered nucleic acid encoding gRNA. In some embodiments, the gRNA can direct the Cas9 to a target site for genetic modification. In some embodiments, expressing the Cas9 chimera protein includes: a. transfecting the cell with a Cas9 chimera protein coding nucleic acid or vector; or b. transducing the cell with a Cas9 chimera protein coding virus; or c. replacing the engineered nucleic acid described herein, at a terminator region of a second endogenous gene of the cell. In some embodiments, the protein coding RNA encodes a Cas9 chimera protein. In some embodiments, the Cas9 chimera protein includes: (i) a nuclease dead. Cas9 (dCas9); and (ii) transcription factors.

Other aspects of the disclosure relates to a method for directed differentiation of stem cells, the method comprising replacing a terminator region of a stem cell specific gene of the cell with the engineered nucleic acid described herein. In some embodiments, the stem cell specific gene is Sox17.

In some embodiments, the nucleotide sequence encoding the post poly A RNA comprises a protein coding cassette. In some embodiments, the protein coding cassette encodes a protein capable of directing differentiation of the stem cell.

In some embodiments, the nucleotide sequence encoding the post poly A RNA comprises a miRNA cassette. In some embodiments, the miRNA, cassette encodes a miRNA capable of directing differentiation of the stem cell.

In some embodiments, the stem cell is differentiated into a pancreatic organoid. In some embodiments, the gene capable of directing differentiation of the stem cell into a pancreatic organoid is Pdx1.

In some embodiments, the nucleotide sequence encoding the post poly A RNA comprises a gRNA cassette. In some embodiments, the gRNA cassette encodes a gRNA capable of targeting a gene that regulates differentiation of the stem cell. In some embodiments, the method further comprises expressing a Cas9 chimera protein in the cell.

BRIEF DESCRIPTION OF DRAWINGS

FIG. 2A shows EYFP and mKate expression for constructs testing expression of miR-FF4 downstream of a polyA signal (PAS). FIG. 2B shows EYFP and mKate expression for constructs testing expression of a protein-coding RNA downstream of a polyA signal (PAS). FIG. 2C shows EYFP and mKate expression for constructs testing expression of gRNAs downstream of a polyA signal (PAS).

FIG. 3A shows the vectors transfected to HEK293 cells to test different terminators in producing gRNA downstream of PAS. FIG. 3B shows the vectors transfected to HEK293 cells to test different terminators in producing gRNA downstream of PAS, in which the post-PAS RNA either encodes a single gRNA cassette or three copies of gRNA cassettes. FIG. 3C shows expression of EYFP linked to various terminators can be induced by various doses of abscisic acid (ABA). FIG. 3D shows the expression of gRNAs downstream of the polyA signal (PAS) in different terminator regions. FIG. 3E shows quantification of fold-change in gRNA expression downstream of the PAS. FIG. 3F shows quantification of fold-change in EYFP expression induced by ABA. FIG. 3G shows constitutive EYFP expression with different terminators. FIG. 3H shows mKate expression indicating the gRNA can be expressed from all terminators. FIG. 3I shows the effect of gRNA expression downstream of a gene.

FIG. 5A is an illustration of mRNA processing and polyadenylation. FIG. 5B shows poly A signal and the length of additional poly A tail matters for upstream gene expression. FIG. 5C shows wild type Hepatitis deal virus (HDV) ribozyme has the best efficiency in RNA cleavage to release upstream mRNA and upstream gene expression. FIG. 5D shows that the identity of the poly A signal matters. Replacing the RPS21 poly A signal sequence with other poly A signal sequences (ADV and MIF) reduces expression of RPS21-2A-YFP from the endogenous RPS21 genomic locus. FIG. 5E shows that the full length poly A signal sequence is needed, showing that expression of RPS21-2A-YFP is reduced when using mutated RPS21 poly A signal (dPPA) or partial poly A signal (pPPA). FIG. 5F shows that length of the poly A tail after the poly A signal matters, showing that 100A essentially recovers WT expression of RPS21-2A-YFP. FIG. 5G is a schematic illustration showing the design of placing the poly A tail (N)x nucleotides away from the cleavage site. N can be any nucleotides, and X can be any number of nucleotides. FIG. 5H shows that placing poly A tail various nucleotides away from the cleavage site is beneficial in sustaining upstream gene expression.

FIG. 6A shows an exemplary design for a gRNA expression cassette. The construct includes, 5' to 3', upstream gene (e.g., EYFP), a poly A signal (e.g., AAUAAA), a poly A tail, a wild type HDV ribozyme, a hammer head ribozyme_56 (HHR_56), an RNA for expressing a gRNA, and a HDV_84 ribozyme (HDV_84). FIG. 6B is an structural illustration of the exemplary gRNA expressing post-PAS RNA. FIG. 6C shows that the gRNA is successfully produced from the construct to guided dCas9/VPR (VP64-p65-Rta activator) to activate tdTornato expression. FIG. 6D shows the quantification of fluorescence intensity of EYFP and tdTomato of FIG. 6C. FIG. 6E shows a construct expressing multiple gRNA cassettes in one post-PAS RNA. FIG. 6F shows that expressing multiple gRNAs in one post-PAS RNA did not affect upstream gene expression, and including multiple gRNA cassettes in one constructs leads to more gRNA production, as evidenced by higher tdTomato expression.

FIG. 7A shows an exemplary design for a miRNA expression cassette. The construct includes, 5' to 3', a upstream gene (e.g., EYFP), a poly A signal (e.g., AAUAAA), a poly A tail, a wild type HDV ribozyme, a hammer head ribozyme_56 (HHR_56), primary miR-FF4 (pri-miR-FF4), and a ribozyme (HDV_84). FIG. 7B shows a structural illustration of the exemplary miRNA. expressing post-PAS RNA in single copy or multiple copies. FIG. 7C is a schematic illustration of the above described process. FIG. 7D shows that the miRNA is successfully produced from the construct to inhibit mKate expression without affecting upstream EYFP expression. FIG. 7D shows that expressing multiple mi RNAs in one post-PAS RNA did not affect upstream gene expression, and including multiple miRNA cassettes in one constructs leads to more miRNA production, as evidenced by stronger mKate inhibition. FIG. 7E shows the incorporation of a miR-E element to the 3' of the pri-miR sequence in each miRNA cassette. FIG. 7F shows stable YFP expression (representative of constitutive gene expression) with up to four repeats of downstream miRNA expression.

FIG. 8A shows general schematics of "one-to-one", "one-to-many", and "AND logic" transcriptional regulation. FIG. 8B shows "one-to-one" inhibition: a single endogenous gene transcript generates gRNA that promotes inhibition of a single endogenous promoter of interest. FIG. 8C shows gRNA do not alter the wild-type expression levels of the modified genes. FIG. 8D shows experimental regulation of the activation level of a gene of interest via the number of gRNA expressed, such that multiple co-expressed gRNAs produce a corresponding increase in inhibition or activation strength. FIG. 8E shows addition of multiple gRNA cassettes has minimal effect on expression of endogenous gene. FIG. 8F shows "one-to-many" inhibition: a single endogenous gene transcript generates different gRNAs, thereby inhibiting multiple endogenous genes. In one-to-many rewiring, different genes are simultaneously inhibited or activated simply by encoding different gRNAs. FIG. 8G shows "AND logic" inhibition: simultaneously expressed endogenous gene transcripts generate dCas9-TI and gRNA, inhibiting an endogenous promoter of interest only when both input conditions are true. In a 2-input AND logic rewiring, two cellular events must occur simultaneously to inhibit or activate an endogenous gene of interest.

FIG. 9A shows the schematic design showing the construct where a Pol III terminator is placed between the HDV and the gRNA cassette. FIG. 9B shows that the Pol III terminator is effective in preventing HDV driven gRNA expression independent of the expression of the upstream gene.

FIG. 10A shows the steps of integrating a post PAS RNA encoding gRNA to the terminator region of an endogenous Sox17 gene. FIG. 10B show endoderm cells positive for EYFP expression.

DETAILED DESCRIPTION

Figure 1:
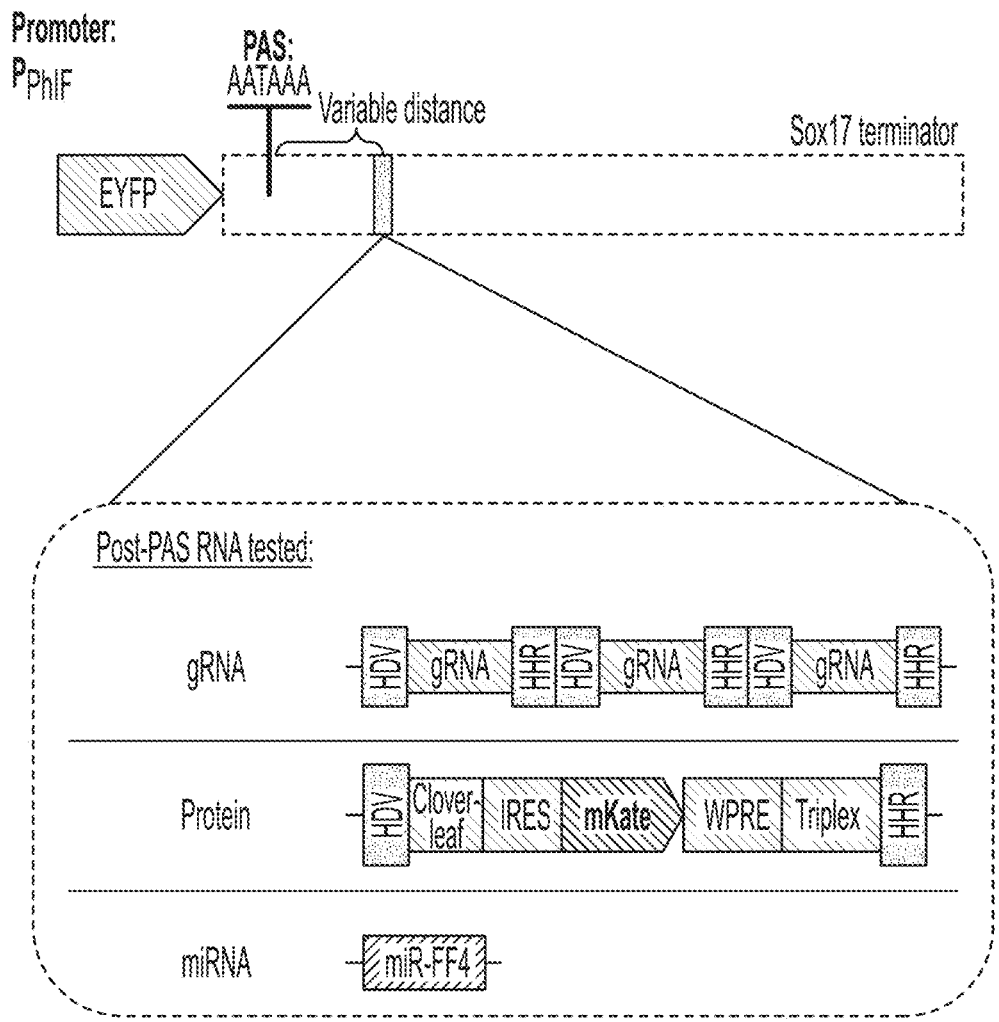
FIG. 1 is a schematic illustration of various designs of post-poly A signal (post-PAS) RNA for expressing gRNA, protein or micro-RNA (miRNA). A construct including a $P_{phIF}$ promoter driving the expression of enhanced yellow fluorescent protein (EYFP), and a Sox17 terminator region downstream to the coding sequence of EYFP was designed to test the post-PAS expression. The $P_{phIF}$ promoter can be induced by a abscisic acid (ABA). The post-PAS RNA can be located at the Sox17 terminator region at various distance 3' to the poly A signal. The post-PAS RNA can encode a protein, a miRNA or a gRNA.

The instant disclosure, at least in part, relates to the unexpected finding that residual transcriptional activity of nucleotides downstream of a terminator (e.g., a post-poly A signal) of a gene (e.g., a housekeeping gene) in a cell (e.g., a eukaryotic cell), can be engineered to yield functional RNA (e.g., protein-coding RNA, guide RNA, or microRNA). Embedding various expression cassette to be transcribed as post-poly A RNA also reduces epigenetic silencing of the expression cassette. Provided herein are designs of engineered nucleic acid for expression of functional, mature and stable RNA in the terminator region of a gene. Also described herein, at least in part, are novel embedded synthetic biology methods that provide the ability to rewire a cell's endogenous regulatory networks while addressing the long-standing problem of how to provide sustained functioning circuits without epigenetic silencing that plagues many synthetic integrated circuits. Embedded synthetic biology circuits both respond to endogenous signals and provide new control of other endogenous signals without being silenced.

I. Engineered Nucleic Acid Encoding Post-Poly A Signal RNA

Aspects of the present disclosure provides an engineered nucleic acid, from 5' to 3', comprising a nucleotide sequence encoding a post-poly A signal RNA (post-PAS RNA) 3' to a terminator. An engineered nucleic acid is a nucleic acid that is not "naturally occurring." The engineered nucleic acid of the present disclosure may be produced using recombinant cloning and/or nucleic acid amplification technology, including polymerase chain reaction (PCR) (see U.S. Pat. Nos. 4,683,202 and 5,928,906).

A terminator, as used herein, refers to a section of nucleic acid sequence that marks the end of a gene or operon in DNA during transcription. This sequence mediates transcriptional termination by providing signals in the newly synthesized transcript RNA that trigger processes which release the transcript RNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. In some embodiments, the terminator comprises a nucleotide sequence encoding a polyadenylation signal (poly A signal). In some embodiments, the poly A signal is a sufficiently strong poly A signal for transcriptional termination. In some embodiments, the sufficiently strong poly A signal comprises a central sequence motif AAUAAA. In other examples, the sufficiently strong poly A signal comprises close variant of the sequence AAUAAA, such as AU/GUAAA or UAUAAA (Wickens and Stephenson 1984; Zhao et al. 1999).

A terminator region, as used herein, refers to the section of nucleotide sequence from the downstream of a terminator (including the terminator) that would be transcribed by RNA polymerase II after termination signal to be a residue RNA. During these processing steps of transcriptional termination and polyadenylation of the upstream gene, the RNA polymerase complex continues to transcribe for several hundred to a few thousand bases downstream of the PAS and eventually dissociates from the, DNA and downstream transcript, which leads to the production of a naturally occurring residual, immature and unprotected post-PAS RNA transcript. The naturally occurring post-PAS RNA transcript can be a non-functional RNA and is prone to degradation due to unprotected 5' and 3' ends which are recognized by exonucleases. In some embodiments, the terminator in the engineered nucleic acid described herein, is derived from a terminator region of a gene. In some embodiments, the terminator can be derived from a SRY-Box 17 (Sox17) terminator region, a ribosomal protein S14 (RPS14) terminator region, a Serine and Arginine Rich Splicing Factor 3 (SRSF3) terminator region, or a Glyoxalase I (GLO1) terminator region. Other terminator region not specifically mention in the present disclosure can be used as needed.

In eukaryotic transcription of mRNAs, terminator signals (e.g., PAS signal AAUAAA) are recognized by protein factors that are associated with the RNA polymerase II and which trigger the termination process. Once the poly-A signals (e.g., AAUAAA) are transcribed into the mRNA, the proteins cleavage and polyadenylation specificity factor (CYST) and cleavage stimulation factor (CstF) transfer from the carboxyl terminal domain of RNA polymerase II to the snRNA. These two factors then recruit other proteins to the site to cleave the transcript, freeing the mRNA from the transcription complex, and add a string poly A tail to the 3' end of the mRNA in a process known as polyadenylation. Polyadenylation is the addition of a poly(A) tail to a messenger RNA. The poly A tail consists of multiple adenosine monophosphates. In eukaryotes, polyadenylation is part of the process that produces mature messenger RNA (mRNA) for translation. mRNA molecules in both prokaryotes and eukaryotes have polyadenylated 3'-ends, with the prokaryotic poly A tails generally shorter and less mRNA molecules polyadenylated (Sarkar et al, "Polyadenylation of mRN A in Prokaryotes". *Annual Review of Biochemistry*. 66 (1): 173-197). In some embodiments, the poly A signal further comprises a poly A tail. In some embodiments, the poly A tail comprises a nucleic acid sequence of $(A)_N$. In some embodiments, the poly A tail includes anywhere between 1-1000 adenine. In some embodiments, the poly A tail is 1, 2, 3, 4, 5, 10, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, or 1000 adenines. In some embodiments, the terminator further comprises a synthetic poly A mimic. A poly A tail mimic, as used herein, refers to a nucleotide structure that functionally mimics a poly A tail. In some embodiments, the poly A tail mimic is a triplex. A triplex, as used herein, refers to a bipartite triple helix that sequesters the 3' end of the RNA within a U•A-U triple, conferring resistance to rapid RNA decay. In some embodiments, the triplex is derived from metastasis associated lung adenocarcinoma transcript 1 long non-coding RNA (MALAT1 lnc-RNA). Long noncoding RNAs (lncRNAs) function in myriad cellular processes and are associated with various disease states, including cancer. Fluman metastasis-associated lung adenocarcinoma transcript 1 (MALAT1) is an abundant, ~8-kb lncRNA that is upregulated in multiple cancers. High nuclear levels of MALAT1, with a half-life up to 15 h, promote tumor growth by affecting proliferation, invasion and metastasis, processes associated with altered gene expression in lung cancer. The enhancement of oncogenic processes by MALAT1 in colorectal cancer cells has been localized to a ~1500-nucleotide (nt) fragment near the 3' end (nts 6918-8441)5. A 3' triplex structure is shown to confer stability of the MALAT1 lncRNA (Brown et al., Nat Struct Mol Biol. 2014 July; 21(7): 633-640). Exemplary nucleotide sequence of MALAT1 lncRNA triplex is set forth in SEQ ID NO: 1:

```
                                          (SEQ ID NO: 1)
GATTCGTCAGTAGGGTTGTAAAGGTTTTTCTTTTCCTGAGAAAACA

ACCTTTTGTTTTCTCAGGTTTTGCTTTTTGGCCTTTCCCTAGCTTT

AAAAAAAAAAAGCAAAAC.
```

In some embodiments, a poly A tail or the synthetic poly A mimic is placed $(N)_x$ nucleotides away from the mRNA cleavage site. In some embodiments, such placement is beneficial in sustaining upstream gene expression. In some embodiments, N can any of the A, T, G, or C nucleotides. In some embodiments, the poly A tail can be placed 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more nucleotides away from the cleavage site. In some embodiments, the poly A tail can be placed between 5 and 10 nucleotides. between 5 and 15 nucleotides, between 5 and 20 nucleotides, between 5 and 25 nucleotides, between 5 and 30 nucleotides, between 5 and 40 nucleotides, between 10 and 20 nucleotides, between 10 and 25 nucleotides, between 10 and 30 nucleotides, between 10 and 35 nucleotides; between 10 and 40 nucleotides, between 15 and 20 nucleotides, between 15 and 25 nucleotides, between 15 and 30 nucleotides, between 15 and 35 nucleotides, between 15 and 40 nucleotides, between 20 and 25 nucleotides, between 20 and 30 nucleotides, between 20 and 35 nucleotides, between 20 and 40 nucleotides, between 25 and 30 nucleotides, between 25 and 35 nucleotides, or between 25 and 40 nucleotides. In some embodiments, the poly A tail is placed 25 nucleotides away from the cleavage site.

The present disclosure, at least in part, provides an engineered nucleic acid, encoding an engineered post-PAS RNA 3' to a terminator, which is a functional, mature and stable RNA. The engineered post-PAS RNA can be positioned at various distance downstream of the PAS signal. In some embodiments, the post-PAS RNA can be at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 20 nucleotides, at least 30 nucleotides, at least 40 nucleotides, at least 50 nucleotides, at least 60 nucleotides, at least 70 nucleotides, at least 80 nucleotides. at least 90 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, at least 1500 nucleotides, at least 2000 nucleotides, at least 2500 nucleotides, at least 3000 nucleotides, or more nucleotides downstream of the post-PAS signal.

The engineered nucleic acid provided herein, may further comprise a promoter operably linked to a nucleic acid sequence encoding a transgene 5' to the terminator. In some embodiments, the engineered nucleic acid encoding the post-PAS RNA replaces a terminator region of the transgene. A transgene, as used herein, refers to a gene or genetic material that has been transferred naturally, or by any of a number of genetic engineering techniques from one organism to another. The introduction of a transgene has the potential to change the phenotype of an organism. A promoter refers to a DNA sequence recognized by the synthetic machinery of the cell, or introduced synthetic machinery, required to initiate the specific transcription of a gene. The phrases "operably linked," "operatively positioned," "under control," or "under transcriptional control" means that the promoter is in the correct location and orientation in relation to the nucleic acid to control RNA polymerase initiation and expression of the gene.

In some embodiments, the engineered post-PAS RNA comprises a protein coding RNA. In some embodiments, the engineered post—PAS RNA comprises a non-coding RNA. In some embodiments, the non-coding RNA is a microRNA. In other examples, the non-coding RNA is guild RNA (gRNA).

(i) Post-poly A RNA for Expression of a Protein-coding RNA

Aspects of the present disclosure relate to engineered nucleic acid, encoding a post-PAS RNA comprises a protein coding RNA. In some embodiments, the post-PAS RNA comprises one or more protein-coding cassette. A protein-coding cassette, as used herein, refers to an expression cassette for expression of a protein coding RNA. In addition to the protein coding sequence, the protein coding cassette may further comprise regulatory elements of various functions, such as RNA cleavage, RNA splicing, translation initiation, increased RNA stability, nuclear export, transcriptional termination, transcriptional and/or translational regulation or the combination thereof. In one example, the protein coding cassette from 5' to 3' comprises: a first RNA cleavage site (e.g., a nuclease site or a ribozyme), a 5' cap (e.g., a clover-leaf), a translational initiation site (e.g., an internal ribosome entry site (IRES)), the protein coding RNA, a 3' cap (e.g., a triplex), and a second RNA cleavage site (e.g., a nuclease site or a ribozyme). An exemplary engineered nucleic acid sequence encoding a post PAS RNA for a protein (e.g., mkate) is set forth in SEQ ID NO: 2:

```
                                          (SEQ ID NO: 2)
ACTTTAAGTAGAAGGGGATGTCCAAGTAATTTTGGTTTTCTAACTGT

TGAATCATAAGCTTGACCTGCCCCCAGAGGCTTTTTGGATGTTTTA

TCTGTGTTTTGCCATCTCTTTACACTCCTCGACATTCAGTTTACCTT

AATCTTCACATTTTTACACCTTGGGAAGTGGCAAGCATCGCTGGGTT

TAAGATAAAGGAGTCACAAAAACTAATCAAAATAAAATTTGCATTAT

GACAACTTTTAATACACTTTAGCATTTTATTTGATTGGTTTTTTTT

TTTTTGCTTTTAGATTTAATACATATACGGACGATTGCACAGACTTG

GGGACCTGATGAGTCCGTGAGGACGAAACGAGTAAGCTCGTCTTAAA

ACAGCTCTGGGGTTGTACCCACCCCAGAGGCCCACGTGGCGGCTAGT

ACTCCGGTATTGCGGTACCCTTGTACGCCTGTTTTATACTCCCTTCC

CGTAACTTAGACGCACAAAACCAAGTTCAATAGAAGGGGGTACAAAC
```

```
CAGTACCACCACGAACAAGCACTTCTGTTTCCCCGGTGATGTCGTAT

AGACTGCTTGCGTGGTTGAAAGCGACGGATCCGTTATCCGCTTATGT

ACTTCGAGAAGCCCAGTACCACCTCGGAATCTTCGATGCGTTGCGCT

CAGCACTCAACCCCAGAGTGTAGCTTAGGCTGATGAGTCTGGACATC

CCTCACCGGTGACGGTGGTCCAGGCTGCGTTGGCGGCCTACCTATGG

CTAACGCCATGGGACGCTAGTTGTGAACAAGGTGTGAAGAGCCTATT

GAGCTACATAAGAATCCTCCGGCCCCTGAATGCGGCTAATCCCAACC

TCGGAGCAGGTGGTCACAAACCAGTGATTGGCCTGTCGTAACGCGCA

AGTCCGTGGCGGAACCGACTACTTTGGGTGTCCGTGTTTCCTTTTAT

TTTATTGTGGCTGCTTATGGTGACAATCACAGATTGTTATCATAAAG

CGAAGGTGCCACCATGGTGAGCGAGCTGATTAAGGAGAACATGCACA

TGAAGCTGTACATGGAGGGCACCGTGAACAACCACCACTTCAAGTGC

ACATCCGAGGGCGAAGGCAAGCCCTACGAGGGCACCCAGACCATGAG

AATCAAGGCGGTCGAGGGCGGCCCTCTCCCCTTCGCCTTCGACATCC

TGGCTACCAGCTTCATGTACGGCAGCAAAACCTTCATCAACCACACC

CAGGGCATCCCCCACTTCTTTAAGCAGTCCTTCCCCGAGGGCCTTCA

CATGGGAGGAGTCACCACATACGAAGATGGGGGCGTGCTGACCGCTA

CCCAGGACACCAGCCTCCAGGACGGCTGCCTCATCTACAACGTCAAG

ATCAGAGGGGTGAACTTCCCATCCAACGGCCCTGTGATGCAGAAGAA

AACACTCGGCTGGGAGGCCTCCACCGAGACACTGTACCCCGCTGACG

GCGGCCTGGAAGGCAGAGCCGACATGGCCCTGAAGCTCGTGGGCGGG

GGCCACCTGATCTGCAACCTTAAGACCACATACAGATCCAAGAAACC

CGCTAAGAACCTCAAGATGCCCGGCGTCTACTATGTGGACAGGAGAC

TGGAAAGAATCAAGGAGGCCGACAAAGAGACATACGTCGAGCAGCAC

GAGGTGGCTGTGGCCAGATACTGCGACCTCCCTAGCAAACTGGGGCA

CAAACTTAATTGAGCTTAATCAACCTCTCGATTACAAAATTTGTGAA

AGATTGACTGGTATTCTTAACTATGTTGCTCCTTTTACGCTATGTGG

ATACGCTGCTTTAATGCCTTTGTATCATGCTATTGCTTCCCGTATGG

CTTTCATTTTCTCCTCCTTGTATAAATCCTGGTTGCTGTCTCTTTAT

GAGGAGTTGTGGCCCGTTGTCAGGCAACGTGGCGTGGTGTGCACTGT

GTTTGCTGACGCAACCCCCACTGGTTGGGCATTGCCACCACCTGTC

AGCTCCTTTCCGGGACTTTCGCTTTCCCCCTCCCTATTGCCACGGCG

GAACTCATCGCCGCCTGCCTTGCCCGCTGCTGGACAGGGGCTCGGCT

GTTGGGCACTGACAATTCCGTGGTGTTGTCGGGGAAGCTGACGTCCT

TTCCATGGCTGCTCGCCTGTGTTGCCACCTGGATTCTGCGCGGGACG

TCCTTCTGCTACGTCCGCGTCTTCGCCTTCGCCCTCAGACGAGTCGG

ATCTCCCTTTGGGCCGCCTCCCCGCCTGTTTCGCCTCGGCGTCCGGT

CCGTGTTGCTTGGTCTTCACCTGTGCAGACTTGCGAACCATGGATTC

AATTGTTGTTAACCGGTGATTCGTCAGTAGGGTTGTAAAGGTTT

TTCTTTTCCTGAGAAAACAACCTTTTGTTTTCTCAGGTTTTGCTTTT

TGGCCTTTCCCTAGCTTTAAAAAAAAAAAAGCAAAACTCACCGAGGC

AGTTCCATAGGATGGCAAGATCCTGGTATTGGTCTGCGAGGCCGGCA

TGGTCCCAGCCTCCTCGCTGGCGCCGGCTGGGCAACATGCTTCGGCA

TGGCGAATGGGAC.
```

In some embodiments, the protein coding cassette comprises a protein coding RNA. The protein coding RNA can encode any protein of interest. Non-limiting examples of proteins encoded by the protein coding RNA can be therapeutic protein, reporter proteins, transcription regulatory protein, translational regulatory protein, enzymes, fusion protein, DNA editing proteins, signaling proteins, enzymes, biosynthetic pathway components, cytotoxic proteins, or antibodies, etc.

In some embodiments, the protein coding RNA encodes for a therapeutic protein. Non-limiting exemplary therapeutic proteins include interferon-γ (IFN-γ), IFN-α, Interleukin-1 (IL-1), IL-2, IL-3, IL-4, IL-5, IL-6, IL-7, IL-10, IL-12, IL-13, IL-17, IL-18, CCL14, CCL19, CCL20, CCL21, CCL25, CCL27, CXCL12, CXCL13, CXCL-8, CCL2, CCL3, CCL4, CCL5, CCL11, CXCL10, Adrenomedullin (AM), Angiopoietin (Ang), Autocrine motility factor, Bone morphogenetic proteins (BMPs), Ciliary neurotrophic factor ((ATP), Leukemia inhibitory factor (LIF), Interleukin-6 (IL-6), Macrophage colony-stimulating factor (m-CSF), Granulocyte colony-stimulating factor (G-CSF), Granulocyte macrophage colony-stimulating factor (GM-CSF), Epidermal growth factor (EGF), Ephrin A1, Ephrin A2, Ephrin A3, Ephrin A4, Ephrin A5, Ephrin B1, Ephrin B2, Ephrin B3, Erythropoietin (EPO), Fibroblast growth factor 1 (FGF1), Fibroblast growth factor 2 (FGF2), Fibroblast growth factor 3 (FGF3), Fibroblast growth factor 4 (FGF4), Fibroblast growth factor 5 (FGF5), Fibroblast growth factor 6 (FGF6), Fibroblast growth factor 7 (FGF7), Fibroblast growth factor 8 (FGF8), Fibroblast growth factor 9 (FGF9), Fibroblast growth factor 10 (FGF10), Fibroblast growth factor 11 (FGF11), Fibroblast growth factor 12 (FGF12), Fibroblast growth factor 13 (FGF13), Fibroblast growth factor 14 (FGF14), Fibroblast growth factor 15 (FGF15), Fibroblast growth factor 16 (FGF16), Fibroblast growth factor 17 (FGF17), Fibroblast growth factor 18 (FGF18), Fibroblast growth factor 19 (FGF19), Fibroblast growth factor 20 (FGF20), Fibroblast growth factor 21 (FGF21), Fibroblast growth factor 22 (FGF22), Fibroblast growth factor 23 (FGF23), Fetal Bovine Somatotropin (FBS), Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factor-1 (IGF-1), Insulin-like growth factor-2 (IGF-2), Keratinocyte growth factor (KGF), Migration-stimulating factor (MSF), Macrophage-stimulating protein (MSP), Myostatin (GDF-8), Neuregulin 1 (NRG1), Neuregulin 2 (NRG2), Neuregulin 3 (NRG3), Neuregulin 4 (NRG4), Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS), T-cell growth factor (TCGF), Thrombopoietin (TPO), Transforming growth factor alpha (TGF-α), Transforming growth factor beta (TGF-β), Tumor necrosis factor-alpha (TNF-α), Vascular endothelial growth factor (VEGF), antibodies, or peptide based inhibitors.

In some embodiments, the protein coding RNA encodes for a reporter protein. Non-limiting exemplary reporter proteins can be wt-GFP, green fluorescent protein (e.g., EGFP, Emerald, Superfolder GFP, Azami Green, mWasabi, TagGFP, TurboGFP, AcGFP, ZsGreen, T-Sapphire, etc.), blue fluorescent protein, (e.g., EBFP, EBFP2, Azurite, mTagBFP, etc.), cyan fluorescent protein (e.g., ECFP, mECFP, Cerulean, mTurquoise, CyPet, AmCyan1, Midori-Ishi Cyan, TagCFP, mTFP1 (Teal), etc.), yellow fluorescent protein (e.g., EYFP, Topaz, Venus, mCitrine, YPet, TagYFP, PhiYFP, ZsYellow1, mBanana, etc.), orange fluorescent protein (e.g., Kusabira Orange, Kusabira Orange2, mOrange, mOrange2, dTomato, dTomato-Tandem, TagRFP, TagRFP-T, I)sRed, DsRed2, DsRed-Express (T1), DsRed-Monomer, mTangerine, etc.), or red fluorescent protein (e.g., mRuby, mApple, mStrawberry, AsRed.2, mRFP1, JRed, mCherry, HcRed1, mRaspberry, dKeima-Tandem, HcRed-Tandem, mPlum, AQ143, etc.), luciferase, or b-galactosidase In some embodiments, the protein coding RNA encodes for a regulatory protein. Non-limiting exemplary regulatory proteins can be transcription factors, or translation regulatory protein.

In some embodiments, the protein coding RNA encodes for an enzyme. Non-limiting exemplary enzymes can be nucleases, proteases, kinases, lipase, amylase, etc. In some embodiments, the enzyme is a nuclease. In one example, the nuclease is Cas9.

In some embodiments, the protein coding RNA encodes for a chimeric protein. In some embodiments, the fusion protein is a Cas9 chimera protein. In one example, the Cas9 chimera protein is a fusion protein of a nuclease dead Cas9 (dCas9) and transcription factors.

Additionally to the protein coding RNA, the protein coding cassette further comprises various regulatory elements. In some embodiments, the protein coding cassette comprises a 5' cap. A 5' cap, refers to a specially altered nucleotide on the 5' end of some primary transcripts such as precursor messenger RNA. The 5' cap of an mRNA has various functions such as regulation of nuclear export (Visa et al., (1 Apr. 1996). "A nuclear cap-binding complex binds Balbiani ring pre-mRNA cotranscriptionally and accompanies the ribonucleoprotein particle during nuclear export". *The Journal of Cell Biology.* 133 (1): 5-14; Lewis et al., (15 Jul. 1997). "The Role of the Cap Structure in RNA Processing and Nuclear Export". *European Journal of Biochemistry*, 247 (2): 461-469); prevention of degradation by exonucleases (Bird et al., (2016). "The mechanism of RNA 5' capping with NAD(+), NADH and desphospho-CoA". *Nature.* 535 (7612): 444-7; Evdokimova et al., (1 Oct. 2001). "The major mRNA-associated protein YB-1 is a potent 5' cap-dependent mRNA stabilizer". *The EMBO Journal.* 20 (19): 5491-5502; Gao, Min; Fritz, David T.; Ford, Lance P.; Wilusz, Jeffrey (March 2000). "Interaction between a Poly(A)-Specific Ribonuclease and the 5' Cap Influences mRNA Deadenylation Rates In Vitro". *Molecular Cell.* 5 (3): 479-488; Burkard et al., (15 Jan. 2000). "A Nuclear 3'-5' Exonuclease Involved in mRNA Degradation Interacts with Poly(A) Polymerase and the hnRNA Protein Np13p". *Molecular and Cellular Biology.* 20 (2): 604-616.); promotion of translation (Shatkin, A (December 1976). "Capping of eucaryotic mRNAs". *Cell.* 9 (4): 645-653; Banerjee, A K (June 1980). "5'-terminal cap structure in eucaryotic messenger ribonucleic acids". *Microbiol Rev.* 44 (2): 175-205; Sonenberg, Nahum; Gingras, Anne-Claude (April 1998). "The mRNA 5' cap-binding protein eIF4E and control of cell growth". *Current Opinion in Cell Biology.* 10 (2): 268-275; and promotion of 5' proximal intron excision (Konarska et al., (October 1984). "Recognition of cap structure in splicing in vitro of mRNA precursors". *Cell.* 38 (3): 731-736). In eukaryotes, the 5' cap, consists of a guanine nucleotide connected to mRNA via an unusual 5' to 5' triphosphate linkage. This guanosine is methylated on the 7 position directly after capping in vivo by a methyltransferase (Marcotrigiano et al., (June 1997). "Cocrystal Structure of the Messenger RNA 5' Cap-Binding Protein (eIF4E) Bound to 7-methyl-GDP". *Cell.* 89 (6): 951-961.). It is referred to as a 7-methylguanylate cap, abbreviated m7G. In multicellular eukaryotes and some viruses (Fechter et al., (1 May 2005). "Recognition of mRNA cap structures by viral and cellular proteins". Journal of General Virology. 86 (5): 1239-1249.), further modifications exist, including the methylation of the 2' hydroxy-groups of the first 2 ribose sugars of the 5' end of the mRNA. cap-1 has a methylated 2'-hydroxy group on the first ribose sugar, while cap-2 has methylated 2'-hydroxy groups on the first two ribose sugars, shown on the right. The 5' cap is chemically similar to the 3' end of an RNA molecule (the 5' carbon of the cap ribose is bonded, and the 3' unbonded). This provides significant resistance to 5' exonucleases. In some embodiments, the 5' cap is a viral 5' cap. In some embodiments, the viral 5' cap is a clover-leaf. The Enterovirus 5' cloverleaf cis-acting replication element is an RNA element found in the 5' UTR of Enterovirus genomes. The element has a cloverleaf like secondary structure and is known to be a multifunctional cis-acting replication element (CRE), required for the initiation of negative strand RNA synthesis. In addition, 5' cloverleaf may function like a 5' cap and protects viral RNA from rapid degradation by cellular nucleases. In one example, the clover-leaf is derived from poliovirus (Kempf and Barton, *Journal of virology,* 2008, Poly(rC) Binding Proteins and the 5' Cloverleaf of Uncapped Poliovirus mRNA Function during De Novo Assembly of Polysomes). Exemplary nucleotide sequence for poliovirus 5' clover-leaf is set for in SEQ ID NO: 3:

```
                                            (SEQ ID NO: 3)
TTAAAACAGCTCTGGGGTTGTACCCACCCCAGAGGCCCACGTGGCGG

CTAGTACTCCGGTATTGCGGTACCCTTGTACGCCTGTTTTA.
```

Additionally, in some embodiments, the protein coding cassette comprises a 3' cap. In some embodiments, the 3' cap is a poly A tail. Polyadenylation is the addition of a poly A tail to the 3' of a messenger RNA. The poly A tail consists of multiple adenosine monophosphates. In eukaryotes, polyadenylation is part of the process that produces mature messenger RNA (mRNA) for translation. The poly A tail is important for the nuclear export, translation, and stability of mRNA. In some embodiments, the 3' polyadenylation of the protein coding cassette is a poly A tail. In other embodiments, the 3' polyadenylation of the protein coding cassette is a poly A tail mimic. A poly A tail mimic, as used herein, refers to a nucleotide structure that functionally mimics a poly A tail. In some embodiments, the poly A tail mimic is a triplex. A triplex, as used herein, refers to a bipartite triple helix that sequesters the 3' end of the RNA within a U•A-U triple, conferring resistance to rapid RNA decay. In some embodiments, the triplex is derived from metastasis associated lung adenocarcinoma transcript 1 long non-coding RNA (MALAT1 lnc-RNA), Long noncoding RNAs (lncRNAs) function in myriad cellular processes and are associated with various disease states, including cancer. Human metastasis-associated lung adenocarcinoma transcript 1 (MALAT1) is an abundant, ~8-kb lncRNA that is upregulated in multiple cancers. High nuclear levels of MALAT1, with a half-life up to 15 h, promote tumor growth by affecting proliferation, invasion and metastasis, processes associated with altered gene expression in lung cancer. The enhancement of oncogenic processes by MALAT1 in colorectal cancer cells has been localized to a ~1500-nucleotide (nt) fragment near the 3' end (nts 6918-8441)5. A 3' triplex structure is shown to confer stability of the MALAT1 lncRNA (Brown et al., Nat Struct Mol Biol. 2014 July; 21(7): 633-640). Exemplary nucleotide sequence of MALAT1 lncRNA triplex is set forth in SEQ ID NO: 1.

Additionally, in some embodiments, the protein coding cassette comprises a translation initiation site. In eukaryotic translation, initiation typically occurs at the 5' end of mRNA molecules, since 5' cap recognition is required for the assembly of the initiation complex. In some embodiments, the translation initiation site is an internal ribosome entry sites. An internal ribosome entry site (IRES), is an RNA element that allows for translation initiation in a cap-independent manner, as part of the process of protein synthesis. IRES are described as distinct regions of RNA molecules that are able to recruit the eukaryotic ribosome to the rnRNA, known as cap-independent translation. Exemplary RES nucleotide sequence is set forth in SEQ ID NO: 4:

```
                                        (SEQ ID NO: 4)
AGTTCAATAGAAGGGGGTACAAACCAGTACCACCACGAACAAGCACT

TCTGTTTCCCCGGTGATGTCGTATAGACTGCTTGCGTGGTTGAAAGC

GACGGATCCGTTATCCGCTTATGTACTTCGAGAAGCCCAGTACCACC

TCGGAATCTTCGATGCGTTGCGCTCAGCACTCAACCCCAGAGTGTAG

CTTAGGCTGATGAGTCTGGACATCCCTCACCGGTGACGGTGGTCCAG

GCTGCGTTGGCGGCCTACCTATGGCTAACGCCATGGGACGCTAGTTG

TGAACAAGGTGTGAAGAGCCTATTGAGCTACATAAGAATCCTCCGGC

CCCTGAATGCGGCTAATCCCAACCTCGGAGCAGGTGGTCACAAACCA

GTGATTGGCCTGTCGTAACGCGCAAGTCCGTGGCGGAACCGACTACT

TTGGGTGTCCGTGTTTCCTTTTATTTTATTGTGGCTGCTTATGGTGA

CAATCACAGATTGTTATCATAAAGCGA.
```

Additionally, in some embodiments, the protein coding cassette further comprises a first RNA cleavage sites and a second RNA cleavage sites. RNA cleavage sites are included to release the post PAS-RNA from the mRNA of the upstream gene. In some embodiments, the RNA cleavage sites can be nuclease sites. in other embodiments, the RNA cleavage sites are RNA self-cleavage sites. In some embodiments, the RNA self-cleavage sites are small self-cleaving ribozymes. Small self-cleaving ribozymes refer to catalytic RNA structure capable of self-cleavage. They range between 50 and 150 nucleotides in length and are broadly distributed in genomes of organisms from many phyla. Non-limiting examples of small self-cleaving ribozymes are the hammerhead (Prody et al. 1986), hairpin (Buzayan et al. 1986a), hepatitis delta virus (HDV) (Sharmeen et al. 1988), Varkud satellite (VS) (Saville and Collins, 1990), and glmS (Winkler et al. 2004) ribozymes. Any of the ribozymes can be used to flank the post-PAS RNA coding sequence. The first self-cleavage sites and the second self-cleavage sites can be same or different. In some embodiments, the first RNA self-cleavage site is a hepatitis delta, virus (HDV) ribozyme. In some embodiments, the second RNA self-cleavage site is a hammerhead (HH) ribozyme. Exemplary nucleic acid sequence for HDV ribozyme is set forth in SEQ ID NO: 5:

```
                                        (SEQ ID NO: 5)
GGCCGGCATGGTCCCAGCCTCCTCGCTGGCGCCGGCTGGGCAACATG

CTTCGGCATGGCGAATGGGAC.
```

Exemplary nucleic acid sequence for HH ribozyme is set forth in SEQ ID NO: 6:
GGGGACCTGATGAGTCCGT-GAGGACGAAACGAGTAAGCTCGTC (SEQ ID NO: 6). Optionally in addition, the protein coding cassette may further comprise an element that enhances gene expression. In some embodiments, the protein coding cassette comprises a Woodchuck Hepatitis Virus (WHP) Posttranscriptional Regulatory Element (WPRE) between the protein coding RNA and the 3' cap. Woodchuck Hepatitis Virus (WHP) Posttranscriptional Regulatory Element (WPRE) is a DNA sequence that, when transcribed, creates a tertiary structure enhancing expression. The sequence is commonly used in molecular biology to increase expression of genes delivered by viral vectors. WPRE is a tripartite regulatory element with gamma, alpha, and beta components. When used in the 3' untranslated region (UTR) of a mammalian expression cassette, it can significantly increase mRNA stability and protein yield (Donello et al., (June 1998). "Woodchuck hepatitis virus contains a tripartite posttranscriptional regulatory element". J. Virol. 72 (6): 5085-92). Exemplary nucleic acid sequence for WPRE is set forth in SEQ ID NO: 7:

```
                                        (SEQ ID NO: 7)
AATCAACCTCTGGATTACAAAATTTGTGAAAGATTGACTGGTATTCT

TAACTATGTTGCTCCTTTTACGCTATGTGGATACGCTGCTTTAATGC

CTTTGTATCATGCTATTGCTTCCCGTATGGCTTTCATTTTCTCCTCC

TTGTATAAATCCTGGTTGCTGTCTCTTTATGAGGAGTTGTGGCCCGT

TGTCAGGCAACGTGGCGTGGTGTGCACTGTGTTTGCTGACGCAACCC

CCACTGGTTGGGGCATTGCCACCACCTGTCAGCTCCTTTCCGGGACT

TTCGCTTTCCCCCTCCCTATTGCCACGGCGGAACTCATCGCCGCCTG

CCTTGCCCGCTGCTGGACAGGGGCTCGGCTGTTGGGCACTGACAATT

CCGTGGTGTTGTCGGGGAAGCTGACGTCCTTTCCATGGCTGCTCGCC

TGTGTTGCCACCTGGATTCTGCGCGGGACGTCCTTCTGCTACGTCCC

TTCGGCCCTCAATCCAGCGGACCTTCCTTCCCGCGGCCTGCTGCCGG

CTCTGCGGCCTCTTCCGCGTCTTCGCCTTCGCCCTCAGACGAGTCGG

ATCTCCCTTTGGGCCGCCTCCCCGCCTGTTTCGCCTCGGCGTCCGGT

CCGTGTTGCTTGGTCTTCACCTGTGCAGACTTGCGAACCATGGATTC.
```

An exemplary protein coding cassette, from 5' to 3', may comprise: a HDV ribozyme, a clover-leaf, an internal ribosome entry site (IRES), the protein coding RNA of interest, a WPRE, a triplex, and an HH ribozyme. Any of the element in the exemplary protein coding cassette can be substituted with other regulatory elements with similar functions. Any of the protein coding cassette provided herein, may further comprise other regulatory elements for other functions.

The post-PAS RNA, as provided herein, may comprise one or more protein coding cassettes, as described herein. In some embodiments, the post-PAS RNA comprises 1, 2, 3, 4, 5, 6, 7, 8, 9, 10 or more protein cassettes, as described herein.

(ii) Post-Poly a RNA for Expression of a Non-Coding RNA

Other aspects of the present disclosure relate to engineered nucleic acid, encoding a post-PAS RNA comprises a non-coding RNA. A non-coding RNA (ncRNA) is a functional RNA molecule that is transcribed from DNA but riot translated into proteins. Non-limiting examples of ncRNAs include micro-RNA (miRNA), small interfering RNA (siRNA), piwi-interacting RNA (piRNA), long non-coding RNA (lncRNA) and guild. RNA (gRNA). In general, ncRNAs function to regulate gene expression at the transcriptional and post-transcriptional level. miRNA, piRNA and lncRNA play a role in heterochromatin formation, histone modification, DNA methylation targeting, and gene silencing. The gRNA is a short synthetic RNA composed of a scaffold sequence necessary for Cas-binding and a user-defined ~20 nucleotide spacer that defines the genomic target site. In some embodiments, the post-PAS RNA comprises an RNA for expressing one or more pri-miRNA. In other embodiments, the post-PAS RNA comprises an RNA for expressing one or more gRNA.

—miRNA

In some embodiments, the post-PAS RNA comprises one or more miRNA cassette. A miRNA cassette, as used herein, refers to an expression of a miRNA. In addition to the primary miRNA (pri-miRNA) coding sequence, the miRNA cassette may further comprise regulatory elements of various functions, such as RNA cleavage, RNA splicing, increased RNA stability, nuclear export, transcriptional termination, transcriptional and/or translational regulation or the combination thereof. In some embodiments, the miRNA cassette from 5' to 3' comprises a RNA encoding a primary micro-RNA (pri-mRNA).

A miRNA refers to a class of small noncoding RNAs of ~22nt in length which are involved in the regulation of gene expression at the posttranscriptional level by degrading their target mRNAs and/or inhibiting their translation. miRNAs can be described as "multivalent," with one miRNA able to target multiple genes, thus regulating the expression of several proteins. They were demonstrated to act on several key cellular processes, such as cell differentiation, cell cycle progression, and apoptosis. miRNAs function via base-pairing with complementary sequences within mRNA molecules. As a result, these mRNA molecules are silenced, by one or more of the following processes: (1) Cleavage of the mRNA strand into two pieces, (2) Destabilization of the mRNA through shortening of its poly(A) tail, and (3) Less efficient translation of the mRNA into proteins by ribosomes.

miRNA genes are usually transcribed by RNA polymerase II (Pol II). The miRNA gene is transcribed to generate a primary microRNA (pri-miRNA) precursor molecule that undergoes nuclear cleavage to form a precursor microRNA (pre-miRNA). The pre-miRNA is cleaved in the cytoplasm to create a microRNA. duplex containing the mature miRNA. The duplex unwinds and the mature miRNA assembles into RISC. The miRNA base-pairs with target mRNA to direct gene silencing via mRNA cleavage or translation repression based on the level of complementarity between the miRNA and the mRNA target.

As provided herein, the miRNA cassette can encode any miRNA of interest. In some embodiments, the miRNA cassette comprises the RNA sequence for any pri-miRNA of interest. Once transcribed, the pri-miRNA can be processed into mature miRNA. Non-limiting exemplary miRNA can be produced by the miRNA cassette can be found in miR-base (mirbase.org/). In some embodiments, the miRNA is miR-FF4. Exemplary nucleic acid encoding pri-miR-FF4 is set forth in SEQ ID NO: 8:

```
(SEQ ID NO: 8)
TAAAGCTTGAGGTGAGTATGTGCTCGCTTCGGCAGCACATATACTATG

TTGAATGAGGCTTCAGTACTTTACAGAATCGTTGCCTGCACATCTTGG

AAACACTTGCTGGGATTACTTCTTCAGGTTAACCCAACAGAAGGCTCG

AGTGCTGTTGACAGTGAGCGCCGCTTGAAGTTTTTAATTAAATAGTGA

AGCCACAGATGTATTTAATTAAAGACTTCAAGCGGGTGCCTACTGCCT

CGGAGAATTCAAGGGCTACTTTAGGAGCAATTATCTTGTTTACTAAAA

CTGAATACCTTGCTATCTCTTTGATACATTTTTACAAAGCTGAATTAA

AATGGTATAAATTAAATCACTTTTTTCAATTGTTTCCTTTTTTTTCCT

CAGGGTACCCAGCTTTCTTGTACAAAGTGGTACGCG.
```

In some embodiments, the miRNA cassette from 5' to 3' comprises, a first RNA cleavage site (e.g., ribozyme), the RNA encoding pri-miRNA, and a second RNA cleavage site (e.g., ribozyme).

RNA cleavage sites are included to release the post PAS-RNA from the mRNA of the upstream gene.). In some embodiments, the RNA cleavage sites can be nuclease sites. In other embodiments, the RNA cleavage sites are RNA self-cleavage sites. In some embodiments, the RNA self-cleavage sites are small self-cleaving ribozymes. Small self-cleaving ribozymes refer to catalytic RNA structure capable of self-cleavage. They range between 50 and 150 nucleotides in length and are broadly distributed in genomes of organisms from many phyla. Non-limiting examples of small self-cleaving ribozymes are the hammerhead (Prody et al. 1986), hairpin (Buzayan et al. 1986a), hepatitis delta virus (HDV) (Shartneen et al. 1988), Varkud satellite (VS) (Saville and Collins, 1990), and glmS (Winkler et al. 2004) ribozymes. Any of the ribozymes can be used to flank the post-PAS RNA coding sequence. The first self-cleavage sites and the second self-cleavage sites can be same or different. In some embodiments, the first RNA self-cleavage site is a hepatitis delta virus (HDV) ribozyme. In some embodiments, the second RNA self-cleavage site is a hammerhead (HH) ribozyme. In other embodiments, the miRNA cassette from 5' to 3' comprises, a third RNA cleavage site, a first RNA cleavage site (e.g., ribozyme), the RNA encoding pri-miRNA, and a second RNA cleavage site (e.g., ribozyme). In some embodiments, the RNA cleavage sites can be nuclease sites. In other embodiments, the RNA cleavage sites are RNA self-cleavage sites. In other embodiments, the RNA self-cleavage sites are small self-cleaving ribozymes. In some embodiments, the third RNA self-cleavage site is a hepatitis delta virus (HDV) ribozyme, the first RNA self-cleavage site is a hammerhead (HH) ribozyme and the second third RNA self-cleavage site is a hepatitis delta virus (HDV) ribozyme. In some embodiments, the ribozymes can be wild type ribozyme. In other embodiments, the ribozymes can be mutant ribozyme. In some embodiments, the first RNA self-cleavage site is a hammerhead_56 ribozyme (HHR_56 ribozyme), the second RNA self-cleavage site is a hepatitis delta virus_84 ribozyme (HDV_84 ribozyme) and the third RNA self-cleavage site is a hepatitis delta virus_140 ribozyme ribozyme).

The miRNA cassette described herein, may further comprise a miR-E element at the 3' end of the pri-miRNA coding sequence. A miR-E element, as described herein, refers to a conserved element 3' of the basal stem as critically required for optimal miRNA processing (Fellmann et al., *Cell Rep.* 2013 Dec. 26;5(6):1704-13). miR-E increases mature miRNA levels and knockdown efficacy.

The post-PAS RNA, as provided herein, may comprise one or more miRNA cassettes as described herein. In some embodiments, the post-PAS RNA comprises 1, 2, 3, 4, 5, 6, 7, 8, 9, 10 or more miRNA cassettes, as described herein.

—gRNA

In some embodiments, the post-PAS RNA comprises one or more gRNA cassette. A gRNA cassette, as used herein, refers to an expression of a gRNA. In addition to the gRNA coding sequence, the gRNA cassette may further comprise regulatory elements of various functions, such as RNA cleavage, RNA splicing, increased RNA stability, nuclear export, transcriptional termination, transcriptional and/or translational regulation or the combination thereof.

A guide RNA (gRNA), as used herein, refers to a single guide RNA (sgRNA) that comprises both the protospacer sequence and the scaffold RNA sequence for to aid in recruiting the endonuclease to the target site. A guide RNA helps direct an endonuclease to a target site, which typically contains a nucleotide sequence that is complementary (partially or completely) to the nRNA or a portion thereof. A guide RNA can be used to guide a nucleic acid programmable DNA binding protein (e.g., Cas9) to a specific nucleic acid sequence. For example, a Cas9 protein can associate with a guide RNA that guides the Cas9 protein to a specific DNA sequence that has complementary to the guide RNA. Examples of nucleic acid programmable DNA binding proteins include, without limitation, Cas9 (e.g., dCas9 and nCas9), CasX, CasY, Cpf1, C2c1, C2c2, C2C3, and Argonaute. Other nucleic acid programmable DNA binding proteins are also within the scope of this disclosure, though they may not be specifically listed in this disclosure. In some embodiments, the Cas9 is a Cas9 domain, for example a nuclease active Cas9, a Cas9 nickase (nCas9), or a nuclease inactive Cas9 (dCas9). In other embodiments, the Cas9 is a Cas9 chimera protein. The Cas9 chimera protein can be a fusion protein between a Cas9 domain described herein and other functional proteins, such as transcription factors, deaminases, etc.

In some embodiments, the gRNA cassette from 5' to 3' comprises, a first RNA cleavage site (e.g., ribozyme), the RNA encoding gRNA, and a second RNA cleavage site (e.g., ribozyme).

RNA cleavage sites are included to release the post PAS-RNA from the RNA of the upstream gene.). In some embodiments, the RNA cleavage sites can be nuclease sites. In other embodiments, the RNA cleavage sites are RNA self-cleavage sites. In some embodiments, the RNA self-cleavage sites are small self-cleaving ribozymes. Small self-cleaving ribozymes refer to catalytic RNA structure capable of self-cleavage. They range between 50 and 150 nucleotides in length and are broadly distributed in genomes of organisms from many phyla. Non-limiting examples of small self-cleaving ribozymes are the hammerhead (Prody et al. 1986), hairpin (Buzayan et al. 1986a), hepatitis delta virus (HDV) (Sharmeen et al. 1988), Varkud satellite (VS) (Saville and Collins, 1990), and glmS (Winkler et al. 2004) ribozymes. Any of the ribozymes can be used to flank the post-PAS RNA coding sequence. The first self-cleavage sites and the second self-cleavage sites can be same or different. In some embodiments, the first RNA self-cleavage site is a hepatitis delta virus (HDV) ribozyme. In some embodiments, the second RNA self-cleavage site is a hammerhead (HH) ribozyme. In other embodiments, the gRNA cassette from 5' to 3' comprises, a third RNA cleavage site, a first RNA cleavage site (e.g., ribozyme), the RNA encoding gRNA, and a second RNA cleavage site (e.g., ribozyme). In some embodiments, the RNA cleavage sites can be nuclease sites. In other embodiments, the RNA cleavage sites are RNA self-cleavage sites. In other embodiments, the RNA self-cleavage sites are small self-cleaving ribozymes. In some embodiments, the third RNA self-cleavage site is a hepatitis delta virus (HDV) ribozyme, the first RNA self-cleavage site is a hammerhead (HH) ribozyme and the second third RNA self-cleavage site is a hepatitis delta virus (HDV) ribozyme. In some embodiments, the ribozymes can be wild type ribozyme. In other embodiments, the ribozymes can be mutant ribozyme. In some embodiments, the first RNA self-cleavage site is a hammerhead_56 ribozyme (HHR_56 ribozyme), the second RNA self-cleavage site is a hepatitis delta virus_84 ribozyme (HDV_84 ribozyme) and the third RNA self-cleavage site is a hepatitis delta virus_140 ribozyme (HDV_140 ribozyme).

The post-PAS RNA, as provided herein, may comprise one or more gRNA cassettes as described herein. In some embodiments, the post-PAS RNA comprises 1, 2, 3, 4. 5, 6, 7, 8, 9, 10 or more gRNA cassettes, as described herein.

In some embodiments, when the first RNA cleavage site is a HDV ribozyme 5' to the non-coding RNA expression cassette (e.g., miRNA cassette or gRNA cassette). Due to the Pol III promoter activity of HDV ribozyme, it can potentially drive the expression of the non-coding RNA (e.g., miRNA or gRNA) independent of the expression of the upstream gene. In some embodiments, a Pol III terminator can be placed between the HDV and the non-coding RNA expression cassette. Such placement can effectively prevent HDV from driving the expression of the gRNA independent of the upstream gene.

An exemplary nucleic acid sequence for Pol III terminator is set forth in SEQ ID NO: 12:

CTCACCGAGGACACTGGGGGCAAGGGGGACCT-GATGAGCTTTTTTGCGAAACGAGTAAG CTCGTC (iv) Vectors and Cells Further provided herein are vectors that comprise one or more engineered nucleic acids described in the present disclosure. A vector includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some instances, the vector is a plasmid, a RNA replicon or a viral vector. As used herein, the term "RNA replicon" refers to a self-replicating genetic element comprised a RNA that replicates from one origin of replication. In some embodiments, the self-amplifying replicon RNA is derived from an alphavirus. In some embodiments, useful vectors are contemplated to be those vectors in which the nucleic acid segment to be transcribed is positioned under the transcriptional control of a promoter. The term "expression vector or construct" means any type of genetic construct containing a nucleic acid in which part or all of the nucleic acid encoding sequence is capable of being transcribed. In some embodiments, expression includes transcription of the engineered nucleic acid, for example, to generate a biologically-active protein encoded by the transgene and functional RNA (e.g., protein coding RNA, miRNA and guide RNA).

Cells comprising the engineered nucleic acids, expression cassettes and/or vectors are within the scope of the disclosure. The cell can be any cell suitable for producing the transgene. In some embodiments, the cells are prokaryotic cells. In other embodiments, the cells are eukaryotic cells. In some embodiments, the cells are mammalian cells. In other examples, the cells are human cells or non-human cells. Non-limiting example for non-human cells can be non-human mammalian cells, plant cells, insect cells, bacterial cells or fungi cells.

In some embodiments, the cells comprise the engineered nucleic acid and/or the vectors described herein epigenetically. The engineered nucleic acid and/or the vectors can be delivered to the cells by methods known in the art.

In other embodiments, the engineered nucleic acid described herein is integrated into the genomic DNA of the cell. Genomic integration of the present engineered nucleic acid can be done by methods known in the art. In some embodiments, the genomic integration of the present engineered nucleic acid can be achieved by viral transduction (e.g., including but not limited to lentiviral vectors, retroviral vectors, PiggyBac transposon vector and Sleeping-Beauty transposon vector) and introduced into host immune cells using conventional recombinant technology. Sambrook et al., Molecular Cloning, A Laboratory Manual, 3rd Ed., Cold Spring Harbor Laboratory Press. Viral transduction mediated genomic integration results in integration in random genomic locus.

In other embodiments, the engineered nucleic acid described herein is integrated in the terminator region of an endogenous gene. In some embodiments, the endogenous gene is a housekeeping gene. Housekeeping genes are typically constitutive genes that are required for the maintenance of basic cellular function, and are expressed in all cells of an organism under normal and patho-physiological conditions. Non-limiting examples of housekeeping genes are: Glyceraldehyde 3-phosphate dehydrogenase (GAPDH) gene, a Macrophage Migration Inhibitory Factor (MIF) gene, a Small Nuclear Ribonucleoprotein D2 Polypeptide (SNRPD2) gene, Non-POU Domain-Containing Octamer-Binding Protein (NONO), phosphoglycerate kinase 1 (PGK1), or Peptidylprolyl Isomerase H (PPIH) or an Eukaryotic Translation Elongation Factor 1 Alpha 1 (EEF1A1) gene. More exemplary housekeeping genes are shown in Table 1. Other housekeeping genes not mentioned are also within the scope of the present disclosure.

TABLE 1

Non-limiting examples of housekeeping genes

| Gene symbol | Gene description |
| --- | --- |
| ACTG1 | Actin γ 1 |
| AMZ2 | Archaelysin family metallopeptidase 2 |
| AP2M1 | Adaptor-related protein complex, 2 μ1 subunit |
| C14orf166 | Chromosome 14 open reading frame 166 |
| CNIH1 | Cornichon family AMPA receptor auxiliary protein 1 |
| CRELD2 | Cysteine rich with EGF like domains 2 |
| ECHS1 | Enoyl-CoA hydratase, short chain 1 |
| EEF1G | Eukaryotic translation elongation factor 1γ |
| EIF4A3 | Eukaryotic translation initiation factor 4A3 |
| EPCAM | Epithelial cell adhesion molecule |
| FAM96A | Family with sequence similarity 96 member A |

TABLE 1-continued

Non-limiting examples of housekeeping genes

| Gene symbol | Gene description |
| --- | --- |
| FAM96B | Family with sequence similarity 96 member B |
| FIS1 | Fission, mitochondrial 1 |
| GABARAP | GABA type A receptor-associated protein |
| GABARAPL2 | GABA type A receptor associated protein like 2 |
| GANAB | Glucosidase II α subunit |
| GPX1 | Glutathione peroxidase 1 |
| GSTO1 | Glutathione S-transferase ω1 |
| GTF3A | General transcription factor IIIA |
| HDGF | Heparin binding growth factor |
| HEBP1 | Heme binding protein 1 |
| HEBP2 | Heme binding protein 2 |
| HIST1H2BK | Histone cluster 1 H2B family member k |
| IFI27 | Interferon α-inducible protein 27 |
| JTB | Jumping translocation breakpoint |
| LAMTOR5 | Late endosomal/lysosomal adaptor, MAPK and MTOR activator 5 |
| MB | Myoglobin |
| MIF | Macrophage migration inhibitory factor (glycosylation-inhibiting factor) |
| MRFAP1 | Morf4 family associated protein 1 |
| MRPL18 | Mitochondrial ribosomal protein L18 |
| MRPS24 | Mitochondrial ribosomal protein S24 |
| NDUFA3 | NADH: ubiquinone oxidoreductase subunit A3 |
| NDUFB1 | NADH: ubiquinone oxidoreductase subunit B1 |
| NDUFB4 | NADH: ubiquinone oxidoreductase subunit B4 |
| NDUFB11 | NADH: ubiquinone oxidoreductase subunit B11 |
| NDUFS3 | NADH: ubiquinone oxidoreductase core subunit S3 |
| NELFCD | Negative elongation factor complex member C/D |
| NOP10 | NOP10 ribonucleoprotein |
| PGAM1 | Phosphoglycerate mutase 1 |
| POLR2H | RNA polymerase II subunit H |
| POLR2I | RNA polymerase II subunit I |
| POM121C | POM121 transmembrane nucleoporin C |
| POMP | Proteasome maturation protein |
| PRDX1 | Peroxiredoxin 1 |
| PSMC1 | Proteasome 26S subunit, ATPase 1 |
| RBX1 | Ring-box 1 |
| RNASEK | Ribonuclease K |
| RNF181 | Ring finger protein 181 |
| RPL6 | Ribosomal protein L6 |
| RPL8 | Ribosomal protein L8 |
| RPL41 | Ribosomal protein L41 |
| RPLP0 | Ribosomal protein lateral stalk subunit P0 |
| RPS18 | Ribosomal protein S18 |
| RPS25 | Ribosomal protein S25 |
| RPS27 | Ribosomal protein S27 |
| RPS29 | Ribosomal protein S29 |
| RPSA | Ribosomal protein SA |
| RRAGA | Ras related GTP binding A |
| SLC25A3 | Solute carrier family 25 member 3 |
| SNRPD2 | Small nuclear ribonucleoprotein D2 polypeptide |
| SOD1 | Superoxide dismutase 1 |
| TBCB | Tubulin folding cofactor B |
| TERF2IP | TERF2 interacting protein |
| TMEM147 | Transmembrane protein 147 |
| TOMM5 | Translocase of outer mitochondrial membrane 5 |
| TPT1 | Tumor protein, translationally-controlled 1 |
| TUBA1B | Tubulin α1b |
| YTHDF1 | YTH N6-methyladenosine RNA binding protein 1 |

In other examples, the endogenous gene is not a housekeeping gene. Expression of a non-housekeeping gene may be constitutive, inducible or tissue specific. The selection of terminator region of the gene can be based on the intended purpose of the engineered post-PAS RNA.

Targeted genomic integration of the engineered nucleic acid described herein can be achieved by methods known in the art. Such genomic integration methods are generally classified based on the type of endonuclease that is involved in generating double stranded breaks in the target nucleic acid. Examples include, but are not limited to, Clustered Regularly Interspaced Short Palindromic Repeats (CRISPR)/endonuclease systems, transcription activator-like effector-based nuclease (TALEN), zinc finger nucleases (ZEN), endonucleases (e.g., ARC homing endonucleases), meganucleases (e.g., mega-TALs), or a combination thereof. In some embodiments, the genomic integration of the engineered nucleic acid is achieved by CRISPR/Cas mediated genetic modification. Cleavage of a target region may comprise cleaving one or two strands at the location of the target sequence (e.g., the terminator region of an endogenous gene by an endonuclease (e.g., Cas9), followed by repairing the cleaved target polynucleotide by homologous recombination with an exogenous template encoding the engineered nucleic acid described herein, leading to insertion, or substitution of one or more nucleotides of the target nucleotide sequence (e.g., the terminator region of an endogenous gene).

Also provided herein are organisms comprising the engineered nucleic acid, vector and/or cells described herein. Exemplary organisms can be prokaryotic organisms or eukaryotic organisms. In some embodiments, the prokaryotic organism is a bacteria. In some embodiments, the eukaryotic organism is an animal, a plant, or a fungus. In some embodiments, the eukaryotic organism is an animal. In some further examples, the animal is a non-human animal. Non-limiting examples of non-human animals are mice, chickens, goats, rabbits, pigs, donkeys, cows, or camels.

II. Application of Post-Poly A Signal RNA

Other aspects of the present disclosure, at least in part, is based on expressing various exogenous functional RNA (e.g., protein coding RNA and non-coding RNA) encoded by the engineered nucleic acid described herein in the terminator region (e.g., post-PAS RNA) of an upstream gene (e.g., endogenous gene and/or a transgene), so that the post-PAS RNA can produce molecules with various cellular function (e.g., transcriptional regulation, genetic sensor and silencing of target endogenous/exogenous genes) while avoiding certain unwanted drawbacks related to an exogenous gene circuit (e.g., epigenetic silencing). The application of the engineered nucleic acid described herein is not limited to the examples described in the present disclosure.

One aspect of the application using the engineered nucleic acid described herein is to reducing epigenetic silencing of a synthetic gene circuit. In some embodiments, the engineered nucleic acid comprises a synthetic gene circuit. A synthetic (gene circuit, as used herein, refers to a combination of regulatory (e.g., promoter, enhancer and cleavage sites) and/or coding DNA (e.g., protein coding DNA, miRNA coding DNA and gRNA coding DNA) that can be introduced into a host cell for various functions. Gene silencing that occur when a synthetic circuits is introduced into an endogenous network is a long standing problem in synthetic biology and genetic engineering. Gene silencing is especially problematic for circuits that are integrated into a mammalian genome and the problem is worse for large and/or complex genetic circuits. One of the attempt to reduce epigenetic gene silencing is to directly fuse the gene circuit with the endogenous gene. However, such approach suffers from other issues. For example, direct fusion of the target gene of interest using a 2A tag or other means may alter the wild-type expression level and does not allow for insertion of important signaling peptides in the target gene (e.g. for localization or secretion). The present disclosure provides a novel method that provide the ability to express an exogenous gene circuit containing engineered nucleic acid described herein, while addressing the long-standing problem of how to provide sustained functioning circuits without epigenetic silencing that plagues many synthetic integrated circuits. Embedded synthetic biology circuits both respond to endogenous signals and provide new control of other endogenous signals without being silenced. Specific genomic loci that are not prone to epigenetic silencing can be targeted (e.g., terminator region of a housekeeping gene). In some embodiments, the method for reducing epigenetic silencing of an exogenous gene circuit in a cell is replacing or embedding into a terminator region of a target (endogenous) gene of the cell with the engineered nucleic acid described herein.

Alternatively or in addition, the present disclosure provides a method for transcriptional regulation of an exogenous gene circuit at the same level of the upstream endogenous gene. One other disadvantage of introducing an exogenous gene operably linked to an exogenous promoter is limited to the strength of the exogenous promoter (e.g., too weak or too strong) and/or transcriptional regulation. However, many applications necessitate an expression levels of an exogenous gene close to endogenous gene expression level and to be regulated the same as an endogenous gene. By placing the engineered nucleic acid as described herein in the terminator region of an upstream gene (e.g., endogenous gene and/or a transgene), it shares transcriptional and post transcriptional regulation with the upstream gene. Also, the expression of the upstream gene is not affected.

Alternatively or in addition, the present disclosure provides a method for reporting the expression of an upstream gene (e.g., an endogenous gene or a transgene). In some embodiments, the engineered nucleic acid placed at the terminator region of the upstream gene encodes for a reporter. Non-limiting examples of a reporter are: fluorescent proteins (e.g., GFP) or enzymes (e.g., luciferase). The expression of the reporter can be measured by methods known in the art (e.g., flow cytometry). In some embodiments, the successful expression and/or level of reporter (e.g., GFP) is indicative of the successful expression and/or level of the upstream gene.

In addition, the present disclosure provides a method for epigenetic silencing by RNA interference (RNAi). In some embodiments, the engineered nucleic acid comprises a miRNA cassette for expression of a miRNA targeting a gene of interest. In some embodiment, the engineered nucleic acid replaces or is embedded in the terminator region of an upstream gene. The primary miRNA is transcribed with the upstream gene and be processed into the mature miRNA for silencing of the target gene. The production of the miRNA and the silencing of the target gene can be measured by methods know in the art.

In addition, the present disclosure provides a method for genetic modification by CRISPR/Cas9. In some embodiments, the engineered nucleic acid encoding a gRNA targeting a gene of interest replaces or is embedded in the terminator region of an upstream gene. The gRNA will be transcribed with the upstream gene and can guide Cas9 to the target site for intended genetic modification. In some embodiments, the Cas9 protein is delivered to the cell on a vector. In some embodiments, the coding sequence of Cas9 is integrated into the genome of the cell by known methods in the art (e.g., lentiviral transduction). In other embodiments, another engineered nucleic acid encoding Cas9 replaces or is embedded in the terminator region of another upstream gene.

A Cas9 protein can associate with a guide RNA that guides the Cas9 protein to a specific DNA sequence that has complementary to the guide RNA. In some embodiments, the DNA binding protein is a Cas9 domain, for example a nuclease active Cas9, a Cas9 nickase (nCas9), or a nuclease inactive Cas9 (dCas9). Examples of nucleic acid programmable DNA binding proteins include, without limitation, Cas9 (e.g., dCas9 and nCas9), CasX, CasY, Cpf1, C2c1, C2c2, C2C3, and Argonaute. Other nucleic acid programmable DNA binding proteins are also within the scope of this disclosure, though they may not be specifically listed in this disclosure.

In addition, the present disclosure provides methods for input a complex regulatory network into the cell. In some embodiments, a protein coding engineered nucleic acid described herein encodes a regulatory protein (e.g., a transcription factor) replaces or is embedded into the terminator region of an upstream gene. In other embodiments, a nRNA coding engineered nucleic acid described herein encodes one or more gRNA targeting a gene to be regulated (e.g., a transcriptional activation or repression) replaces or is embedded into the terminator region of an upstream gene. In some embodiments, the gRNA coding engineered nucleic acid encodes one or more targets one site. In other embodiments, the gRNA coding engineered nucleic acid encodes gRNAs targeting different sites. Such gRNA can be coupled with a Cas9 chimera protein for regulatory function. A Cas9 chimera protein, as used herein, refers to a fusion protein with (i) a Cas9 domain; (ii) a functional domain (e.g., transcription factors) and (iii) a link between (i) and (ii), such as an amino acid linker.

A Cas9 or Cas9 domain refers to an RNA-guided nuclease comprising a Cas9 protein, or a fragment thereof (e.g., a protein comprising an active, inactive, or partially active DNA cleavage domain of Cas9, and/or the gRNA binding domain of Cas9). A Cas9 nuclease is also referred to sometimes as a cash I nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA. into a single RNA species. See, e.g., Jinek M., Chylinski K., Fonfara I., Hauer M., Doudna J. A., Charpentier E. Science 337:816-821 (2012), the entire contents of which is hereby incorporated by reference. Cas9 recognizes a short motif in the CR1SPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor kNase III." Deltcheva. E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference). Cas9 orthologs have been described in various species, including, but riot Ranted to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type 11 CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase. Additional suitable nuclease-inactive dCas9 domains will be apparent to those of skill in the art based on this disclosure and knowledge in the field, and are within the scope of this disclosure.

In some embodiments, the Cas9 domain is a nuclease dead Cas9 (dCas9). A nuclease-inactivated Cas9 protein may interchangeably be referred to as a "dCas9" protein (for nuclease-"dead" Cas9). Methods for generating a Cas9 protein (or a fragment thereof) having an inactive DNA cleavage domain are known (See, e.g., Jinek et al., Science. 337:816-821(2012); Qi et al., "Repurposing CRISPR as an RNA-Guided Platform for Sequence-Specific Control of Gene Expression" (2013) Cell. 28;152(5):1173-83, the entire contents of each of which are incorporated herein by reference). For example, the DNA cleavage domain of Cas9 is known to include two subdomains, the HNH nuclease subdomain and the RuvC1. subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., Science. 337:816-821 (2012); Qi et al., Cell. 28;152(5):1173-83 (2013)). In some embodiments, proteins comprising Cas9 or fragments thereof are referred to as "Cas9 variants." A Cas9 variant shares homology to Cas9, or a fragment thereof.

A linker, as used herein, refers to a bond (e.g., covalent bond), chemical group, or a molecule linking two molecules or moieties, e.g., two domains of a fusion protein, such as, for example, a nuclease-inactive Cas9 domain and a nucleic acid-editing domain (e.g., an adenosine deaminase). In some embodiments, a linker joins a gRNA binding domain of an RNA-programmable nuclease, including a Cas9 nuclease domain, and the catalytic domain of a nucleic-acid editing protein. In some embodiments, a linker joins a dCas9 and a nucleic-acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

In some embodiments, the functional domain is transcription factors. In one example, the transcription factor is for transcriptional activation. In another example, the transcription factor is for transcriptional inhibition. Other functional protein with regulatory functions of a gene can be linked to the Cas9 domain for various regulatory functions. In some embodiments, the Cas9 chimera protein is delivered to the cell on a vector. In some embodiments, the coding sequence of chimera protein is integrated into the genome of the cell by known methods in the art (e.g., lentiviral transduction). In other embodiments, another engineered nucleic acid encoding chimera. protein replaces or is embedded in the terminator region of another upstream gene. In some embodiments, both the nRNA and the Cas9 chimera are constitutively expressed. In other embodiments, the gRNA is constitutively expressed while the expression of Cas9 chimera is regulated or inducible. Under such condition, regulation of the target gene only occurs when the expression of Cas9 chimera is activated by certain conditions.

In addition, the present disclosure provide a method for directed differentiation of stem cells, the method comprising replacing a terminator region of a stem cell specific gene of the cell with the engineered nucleic acid described herein. A stem cell specific gene, refers to a gene expressed only in stem cells. In some embodiments, the stem cell is an induced pluripotent stem cell, an embryonic stem cell, a tissue-specific stem cell, a mesenchymal stem cell or a hematopoietic stem cell. In some embodiments the stem cell is a human induced pluripotent stem cell. Non-limiting stem cell specific genes include Sox17, Oct4, c-Myc, Sox2, Klf4, Nanog, Sall4, Dax1 Essrb, Tbx3, Tcl1, Rif1, Nac1, Zfp281, SSEA-1, SSEA-4, TRA-1-60, TRA1-81, GDF3, REX1, FGF4, ESG1, DPPA2, DPPA4, hTERT, Otx2, Chordin, p63/TP73L, Pax2. FoxJ3, Pax6, GBX2, SOX1, Nestin, Tubulin, and Noggin. In some embodiments, the stem cell specific gene is Sox17. When the engineered nucleic acid described herein is placed in the terminator region of endogenous Sox17 in stem cells, the expression of Sox17 drives the transcription of the post PAS RNA. In some embodiments, the post PAS RNA encodes a protein capable of directing stem cell differentiation into a specific cell type or tissue. Non-limiting examples of such tissue include pancreas, liver, lung, heart, brain, intestine, eye, muscle, bone, connective tissue, and blood cells. In some embodiments the post PAS RNA encodes a miRNA capable of directing stem cell differentiation into a specific cell type or tissue. In some embodiments, the post PAS RNA encodes a gRNA capable of targeting a gene that can direct stem cell differentiation into a specific cell type or tissue. In some embodiments, when the post PAS RNA encodes a gRNA, a Cas9 fusion protein described herein is also delivered to the stem cell such that the gRNA can guide the Cas9 fusion (e.g., dCas9-VPR transcription factor) for regulation of a gene capable of directing stem cell differentiation. In some embodiments, the stein cells are differentiated into pancreatic organoids. In some embodiments, the pancreas specific gene is Pdx1.

III. (General Techniques)

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F, M. Ausubel, et at, eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Post-PAS RNA for Expression of Protein, rRNA (miRNA) and Guide RNA (gRNA)

To test if different types of non-coding RNA and protein-coding RNA can be successfully transcribed (and translated) from the post poly-A signal RNA (post-PAS RNA), a construct was designed, as shown in FIG. 1. The construct includes from 5' to 3' an abscisic acid (ABA) responsible $P_{phIF}$ promoter, a coding sequence for enhanced yellow fluorescence protein driven by the $P_{phIF}$ promoter and a Sox17 terminator (ENSG00000164736, nucleotide 54,460, 646-54,463,905). The nucleic acid encoding the post-PAS RNA was positioned at variance distance downstream of the PAS (at position 54,460,864-54,460,869). The experiment is done in HEK293 cells using co-transfection of multiple non-integrating and non-replicating plasmids.

Figure 2A:
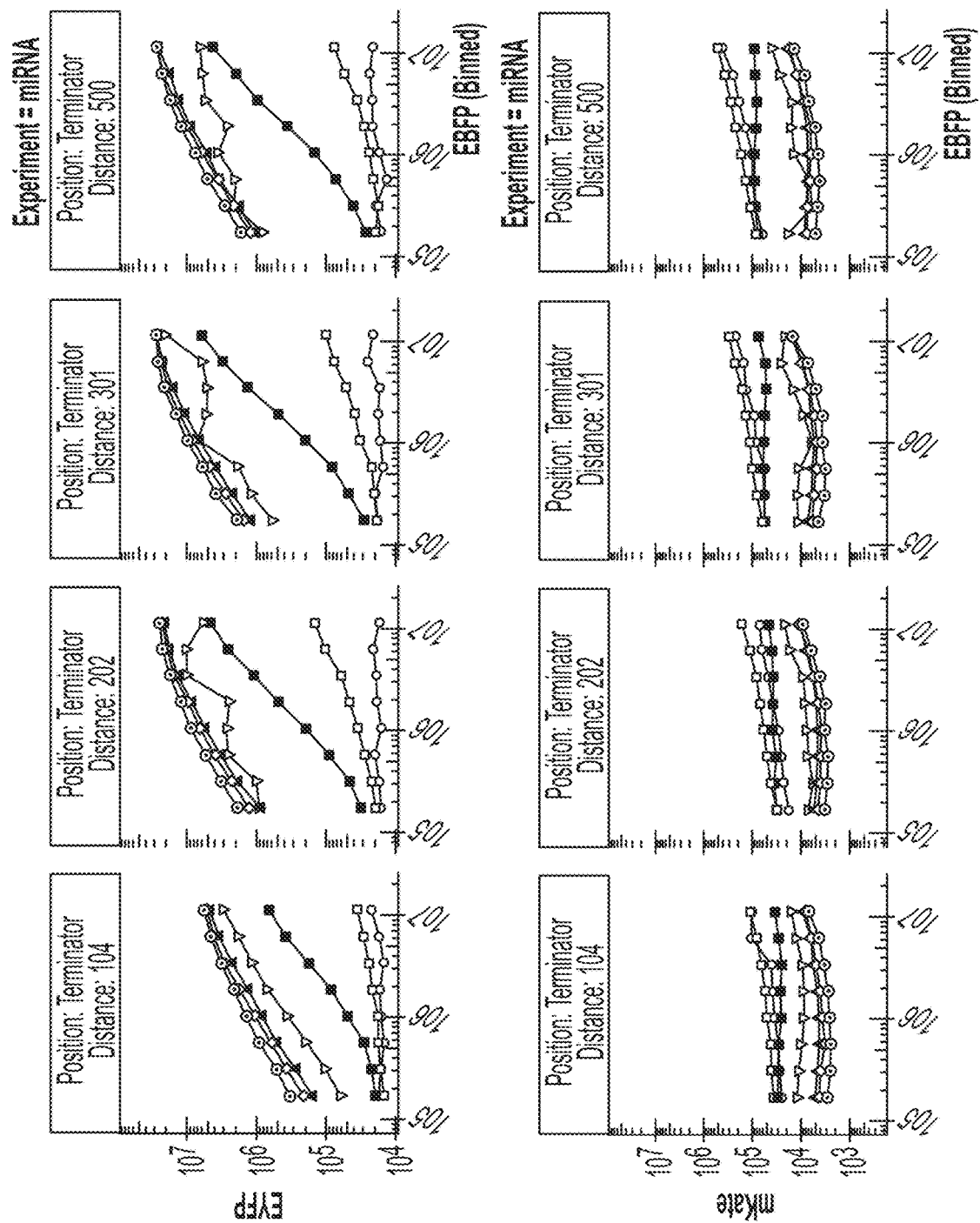
FIGS. 2A-2C show successful expression of miRNA, protein and gRNA using post-PAS RNA in the Sox17 terminator region.
Figure 2A:
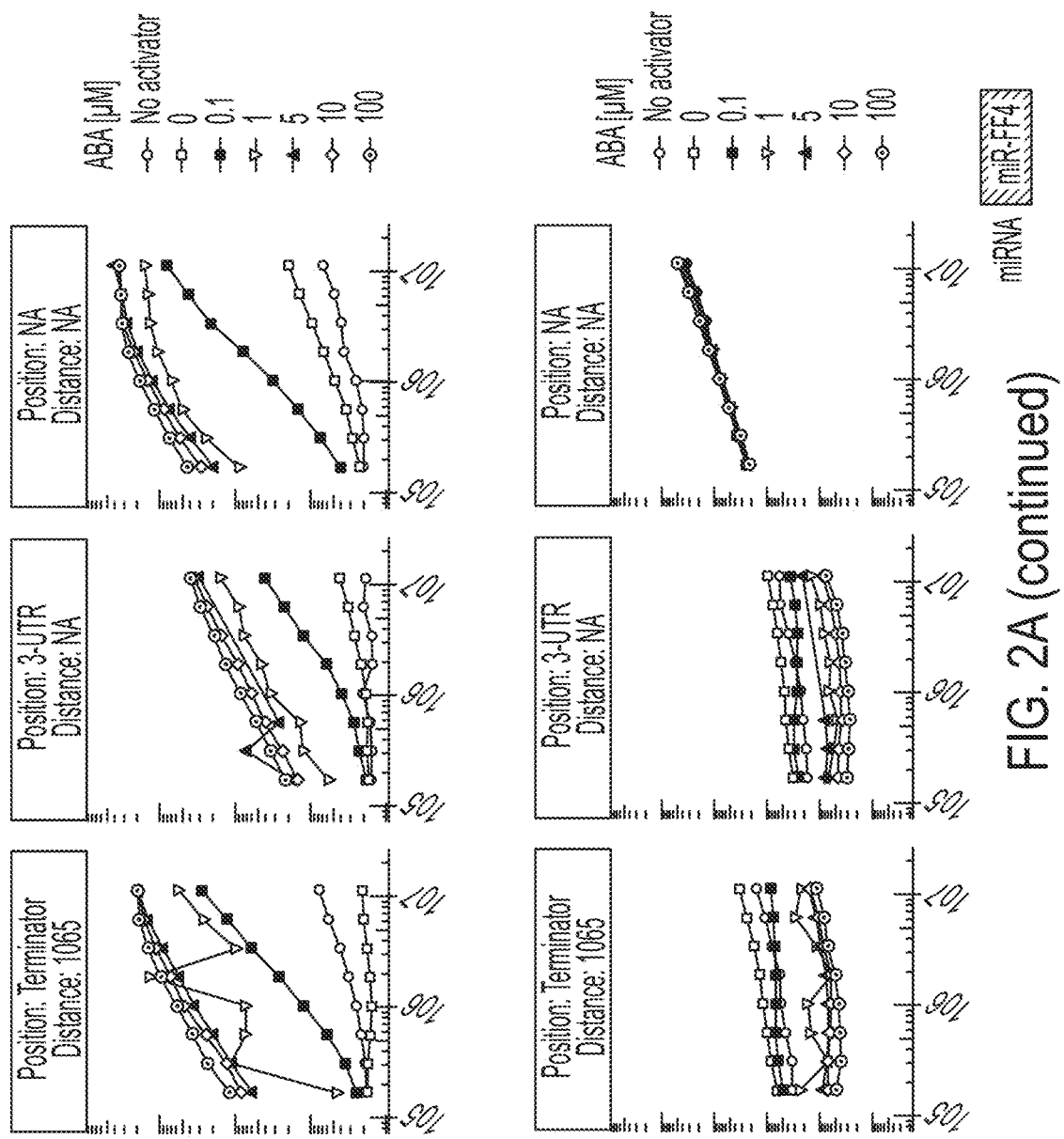
Figure 2B:
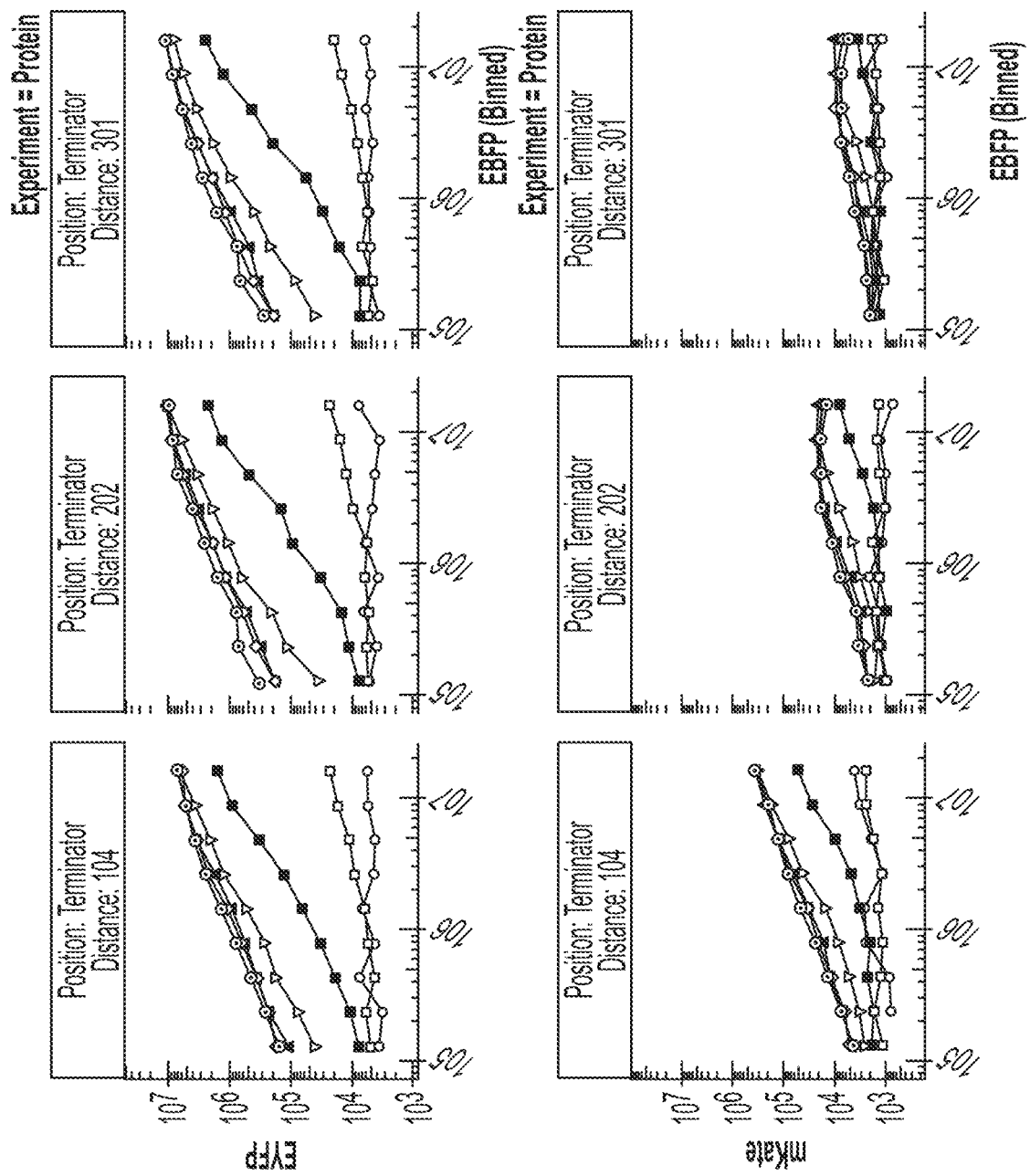
Figure 2B:
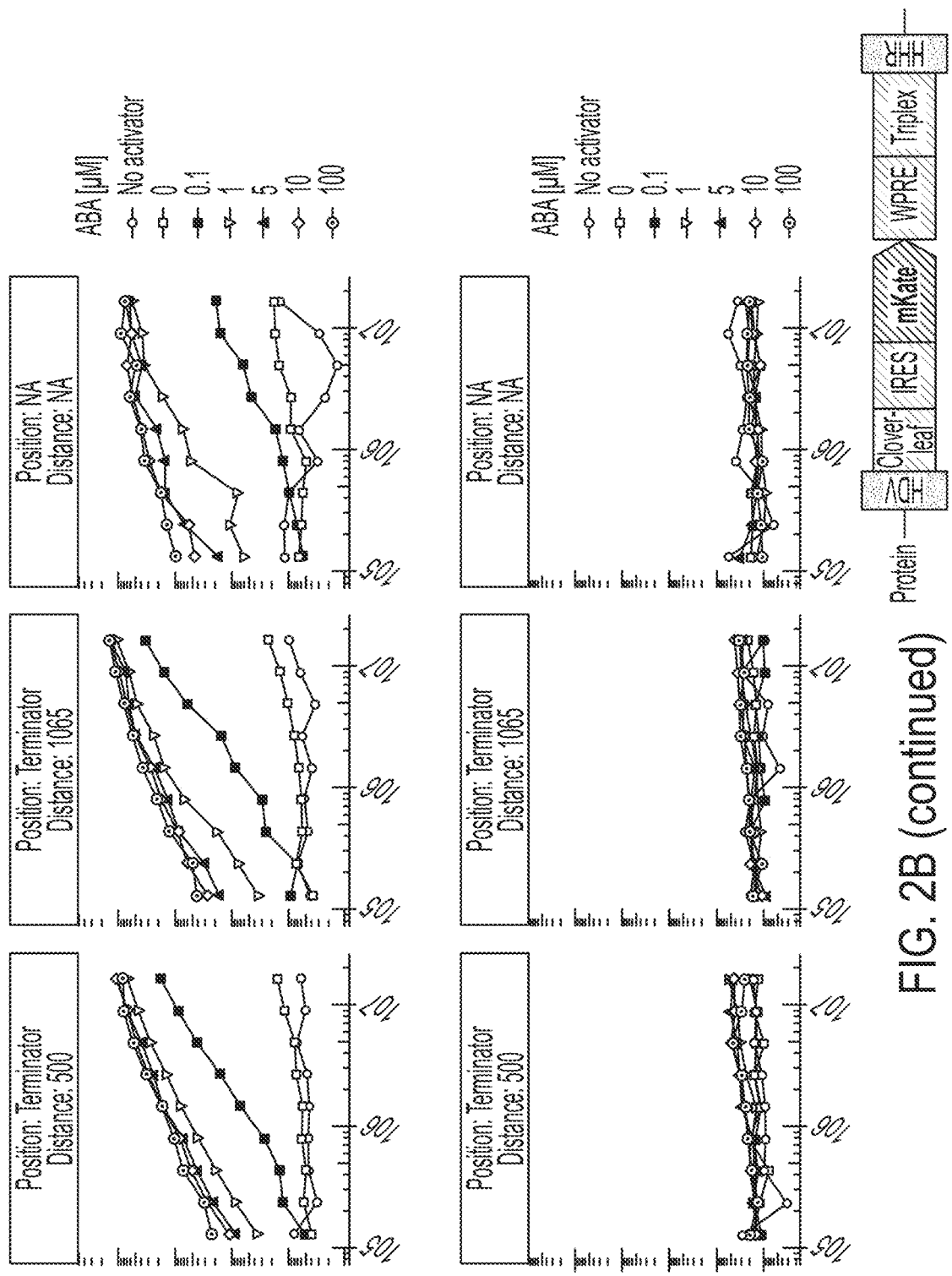

The capability of the post-PAS RNA to produce and process mature miRNA was tested. EYFP expression was driven by an ABA inducible promoter in the presence of different levels of ABA (0-100 μM) or in the absence of the activating transcription factor is shown in FIGS. 2A-2B, top panel. A miR-FF4 coding sequence was placed at various distances downstream of the annotated PAS in the Sox17 terminator. mKate was expressed from a plasmid separate from the EYFP-expressing plasmid. The mKate mRNA contains four binding site for the synthetic miR-FF4 in the 3'-UTR. HEK293 cells were co-transfected with the two plasmids and treated with various concentrations of ABA. Higher concentrations of ABA leads to successful transcription and processing of miR-FF4 located downstream of the PAS which resulted in miR-FF4 mediated mKate mRNA knockdown (FIGS. 2A-2B, bottom panel). A control (Position: 3'-UTR and Distance: NA) was included demonstrating the efficiency of having miR-FF4 placed in the 3'-UTR of the EYFP mRNA instead of downstream of the PAS, mKate and EYFP expression in the absence of any miR-FF4 is shown in the plot labeled Position: NA and Distance: NA.

Figure 2C:
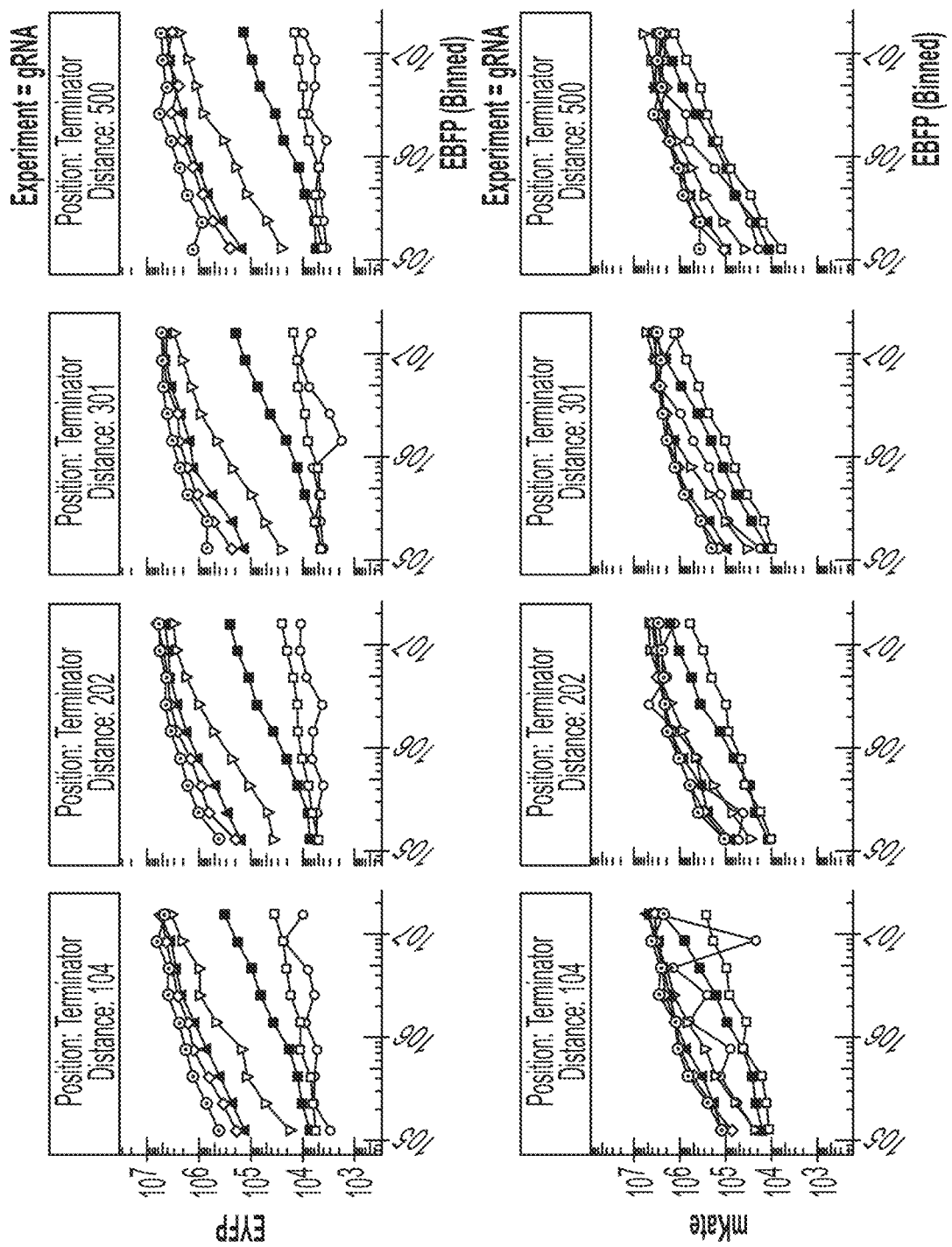
Figure 2C:
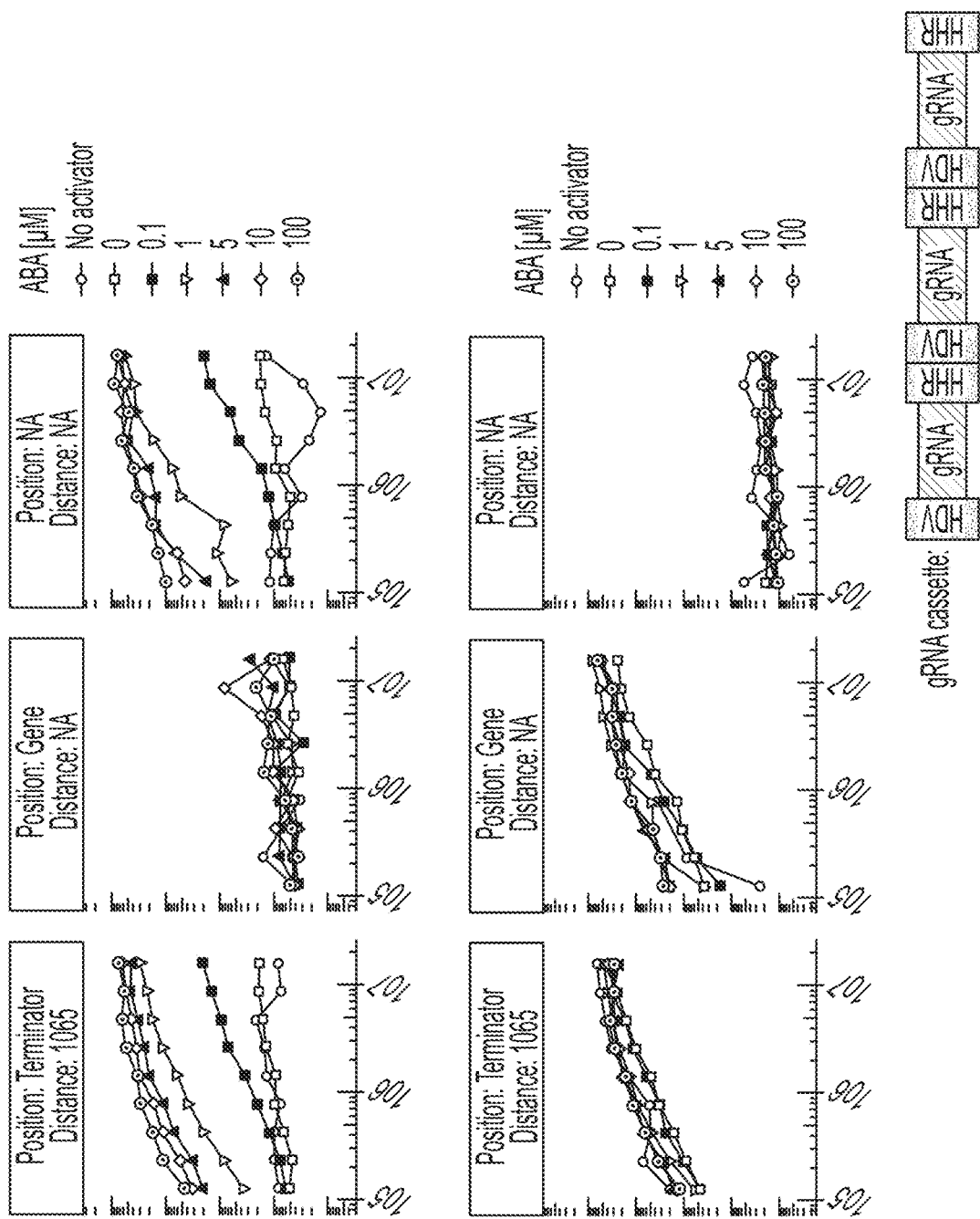

The capability of the post-PAS RNA to produce a protein was tested. EYFP expression was driven by an ABA inducible promoter in the presence of different levels of ABA (0-100 μM) or in the absence of the activating transcription factor is shown in FIGS. 2C-2D, top panel. A mKate coding sequence was placed at various distances downstream of the annotated PAS in the Sox17 terminator. Flanking ribozymes (HDV: HDV ribozyme, HHR: hammerhead ribozyme) are used to excise the post-PAS RNA from the transcribed strand. A cloverleaf sequence is included to act as a 5'-cap mimic, an internal ribosome entry site (IRES) is included to facilitate translation, and a WPRE and triplex sequence is included to facilitate protection against 3' exonucleases and to facilitate nuclear export and translation.HEK293 cells were co-transfected with the two plasmids and treated with various concentrations of ABA. Higher concentrations of ABA leads to successful transcription and translation of mKate located downstream of the PAS (FIGS. 2C-2D, bottom panel). mKate and EYFP expression in the absence the mKate encoding post-PAS RNA from the Sox17 terminator is shown in the plot labeled Position: NA and Distance: NA.

Figure 3A:
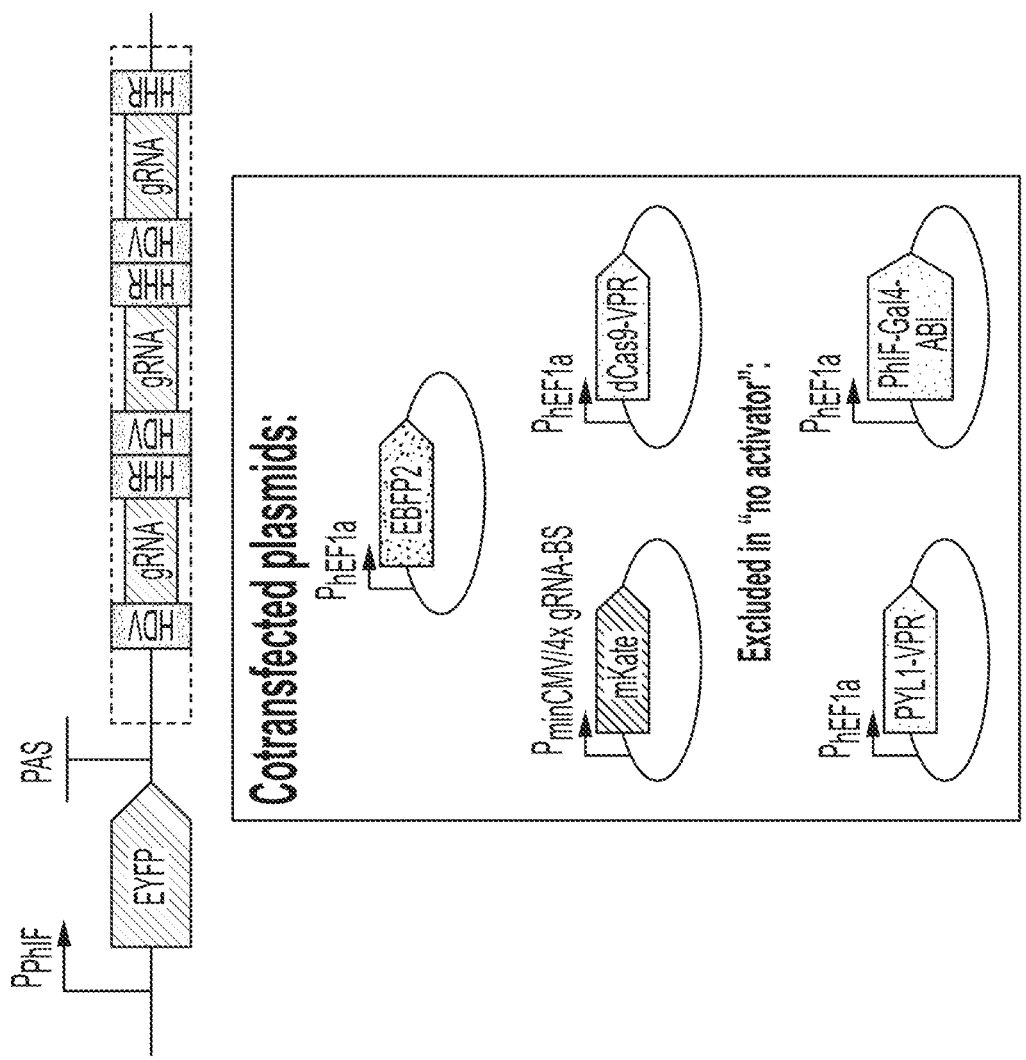
FIG. 3A-3I are charts showing the expression of gRNA downstream of a PAS using different terminators such as RPS14 terminator, SRSF3 terminator, or a GLO1 terminator.
Figure 3B:
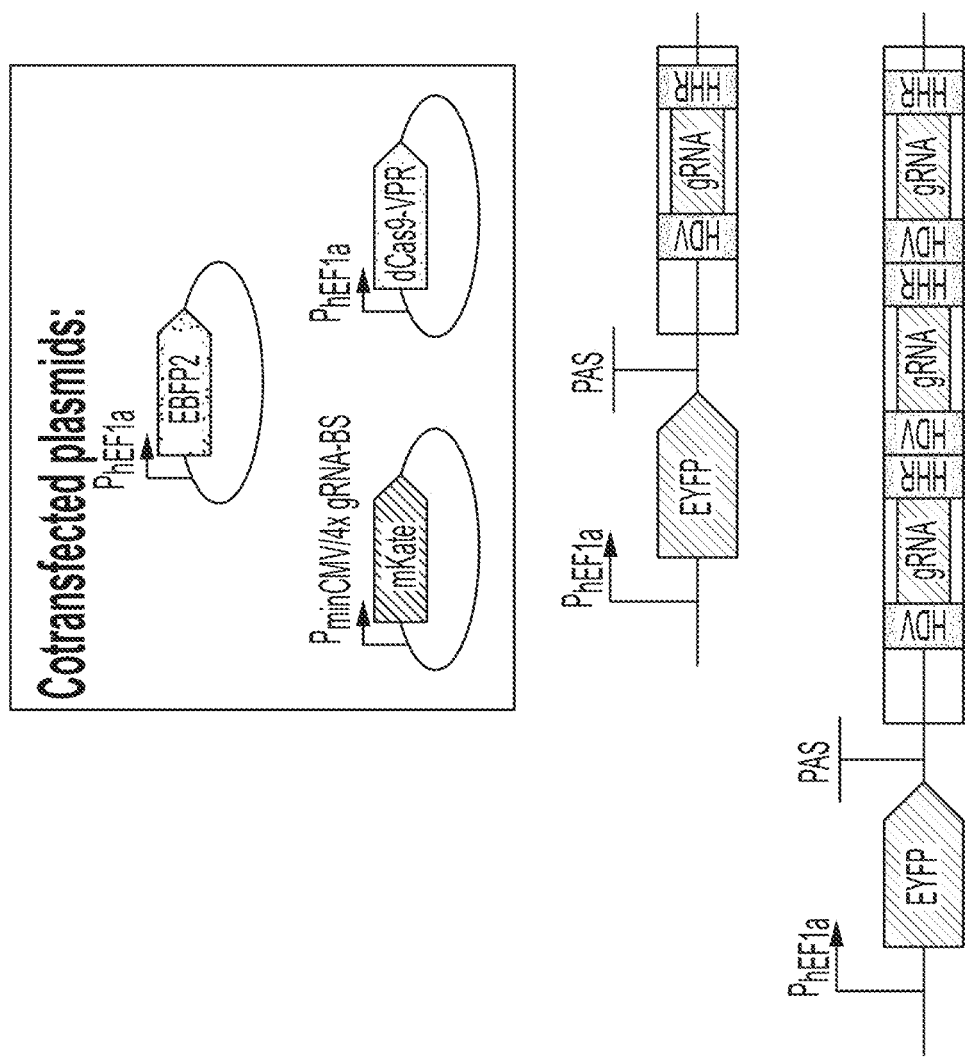
Figure 3C:
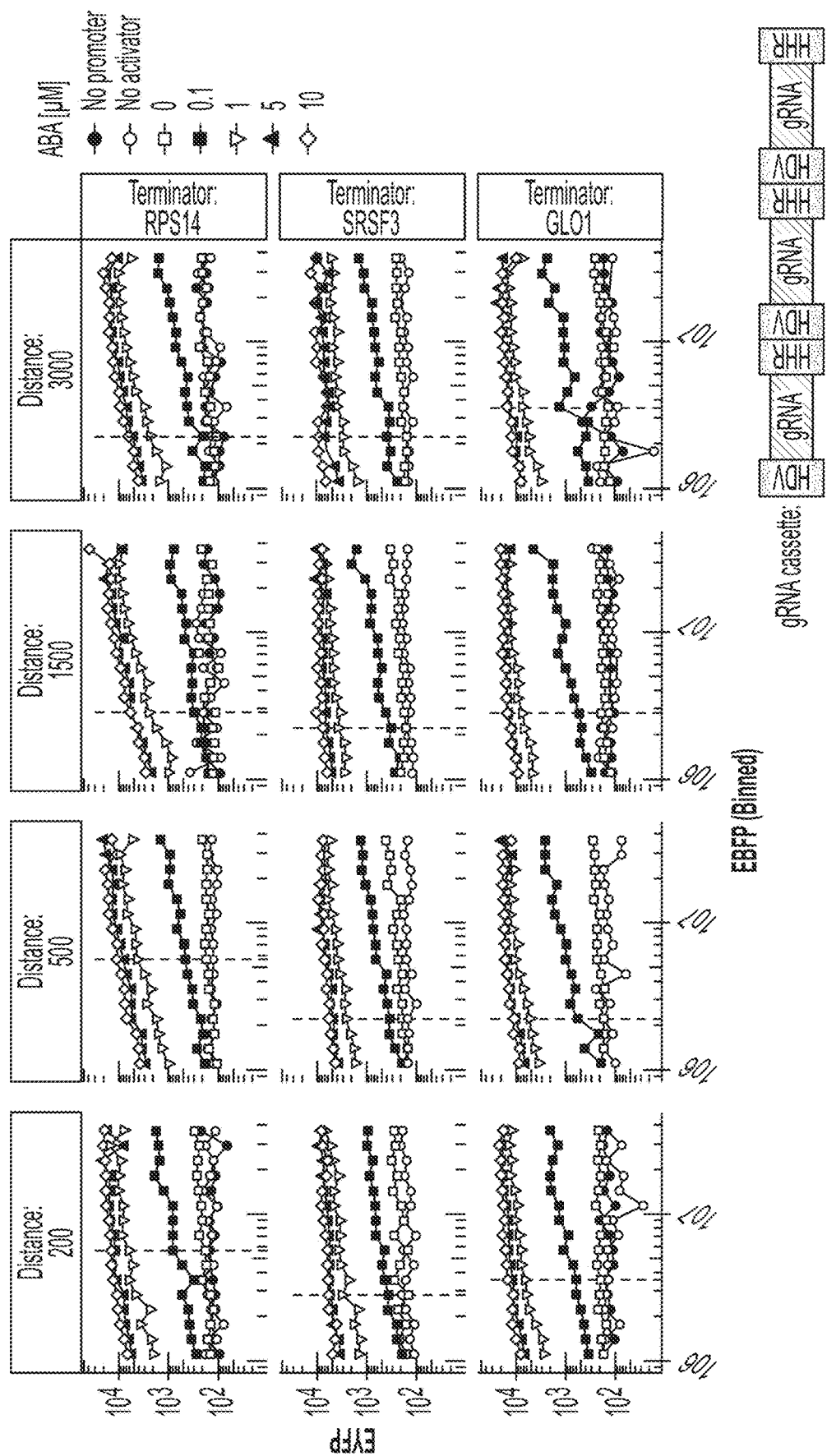
Figure 3D:
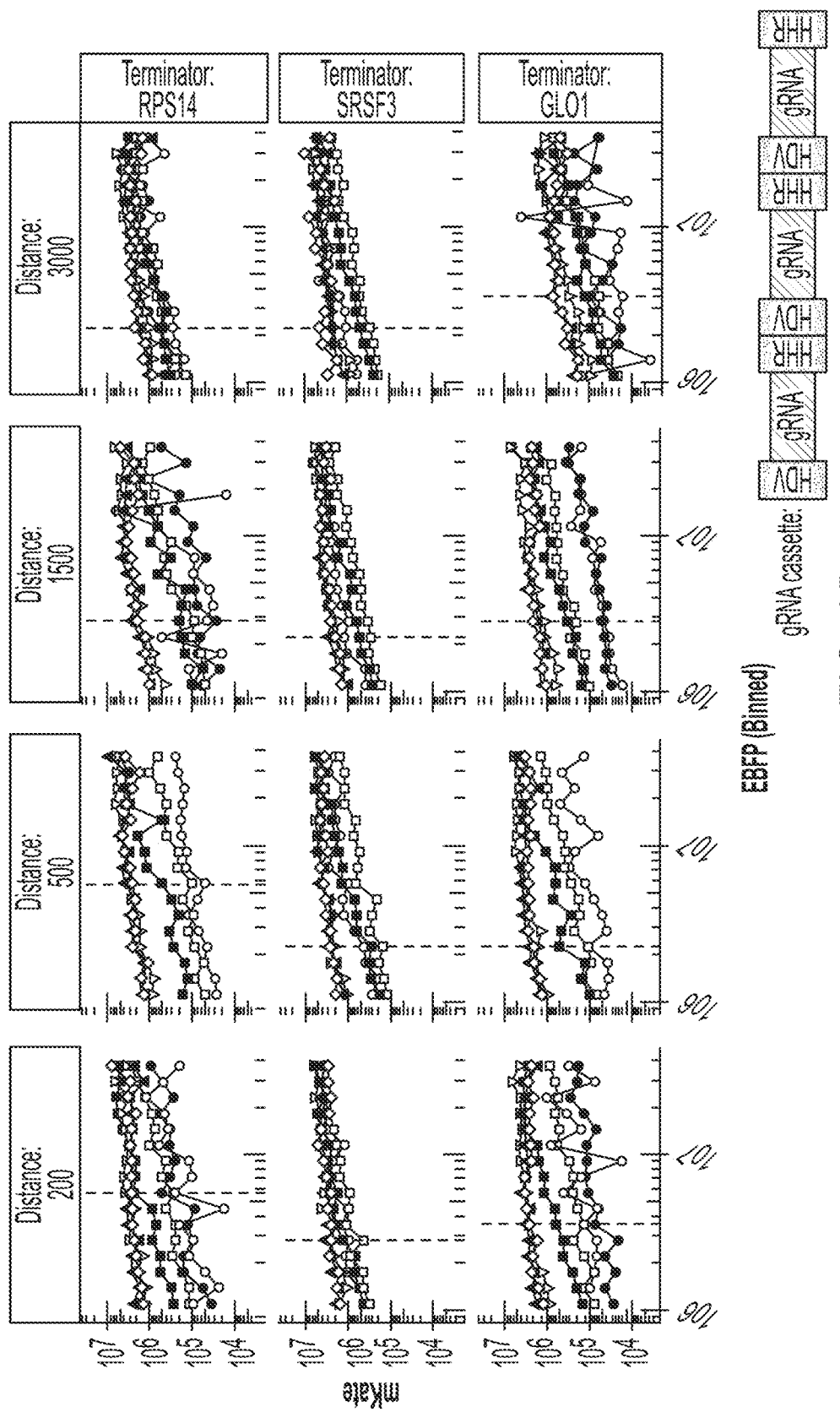

The capability of the post-PAS RNA to produce guide RNA was tested. The post-PAS gRNA construct includes three tandem repeats of a nRNA flanked by ribozymes (HDV: HDV ribozyme, HHR: hammerhead ribozyme), which were used to excise the post-PAS RNA from the transcribed strand. A plasmid with constitutive dCas9-VPR expression and a plasmid with a gRNA-inducible promoter driving mKate expression was co-transfected with the post-PAS gRNA construct. EYFP expression was driven by an ABA inducible promoter in the presence of different levels of ABA (0-100 μM) or in the absence of the activating transcription factor is shown in FIGS. 2C-2D, top panel. (FIGS. 2E-2F, top panel). mKate expression increases as a function of ABA indicating that the gRNA is being expressed downstream of the PAS and successfully processed. The gRNA was able to guide dCas9-VPR to activate the transcription of mKate (FIGS. 2E-2F, bottom panel). A control (Position: Gene and Distance: NA) was included demonstrating the expression of the gRNA. construct when directly expressed from the promoter otherwise driving EYFP instead of downstream of the PAS. mKate and EYFP expression for a construct that did not contain the sequence for the gRNA construct anywhere, is shown in the plot labeled Position: NA and Distance: NA Example 2: Terminators Derived from Different Genes Behaves Differently for Post-PAS gRNA Production Several different terminators were tested for their expression of gRNAs downstream of the poly A signal (PAS). Three tandem repeats of a gRNA cassette, each consisting of a gRNA flanked by self-cleaving ribozymes, were placed at various distances from the PAS. HEK293 cells were transfected with a unique constructs, a transfection marker (expressing EBFP2), a plasmid for constitutive dCas9-VPR expression, a reporter that requires the gRNA and dCas9-VPR to be present to activate mKate expression, and a inducible, split transcription factors that dimerizes and activates transcription of the $P_{hlF}$ promoter on the construct in the presence of abscisic acid (ABA) (FIG. 3A), Terminators derived from RPS14, SRSF3 and GLO1 were tested. In FIG. 3C and FIG. 3D, the x-axis shows EBFP bin which uses the transfection marker to calculate plasmid copy number for each cell. Induction of EYFP increased as function of ABA, demonstrating the simple genetic circuit responds to the inducer. The horizontally dashed line indicates the EBFP bin where the greatest difference in mKate is observed between the induced (ABA>0) and uninduced (ABA=0) sample for each unique construct. mKate expression was induced by Cas9-VPR guided by gRNA produced from different terminators downstream of PAS at various levels, indicating that different terminators behaves differently with respect to driving the expression of the post-PAS RNA. The two plasmids for the split transcription factor were not included in the "No activator" control. The "no promoter" control has the PhlF promoter replaced by 20 nucleotides that do not serve as a promoter.

Figure 3E:
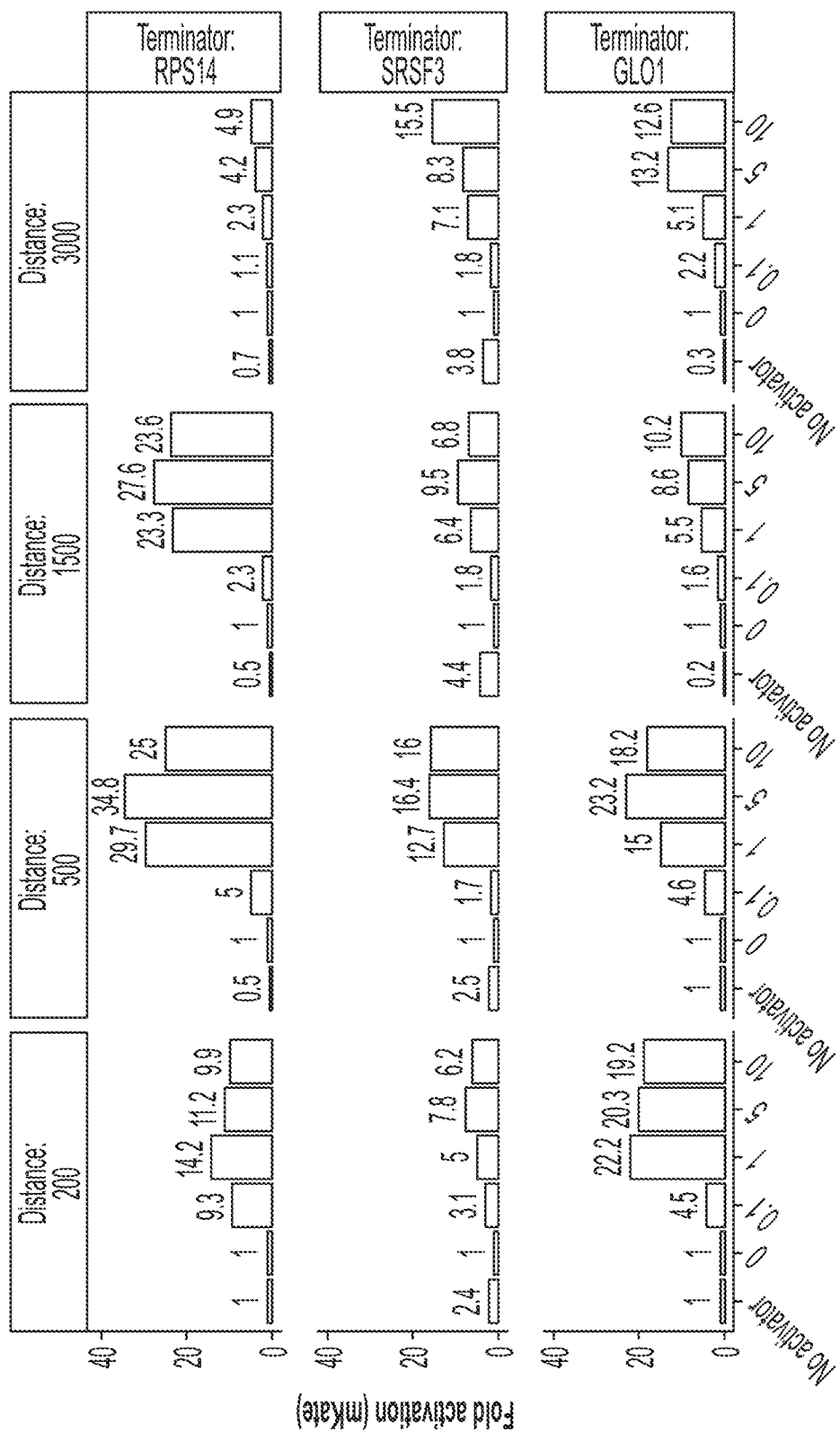
Figure 3F:
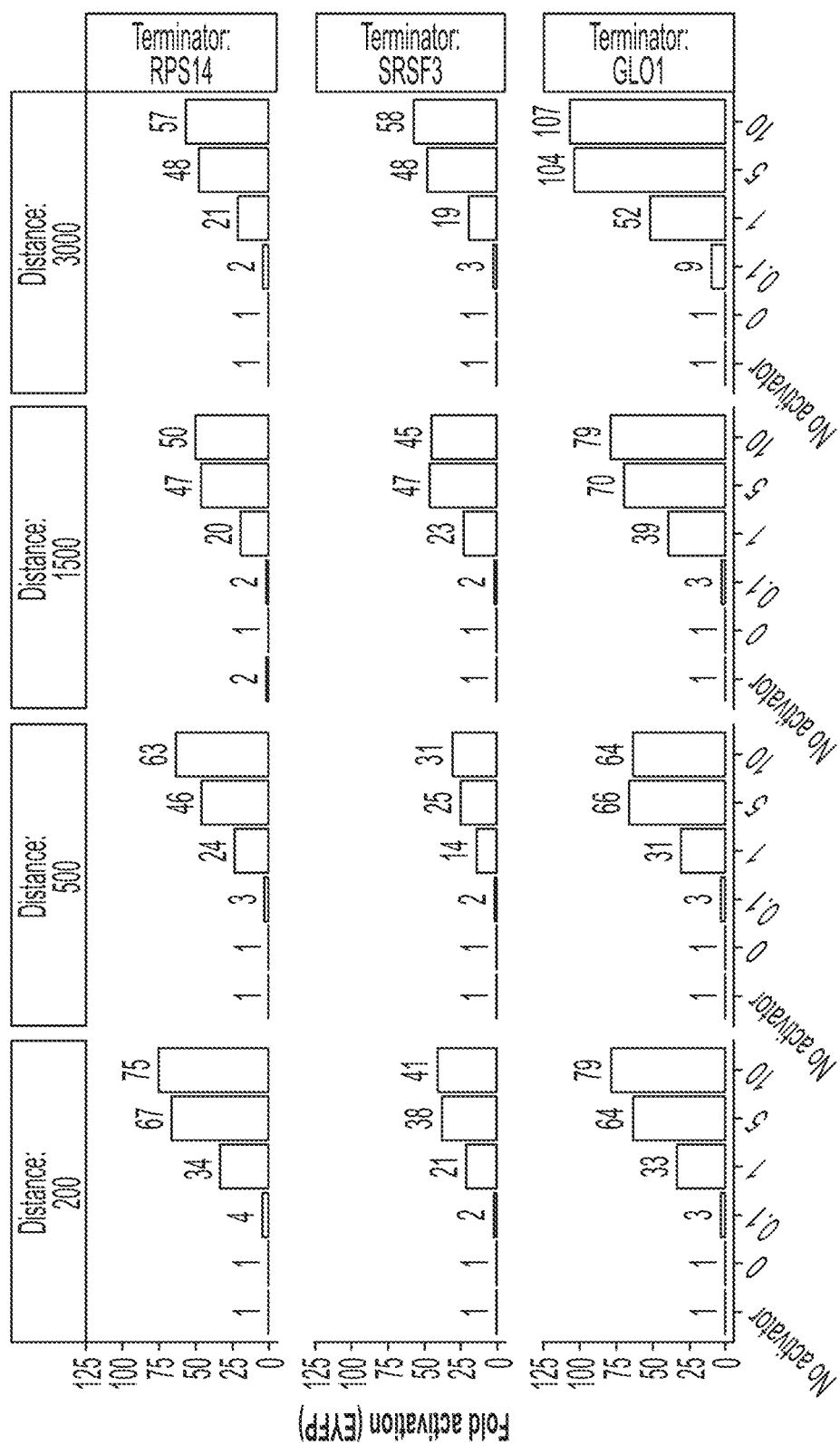
Figure 3G:
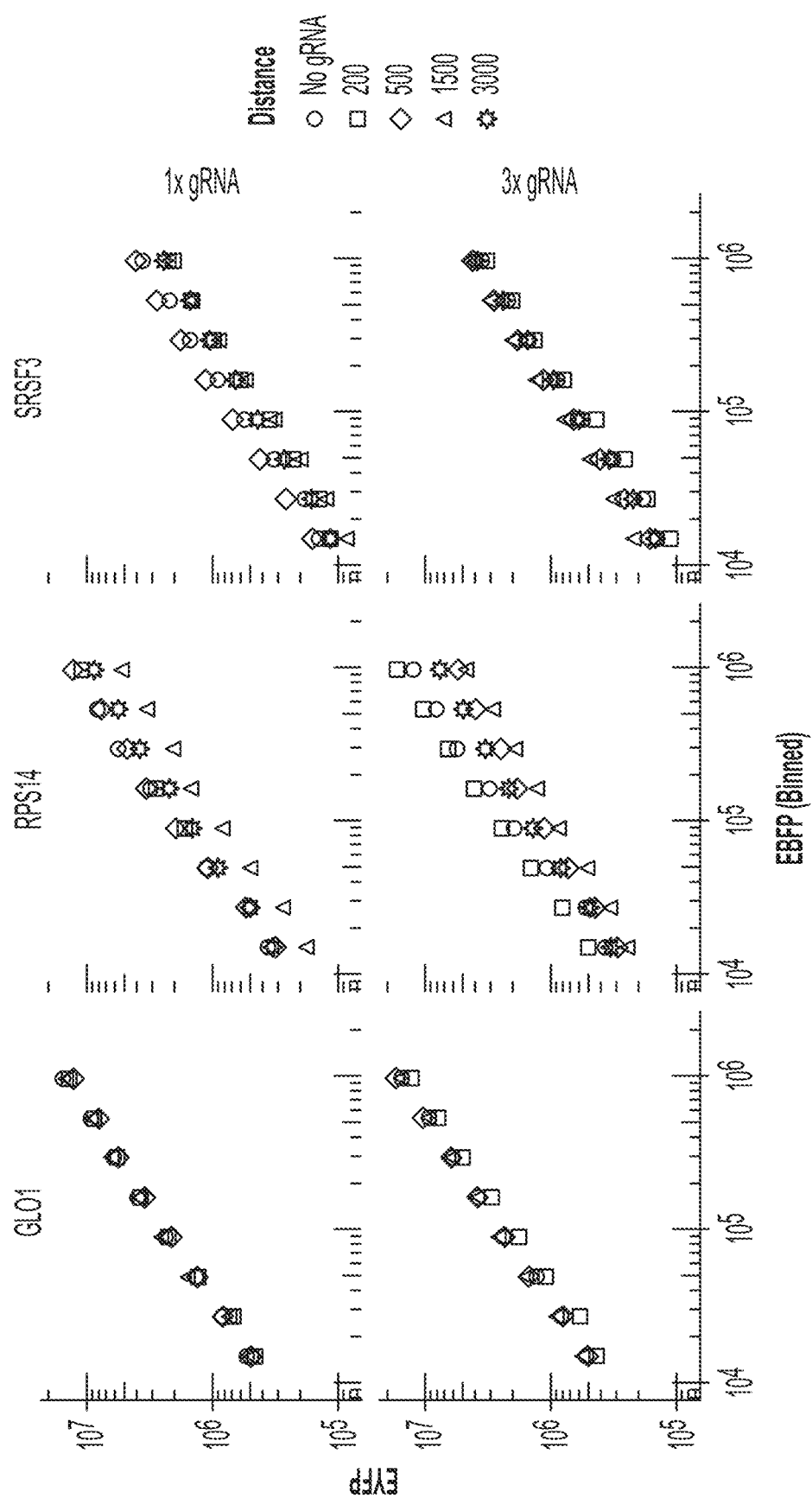
Figure 3H:
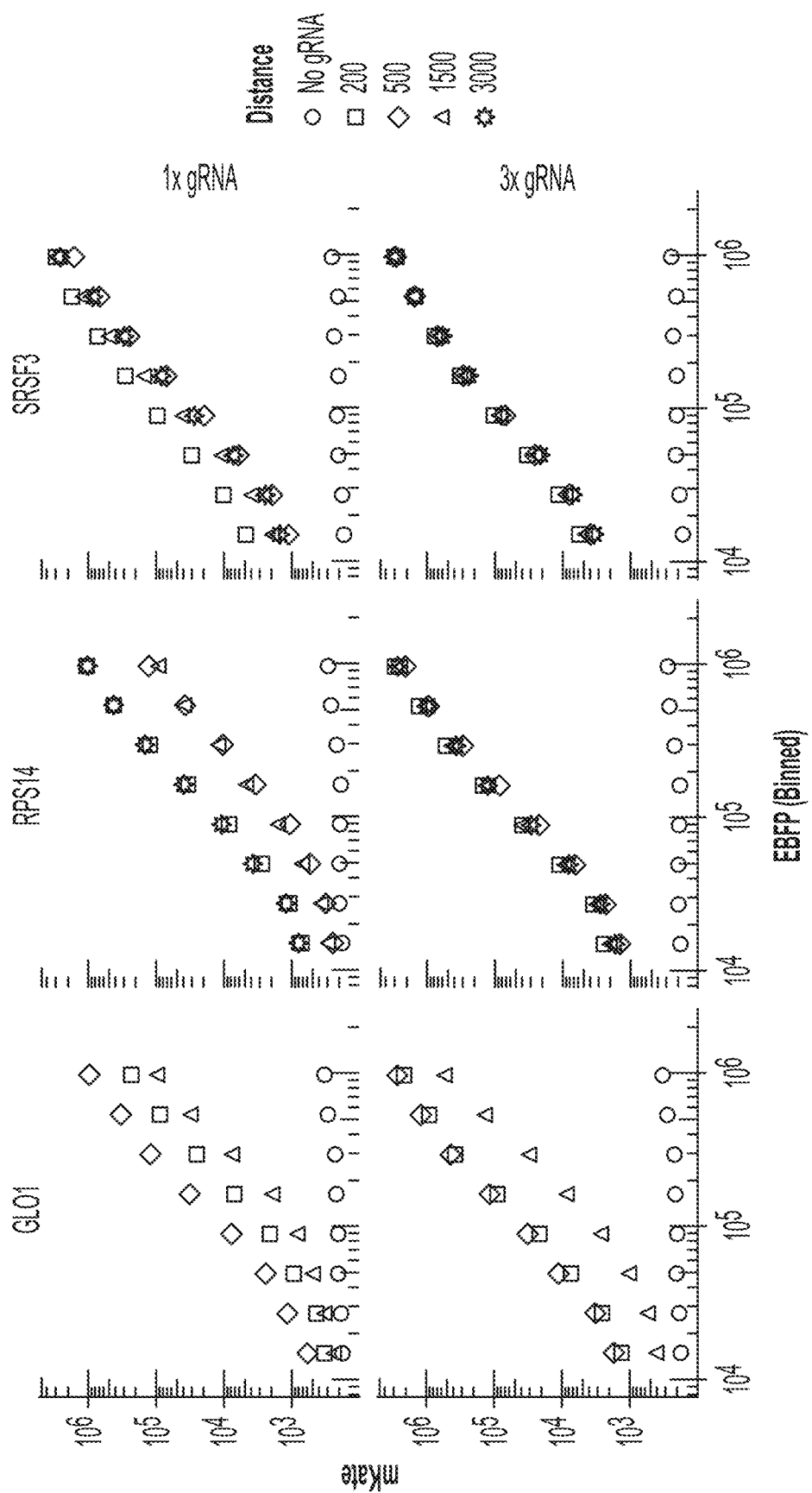
Figure 3I:
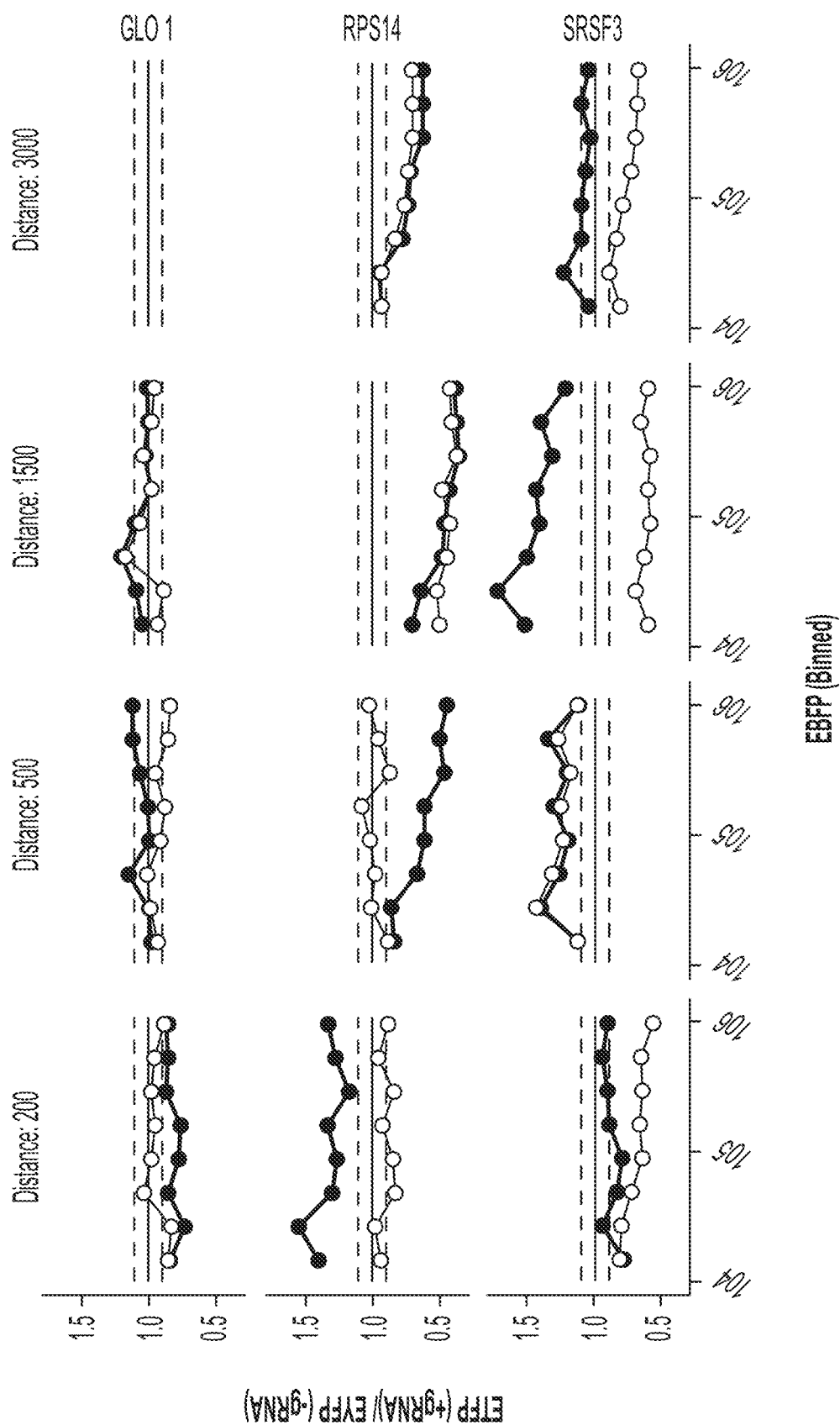

FIG. 3E shows the highest fold-change in mKate expression for the best performing EBFP bin. The fold-change was calculated as the maximum difference in mKate expression between the induced (ABA>0) and uninduced (ABA=0) sample (refer to the horizontal line in FIGS. 1. and 2). FIG. 3F shows the highest fold-change in EYFP expression for the same EBFP bin shown in FIG. 3E. The fold-change was calculated as the maximum difference in EYFP expression between the induced (ABA>0) and uninduced (ABA=0) sample (refer to the horizontal line in FIGS. 1 and 2). The two plasmids for the split transcription factor were not included in the "No activator" control. FIG. 3G shows that some terminators have a modest effect on upstream gene expression. This could potentially be due to parts of the 3' UTR from the endogenous gene being included in the terminator. The "no gRNA" control is the terminator without the gRNA cassette. FIG. 3H shows that gRNAs, as measured by mKate expression, can be expressed downstream of a PAS, The distance between the gRNA cassette and the PAS as well as the number of gRNA cassettes and the terminator being used, each have an effect on gRNA expression. The "no gRNA" control is the terminator without the gRNA cassette. The effect of gRNA expression on the upstream gene was tested by expressing different copies of gRNA. FIG. 3B shows the vectors transfected to HEK293 cells to test different terminators in producing gRNA downstream of PAS; the post-PAS RNA either encodes a single gRNA cassette or three copies of gRNA cassettes. FIG. 3I shows that some terminators are more sensitive to perturbations, which may lead to changes in upstream gene expression. In all cases, a construct with a minimal impact on upstream gene expression can be found.

Figure 4:
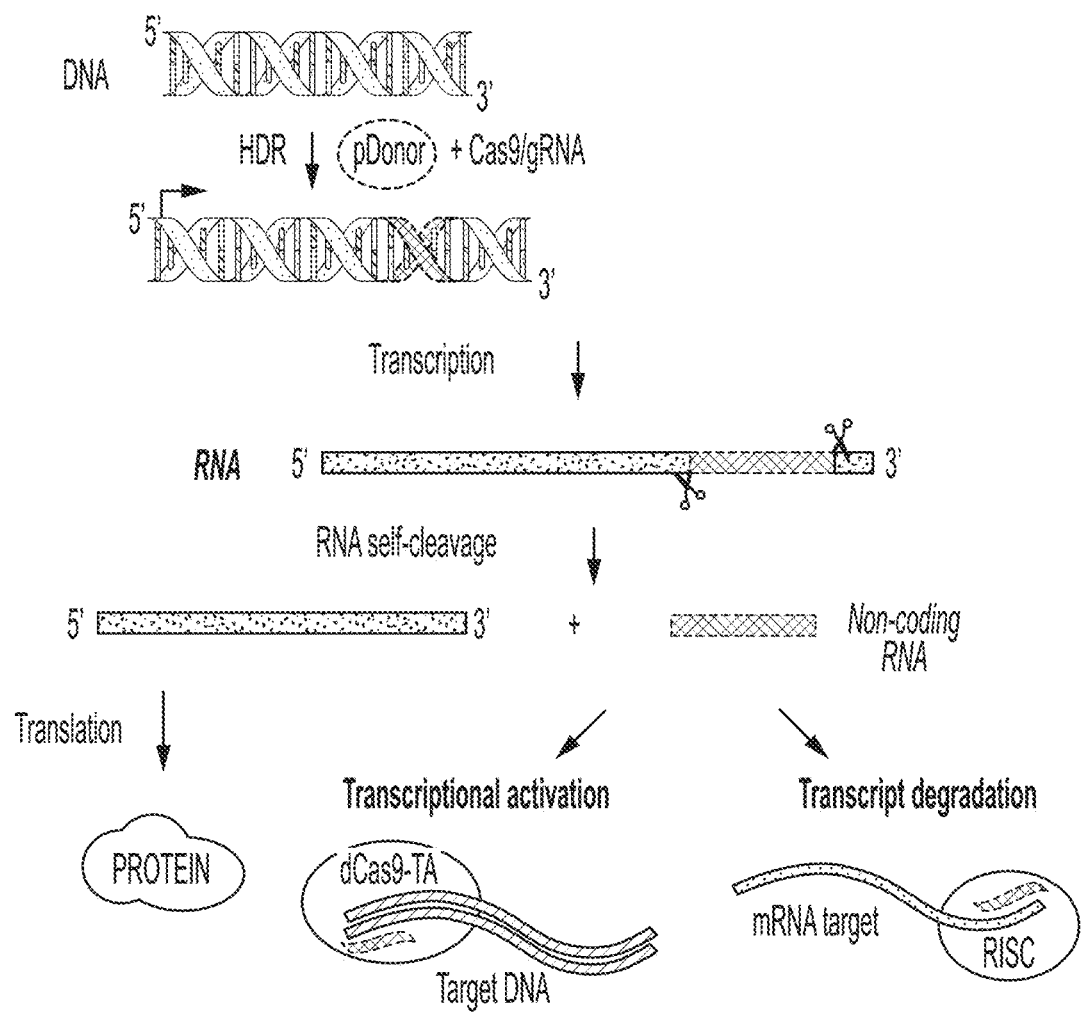
FIG. 4 shows an exemplary experimental design of replacing the terminator region of an endogenous gene by a nucleotide sequence encoding engineered post-PAS RNA using CRISPR/Cas9 for expression of a non-coding RNA. The post-PAS RNA is transcribed with the endogenous gene and undergoes self-cleavage to be separated from the mRNA of the endogenous gene. The endogenous gene can then be translated to a protein, whereas the non-coding RNA can elicit its downstream function, such as transcriptional activation or transcript degradation.

Example 3: Engineered Non-Coding RNA Expression Cassette at the Taror Region of an Endogenous Gene The endogenous mRNA can be engineered to possess self-cleavage activity for the creation of two separate transcripts, one for the endogenous gene and one for non-coding RNA. Expression of non-coding RNA will allow direct control of genes in multi-step differentiation. The expression cassette of the non-coding RNA can be introduced to downstream of PAS of an endogenous gene by CRISPR/Cas9 mediated gene editing. The transcription initiated from the promoter of the endogenous gene will produce one single mRNA including the mRNA of the endogenous gene and the non-coding RNA. The self-cleavage site serves to separate the ncRNA from the mRNA thus producing two individual RNA molecules. The mRNA of the endogenous gene can then be translated to the protein and the ncRNA can elicit its intended function downstream. (FIG. 4).

To engineer an ncRNA expression cassette to be placed downstream of a PAS signal, which can result in single copy stable and mature functional RNA, a number of factors were considered, such as synthetic poly A tail for sustained upstream mRNA splicing and stability; cleavage sites flanking the coding sequence; and number of copies of the ncRNA expression cassettes.

Figure 5A:
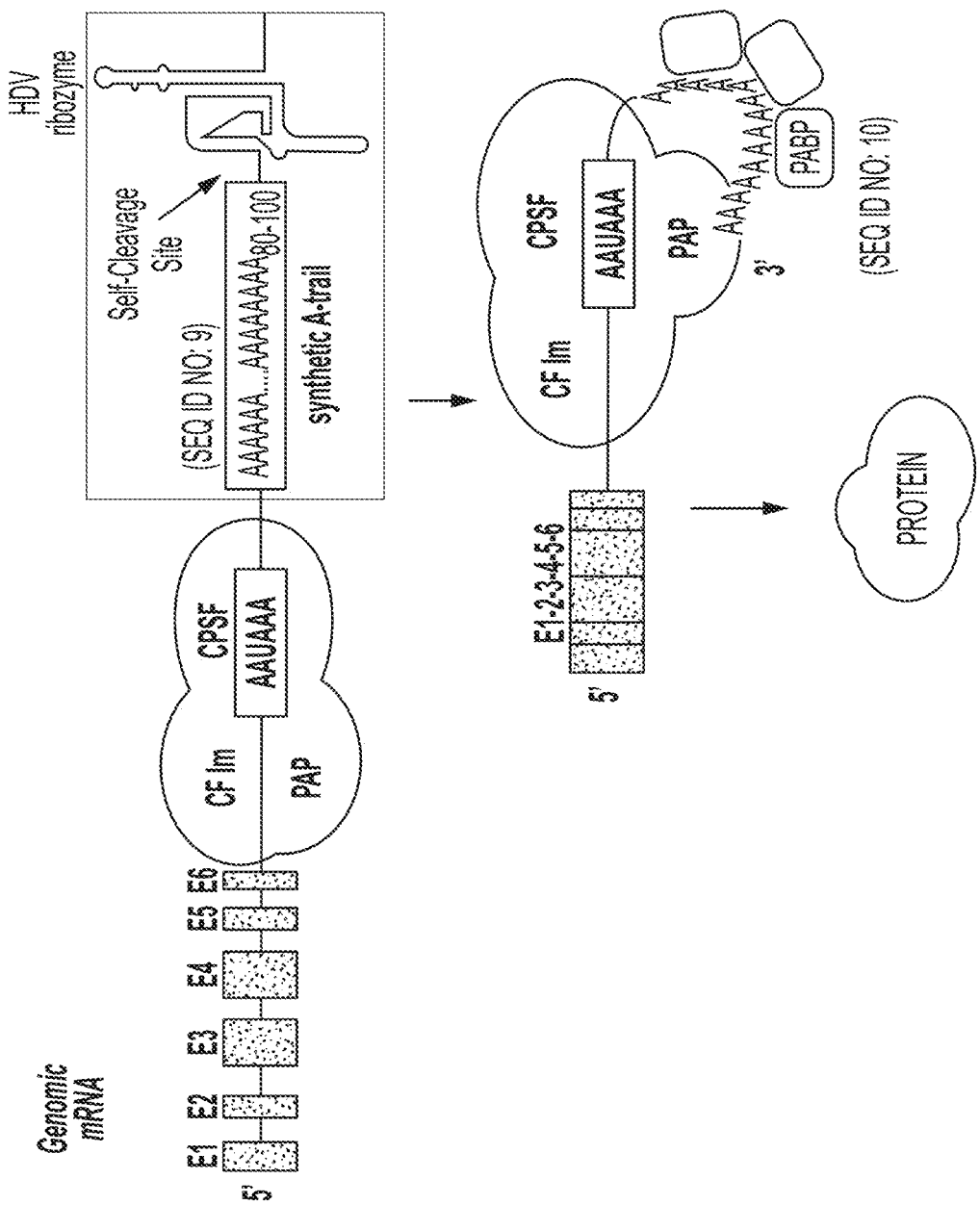
FIGS. 5A-5H are figures showing that a synthetic poly A tail can sustain splicing and stability of mRNAs.
Figure 5B:
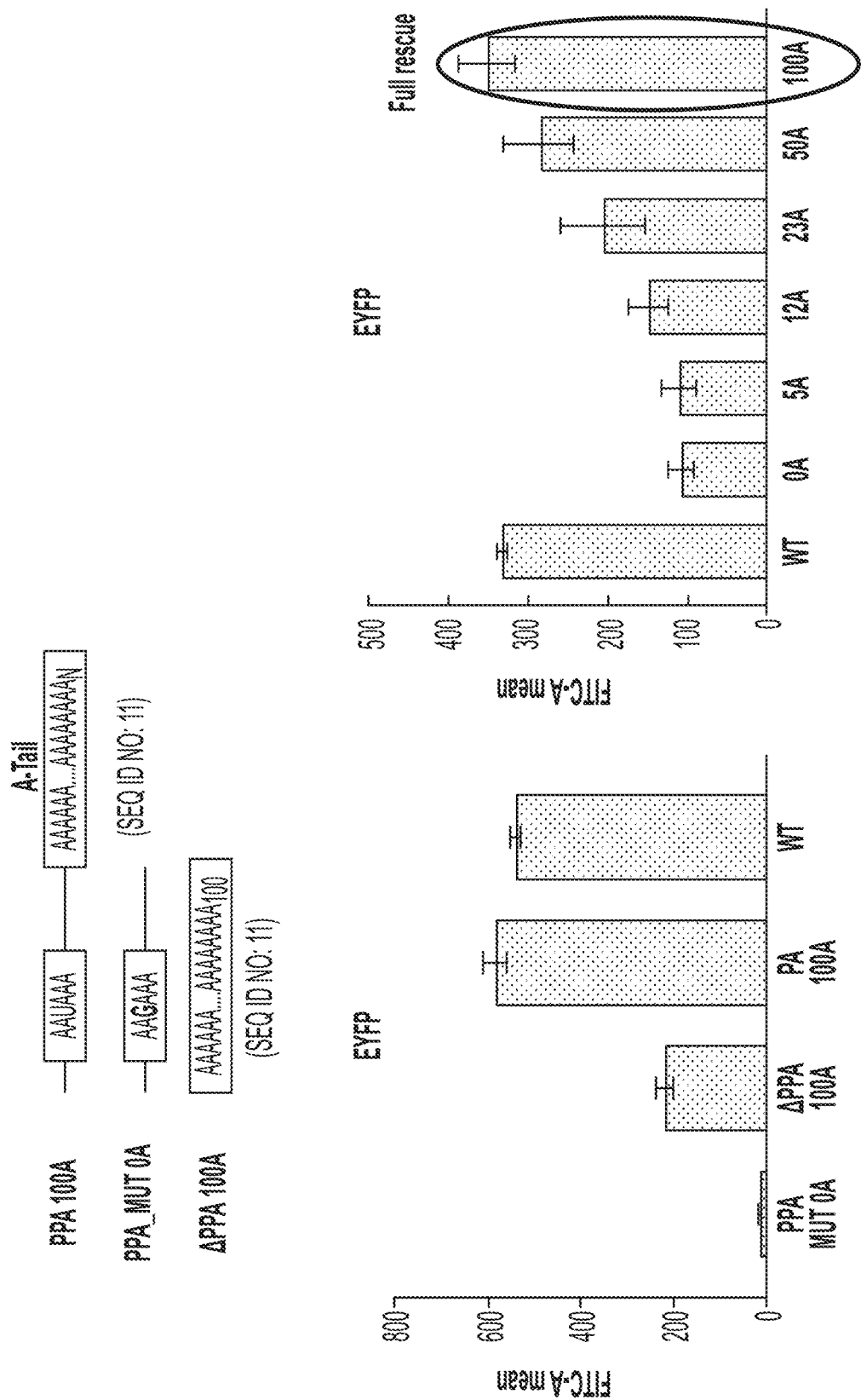

FIG. 5A shows once the upstream mRNA is cleaved at a cleavage site, a poly(A) tail will be added to the mRNA. CPSF, bound to polyadenylation signal AAUAAA, and PABP, bound to the growing poly(A) tail, cooperatively stimulate poly(A) polymerase such that a complete poly(A) tail is synthesized in one possessive event, which terminates at a length of 250 nucleotides. Previous studies have shown that a synthetic poly A tail is capable of sustaining splicing and stability of the mRNA of the upstream gene (Muinz, et al., *Mol Cell Biol*. 2015 July; 35(13): 2218-2230). Moreover, whether a poly A signal is needed in addition to a synthetic poly A tail for upstream gene expression was tested. Three constructs was designed: (i) EYFP expression cassette with AAUAAA as PAS and an additional poly A tail (PPA 100A); (ii) EYFP expression cassette with a mutant PAS AAGAAA (PPA_MUT 0A); and (iii) a synthetic poly A tail alone (ΔPPA 100A). EYFP expression cassette with wild type poly A termination signal was used as a control. The constructs were transfected to HEK293 cells respectively, and EYFP expression was quantified and compared among the constructs. FIG. 5B, left panel shows PPA 100A is as good as wild type poly A in sustaining upstream mRNA expression whereas PPA_MUT 0A is not able to sustain upstream gene expression and ΔPPA 100A's ability to sustain upstream gene expression reduced significantly. Accordingly, it is desired that the terminator region of the engineered nucleic acid encoding a PAS RNA has the PAS signal AAUAAA, and a synthetic poly A tail can be optionally placed after the PAS. The length of the poly(A) tail also impacts the upstream gene expression. FIG. 5B right panel shows that the longer the poly(A) tail is, the better it can support upstream gene expression.

Figure 5C:
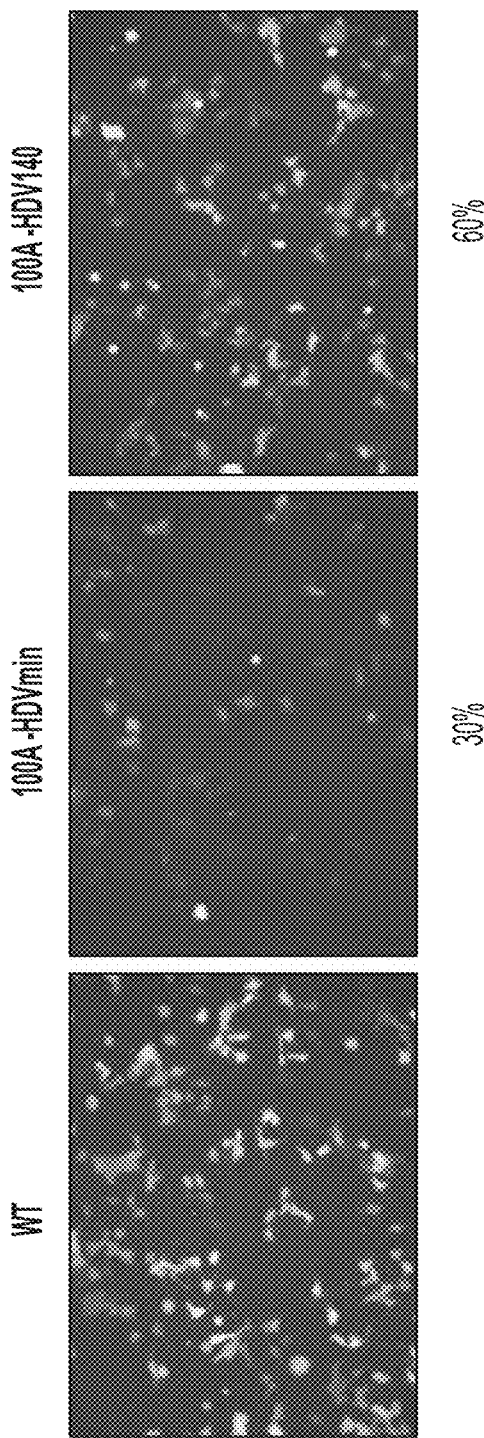
Figure 5D:
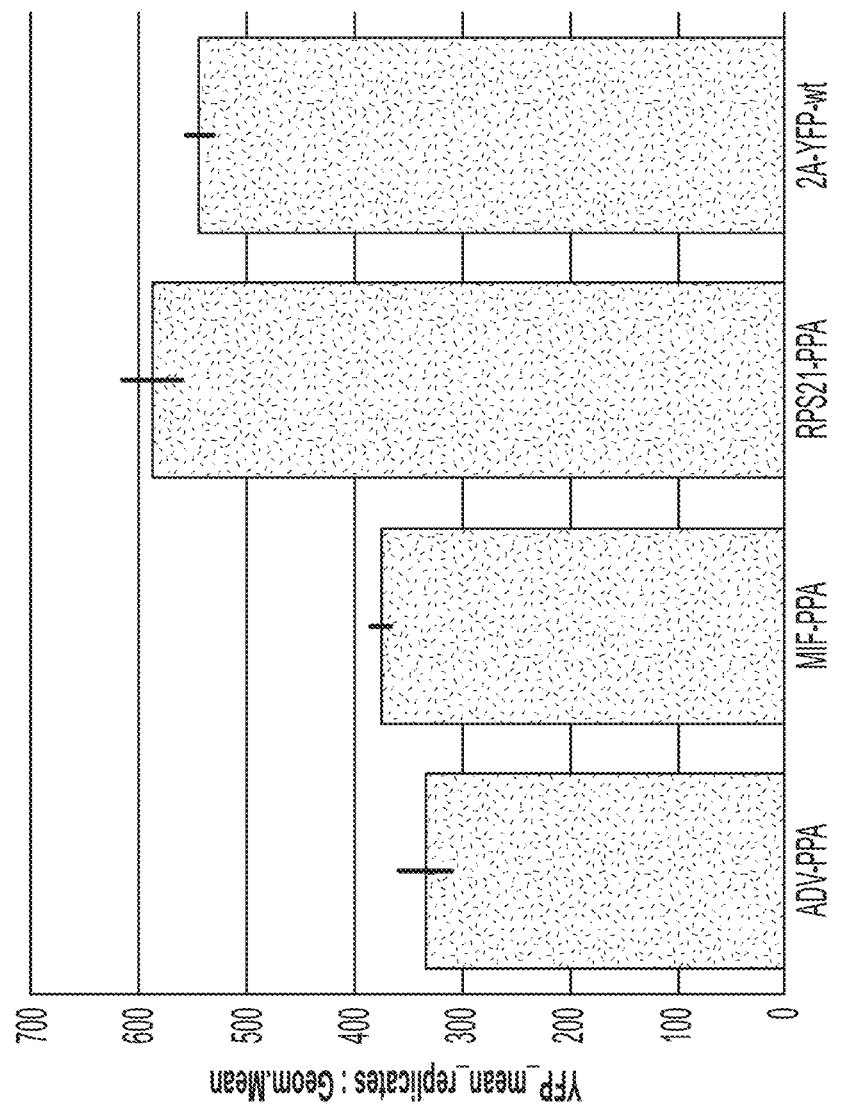
Figure 5E:
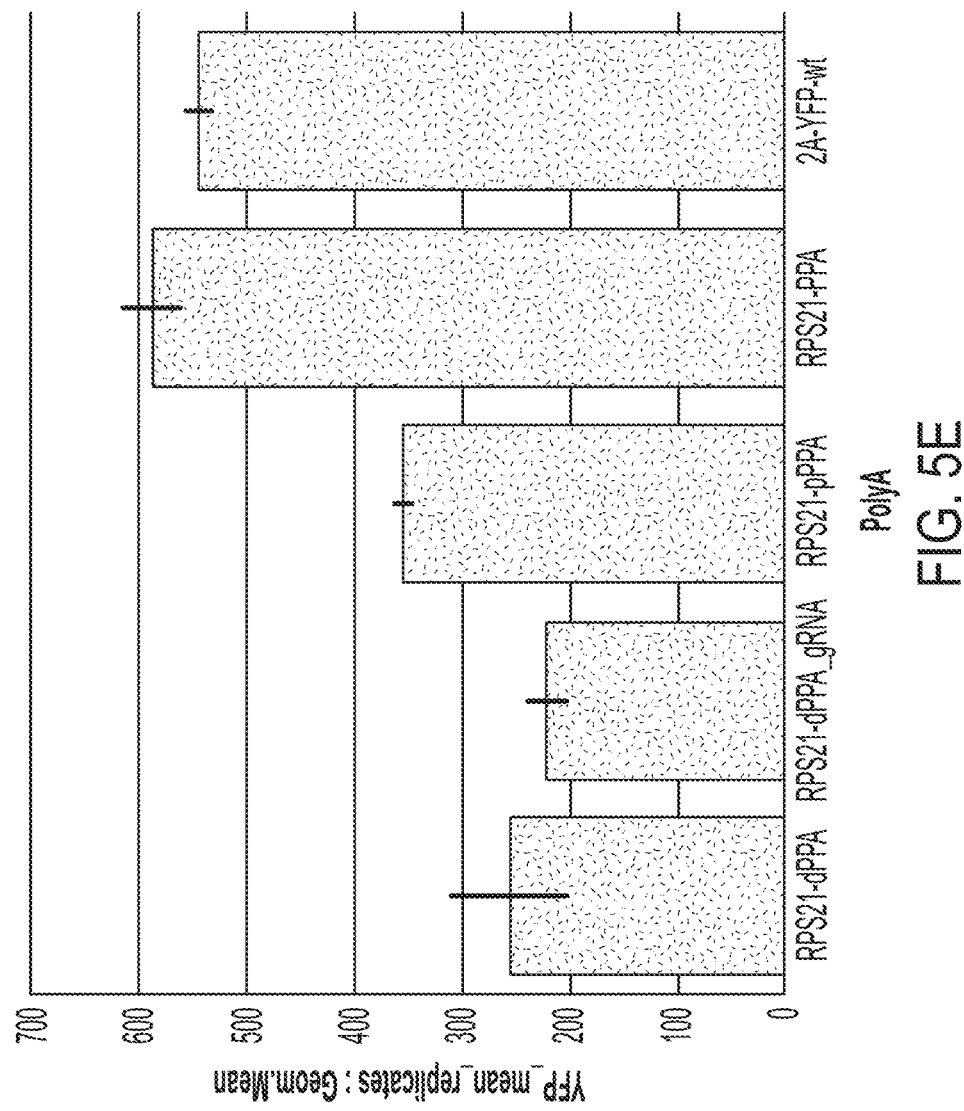
Figures 5F, 5G:
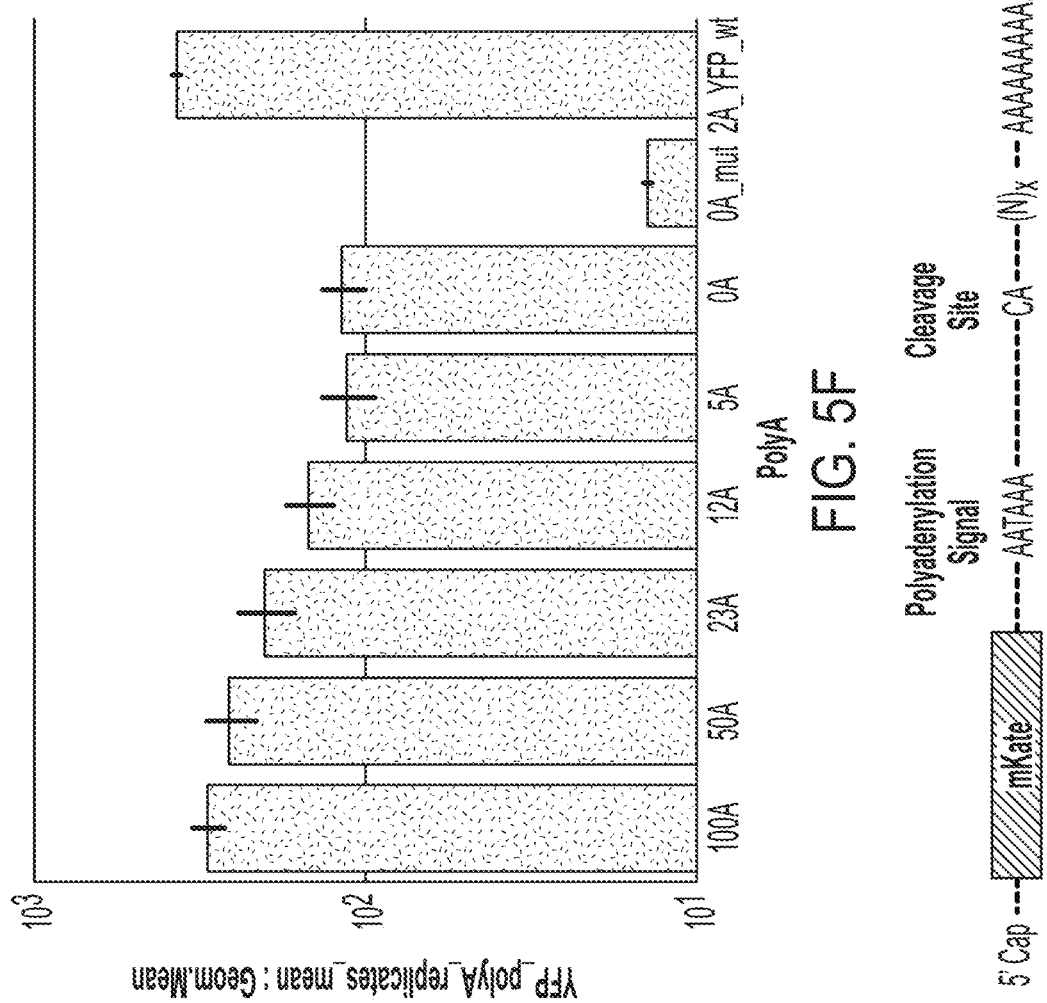
Figure 5H:
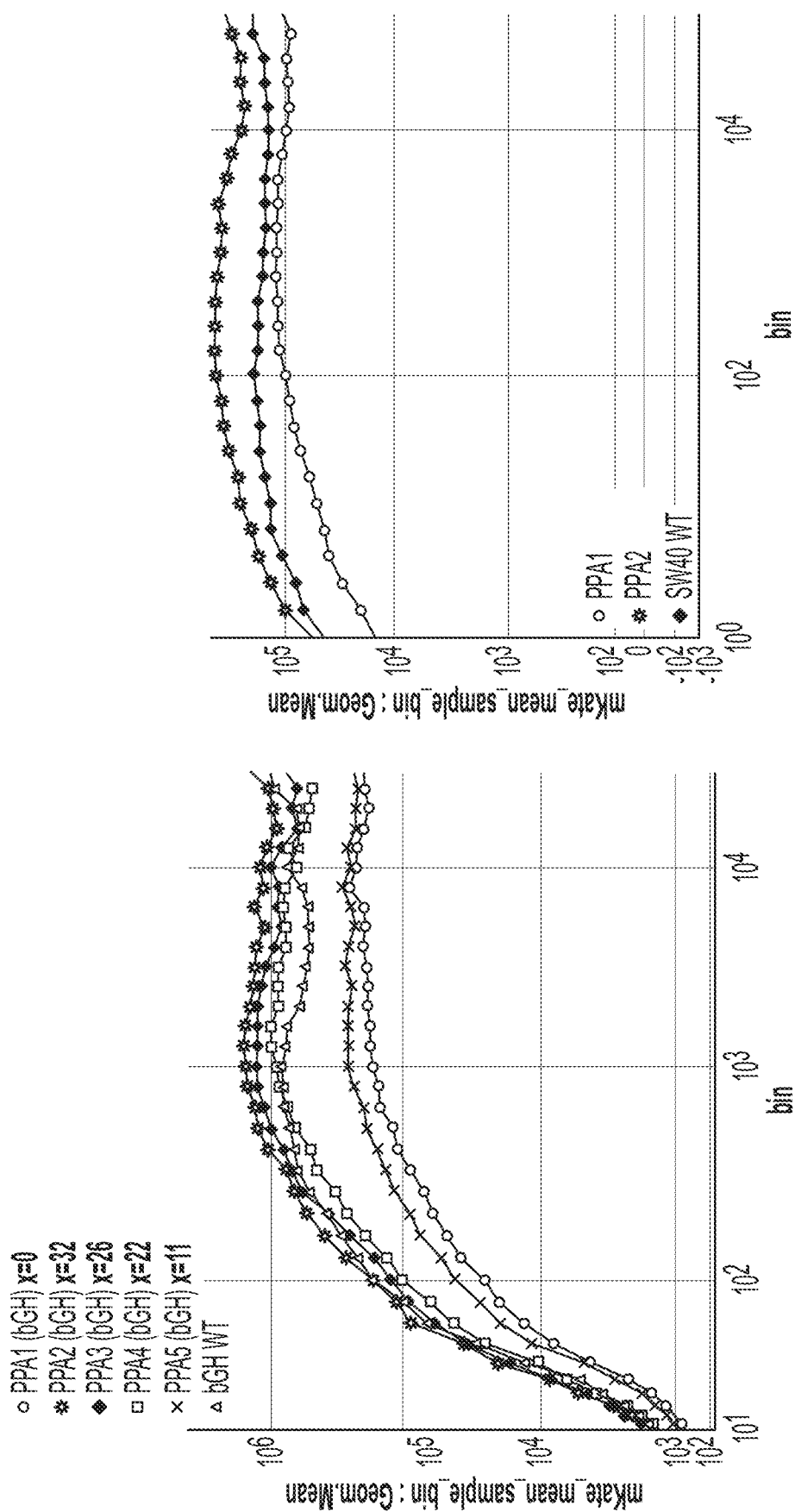

Surprisingly, it was discovered that placing the poly A tail a certain distance away from the cleavage site was beneficial to sustaining the expression of the upstream gene. A poly A tail can be placed downstream of the cleavage site by any number of random nucleotides $(N)_x$ (FIG. 5G). To test this, a poly A tail was placed 11 nucleotides, 22 nucleotides, 26 nucleotides and 32 nucleotides downstream of the cleavage site in the terminator region of a mKate expression construct. The constructs were transfected to cells, and the expression of mKate was tested. The results showed that constructs with the poly (A) tail 22 nucleotides, 26 nucleotides, and 32 nucleotides away from the cleavage site showed higher expression of mKate than the constructs with the poly A tail placed 0 nucleotides away from the cleavage site. The construct with the poly A tail placed 11 nucleotides away also showed slightly higher expression level than he constructs with the poly A tail placed 0 nucleotides away from the cleavage site (FIG. 5H)

In addition, a RNA cleavage site may be necessary 3' to the poly A signal to release the mRNA of the post-PAS RNA. A ribozyme site following the PAS was contemplated. Hepatitis delta virus (HDV) ribozyme, which is one of the small self-cleaving ribozymes, were tested. Under transcriptional conditions, wild-type ribozyme sequence and flanking sequence work in concert to promote efficient self-cleavage during transcription (Durga et al., *RNA*. 2007 December; 13(12): 2189-2201). To test whether wild type HDV ribozyme also supports upstream gene expression by effective cleavage of mRNA from post-PAS RNA, WT HDV ribozyme, HDVmin and HDV140 was tested. The constructs from 5' to 3' include: EYFP coding gene, PAS, Poly(A)$_{100}$ tail, ribozyme to be tested. FIG. 5C shows that the construct contains wild type HDV ribozyme has the highest EYFP expression, suggesting that placing a wild type HDV ribozyme after the poly(A) tail is preferred for upstream mRNA separation and expression. FIG. 5D-5F are data analysis showing Poly(A) tuning comparisons. FIG. 5D shows that the identity of the poly A signal matters. Replacing the RPS21 poly A signal sequence with other poly A signal sequences (ADV and MIF) reduces expression of RPS21-2A-YFP from the endogenous RPS21 genomic locus. FIG. 5E shows that the full length poly A signal sequence is needed, showing that expression of RPS21-2A-YFP is reduced when using mutated RPS21 poly A signal (dPPA) or partial poly A signal (pPPA). FIG. 5F shows that length of the PolyA sequence after the Pre-PolyA matters, showing that 100A essentially recovers WT expression of RPS21-2A-YFP.

Figure 6A:
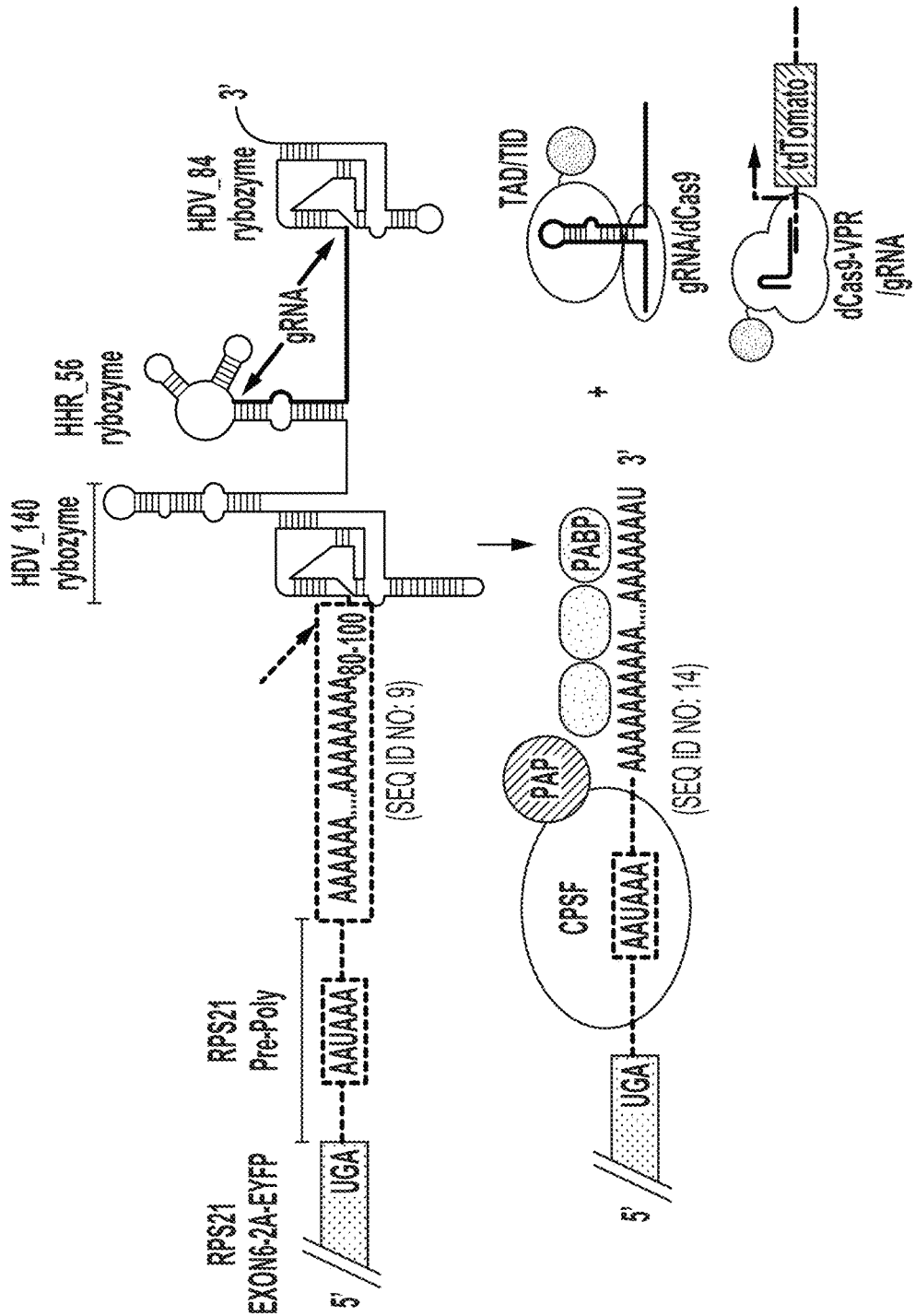
FIGS. 6A-6F are figures showing generation of gRNA using post-PAS RNA.
Figure 6B:
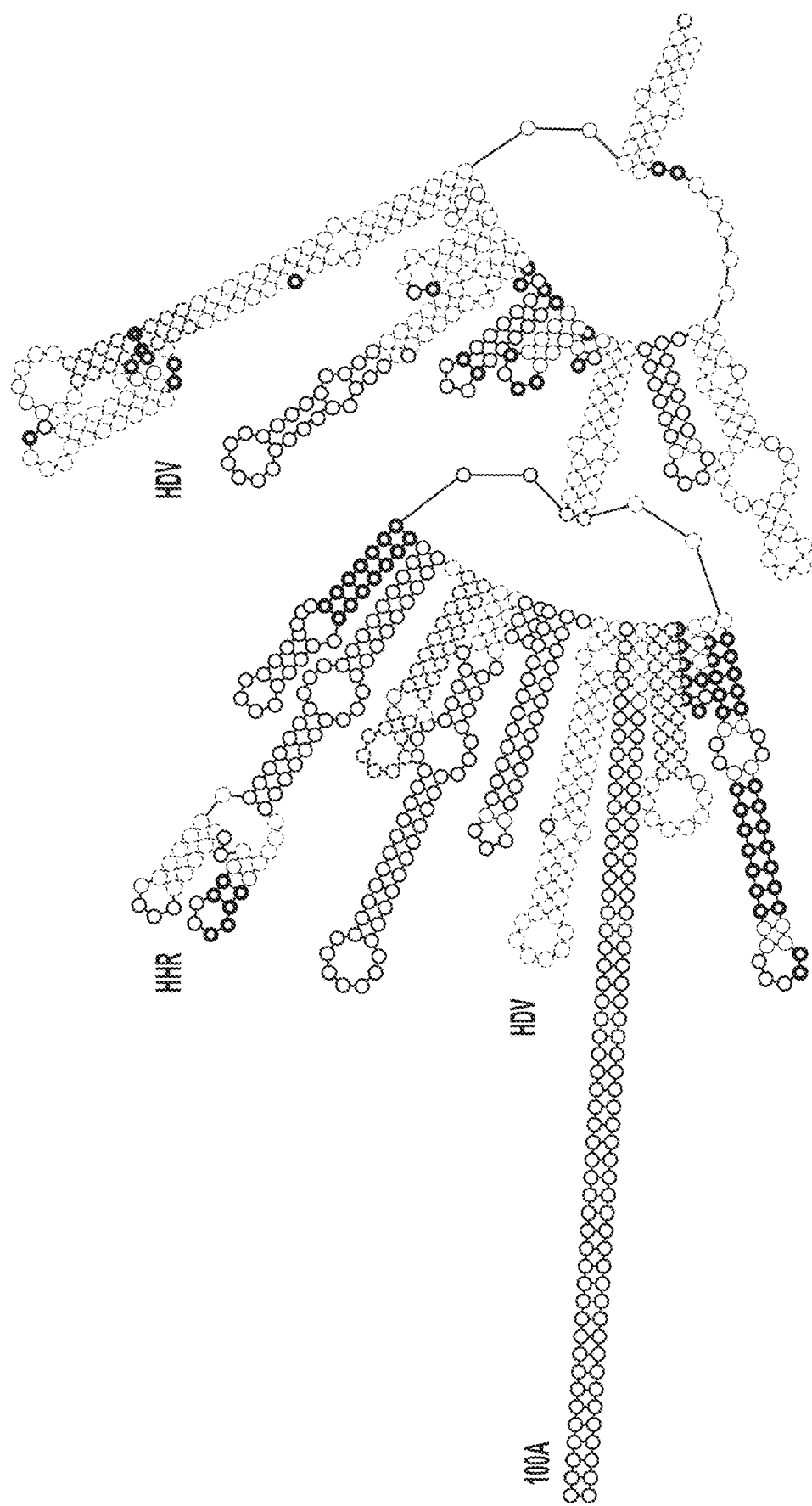
Figure 6C:
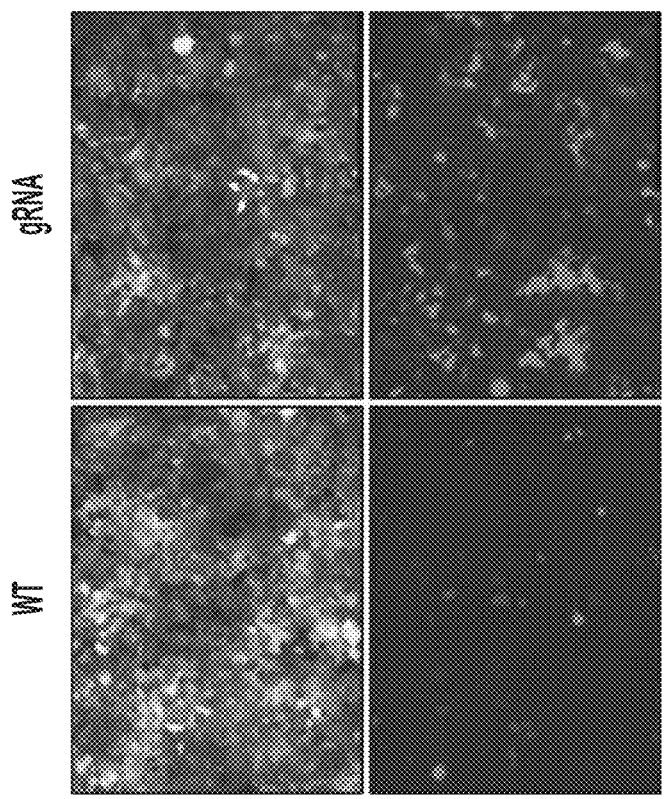
Figure 6D:
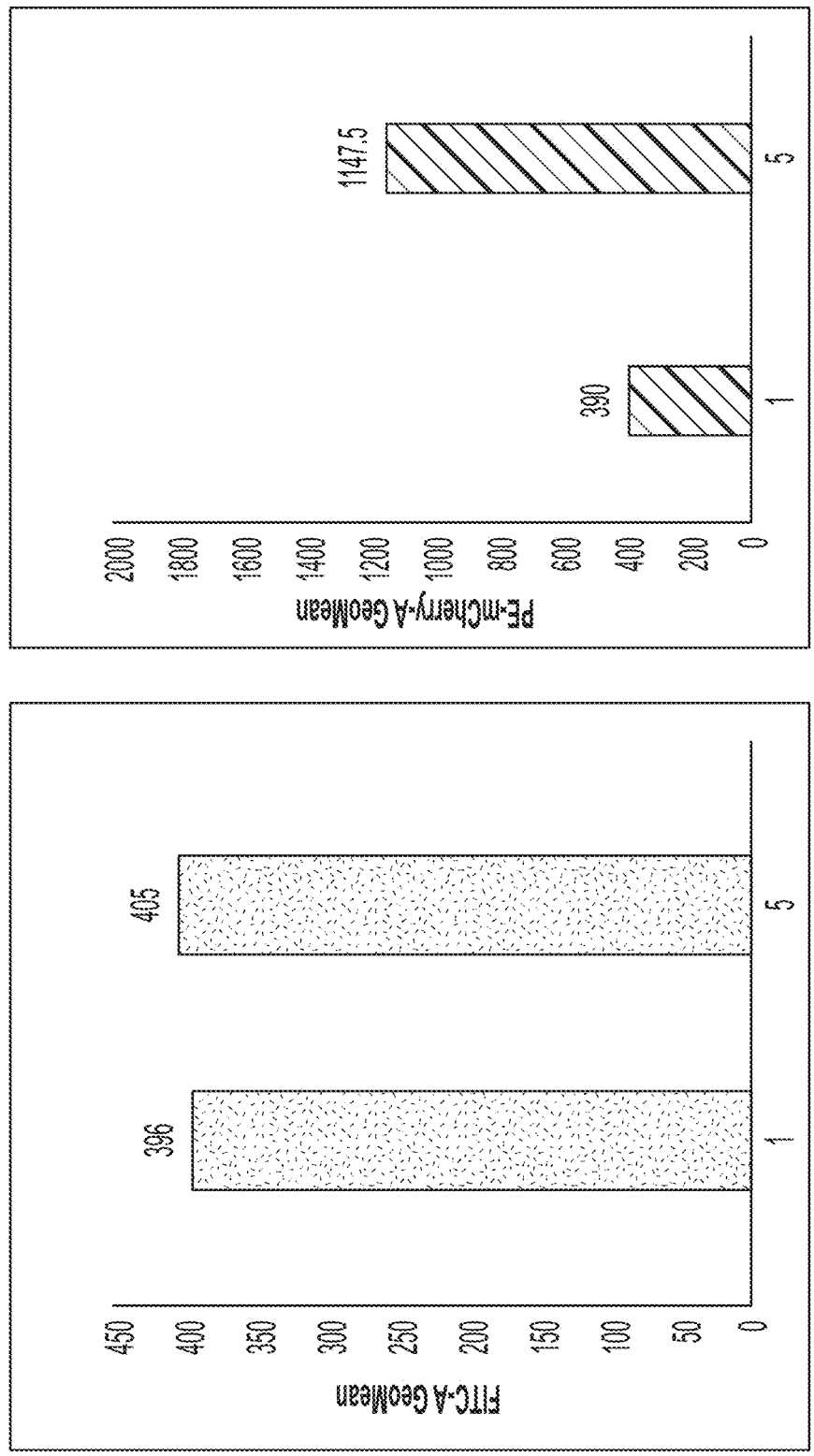

Example 4: Engineered gRNA Expression Cassette at the Terminator Region of an Endogenous Gene The non-coding RNA that can be expressed in the post-PAS RNA can be guide RNA and micro-RNA. FIG. 6A shows an exemplary design for a gRNA expression cassette. The construct includes, 5' to 3', a upstream gene (e.g., EYFP), a poly A signal (e.g., AAUAAA), a poly A tail, a wild type HDV ribozyme, a hammer head ribozyme_56 (HHR_56), an RNA for expressing a gRNA, and a HDV_84 ribozyme (HDV_84). FIG. 6B is a structural illustration of the exemplary gRNA expressing post-PAS RNA. Once transcribed, the mRNA for EYFP can be cleaved at the wide type HDV site, and further polyadenylation and expression of the mRNA can happen. The gRNA will be cleaved at the HHR_56 and HDV_84 sites and be processed to single copy gRNA. The successful expression and processing of the gRNA can be tested using a dCas9/transcription factor chimera protein (activator (TAD) or inhibitor (TID)). If the gRNA, is produced, it can guide dCas9/TAD or dCas9/TID to the target site for transcriptional activation or inhibition of a reporter gene (e.g., a tdTomato). Sequence upstream of the poly A trail stabilizes mRNA, should "match" the sequence of endogenous gene poly A signal. FIG. 6C shows that the gRNA is successfully produced from the construct to guided dCas9/VPR (VP64-p65-Rta activator) to activate tdTomato expression. FIG. 6D shows the quantification of fluorescence intensity of EYFP and tdTomato of FIG. 6C.

Figure 6E:
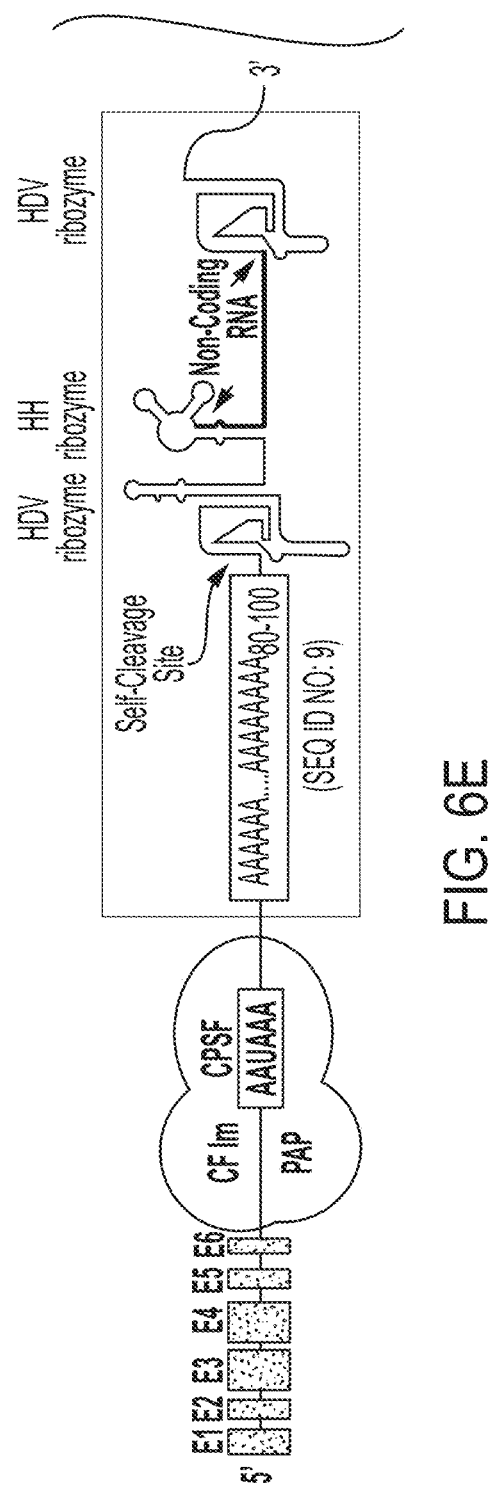
Figure 6E:
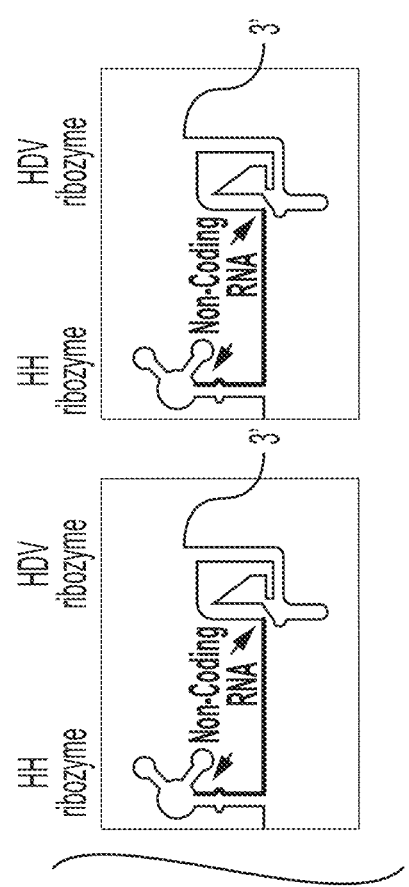
Figure 6F:
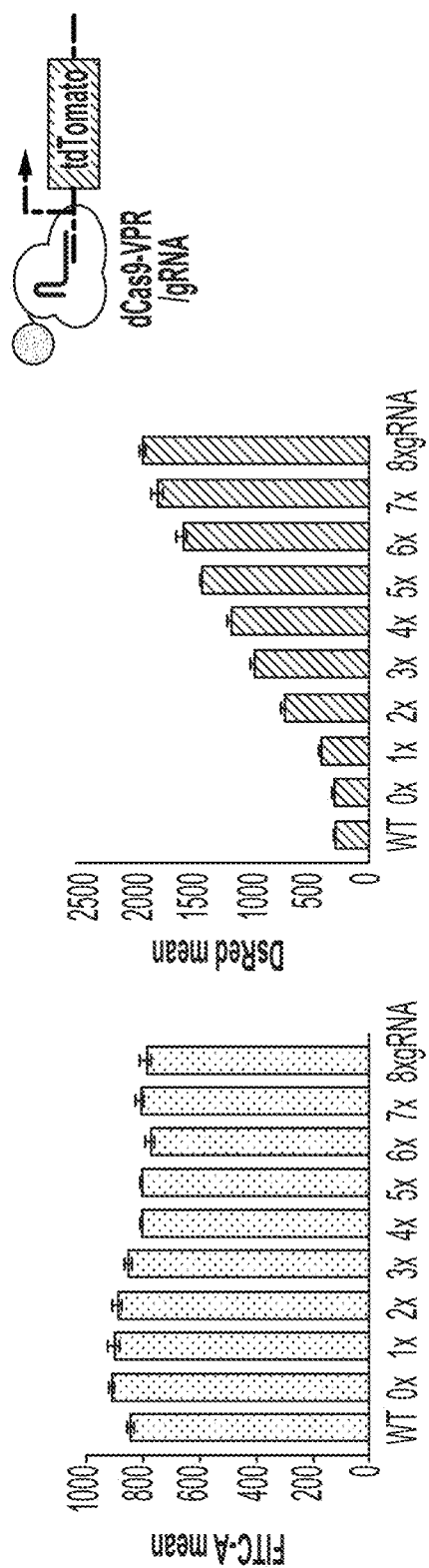

Also, whether multiple copies of gRNA can be produced from one post-PAS was tested. The construct as designed is shown in FIGS. 6E-6F, and it includes from 5' to 3': an upstream gene (e.g., EYFP), a poly A signal (e.g., AAUAAA), a poly A tail, a wild type HDV ribozyme, (a hammer head ribozyme_56 (HHR_56), an RNA for expressing a gRNA, and a HDV_84 ribozyme (HDV_84))$_n$. The construct can have multiple copies of the HHR_56-gRNA-HDV_84 cassette. Up to 8 cassettes were tested. FIG. 6G shows that expressing multiple gRNAs in one post-PAS RNA did not affect upstream gene expression, and including multiple gRNA cassettes in one constructs leads to more gRNA production, as evidenced by higher tdTornato expression.

Figure 9A:
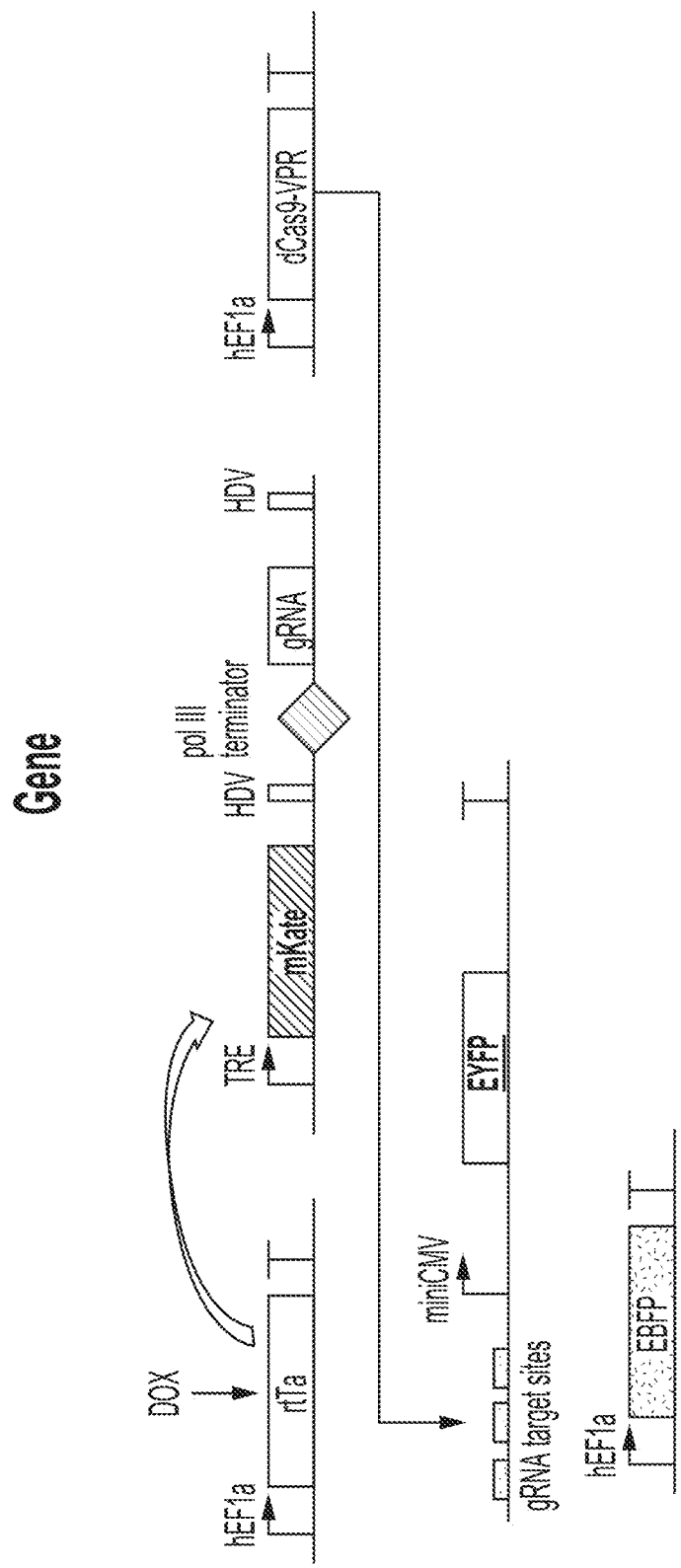
FIGS. 9A-9B show that a Pol III terminator placed between the HDV ribozyme and the gRNA cassette can prevent HDV driven expression of gRNA independent of the upstream gene.
Figure 9B:
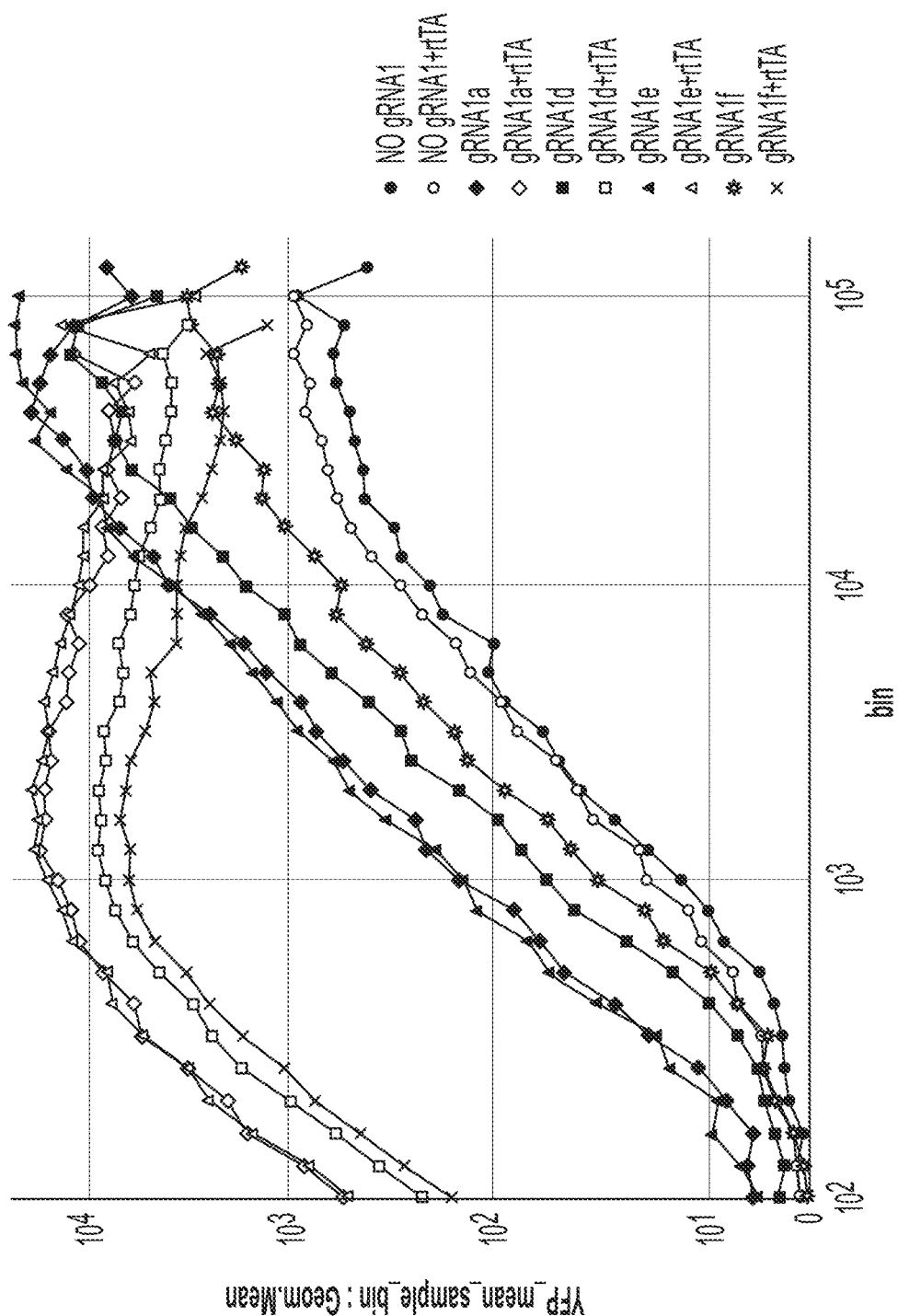

If the first RNA cleavage site in the construct is an HDV ribozyme, due to the Pol III promoter activity of HDV ribozyme, undesired expression of gRNA could happen without the expression of the upstream gene. In order to reduce such undesired effects, a Pol HI terminator can be placed between the HDV ribozyme and the gRNA expression cassette. Such placement is effective in preventing HDV ribozyme driving the expression of the gRNA independent of the upstream gene. To test whether the Pol III terminator was effective, an expression system was designed. gRNA expression cassette was placed in the terminator region of a mKate driven by a TRE promoter, and HDV ribozyme was placed 5' of the gRNA cassette as the first RNA cleavage site. A Pol III terminator was placed between the HDV and the gRNA, cassette. Only when Dox was added to the system, mKate can be expressed, which leads to the transcription of the post PAS gRNA expression cassette. Once the gRNA is expressed, it can guide dCas9-VPR to an EYFP expression construct having gRNA target site adjacent to the miniCMV promoter, which drives the expression of EYFP (FIG. 9A). Indeed, for the four different gRNA tested, EYFP expression in the presence of Dox was much higher than EYFP expression in the absence of Dox, confirming that the Pol III terminator is capable of preventing HDV ribozyme driving the expression of gRNAs independent of the upstream gene expression (FIG. 9B).

Figure 7A:
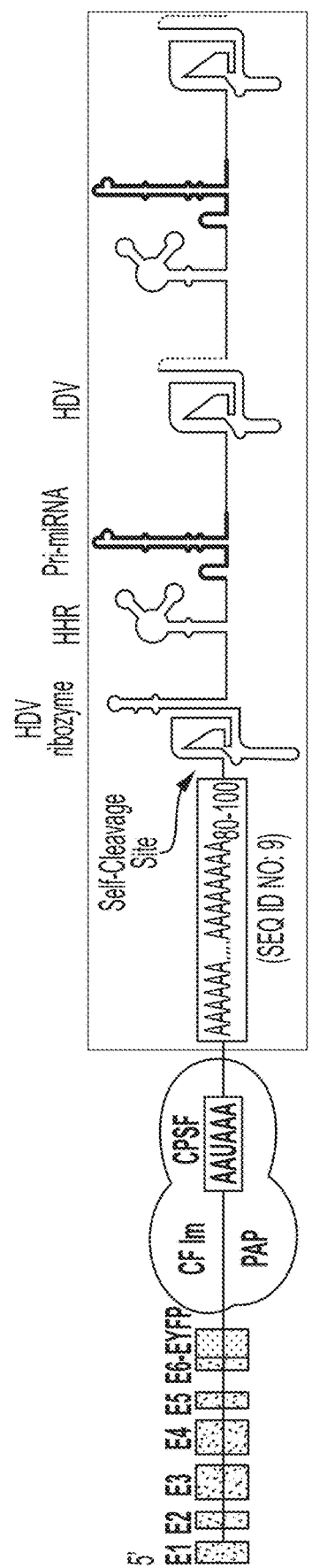
FIGS. 7A-7F are figures showing generation of miRNA using post-PAS RNA.
Figure 7B:
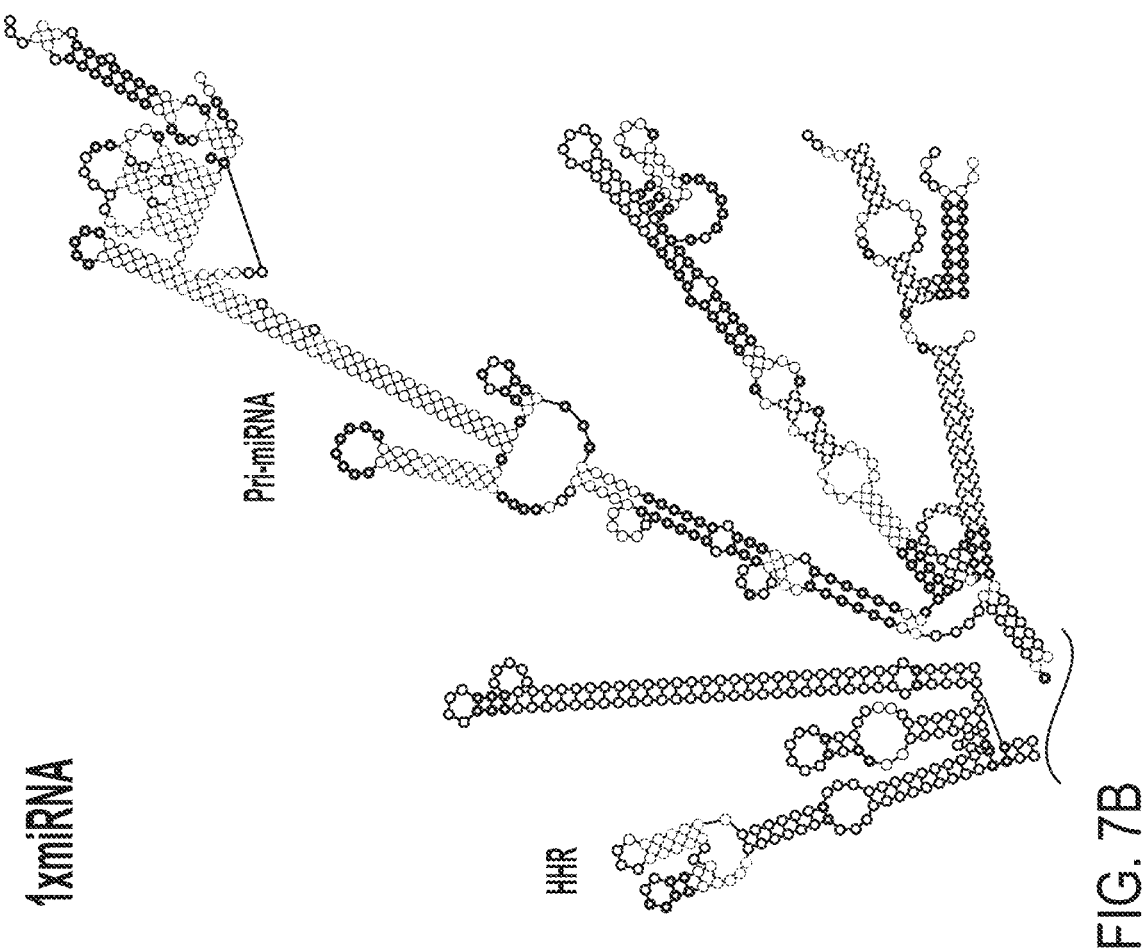
Figure 7B:
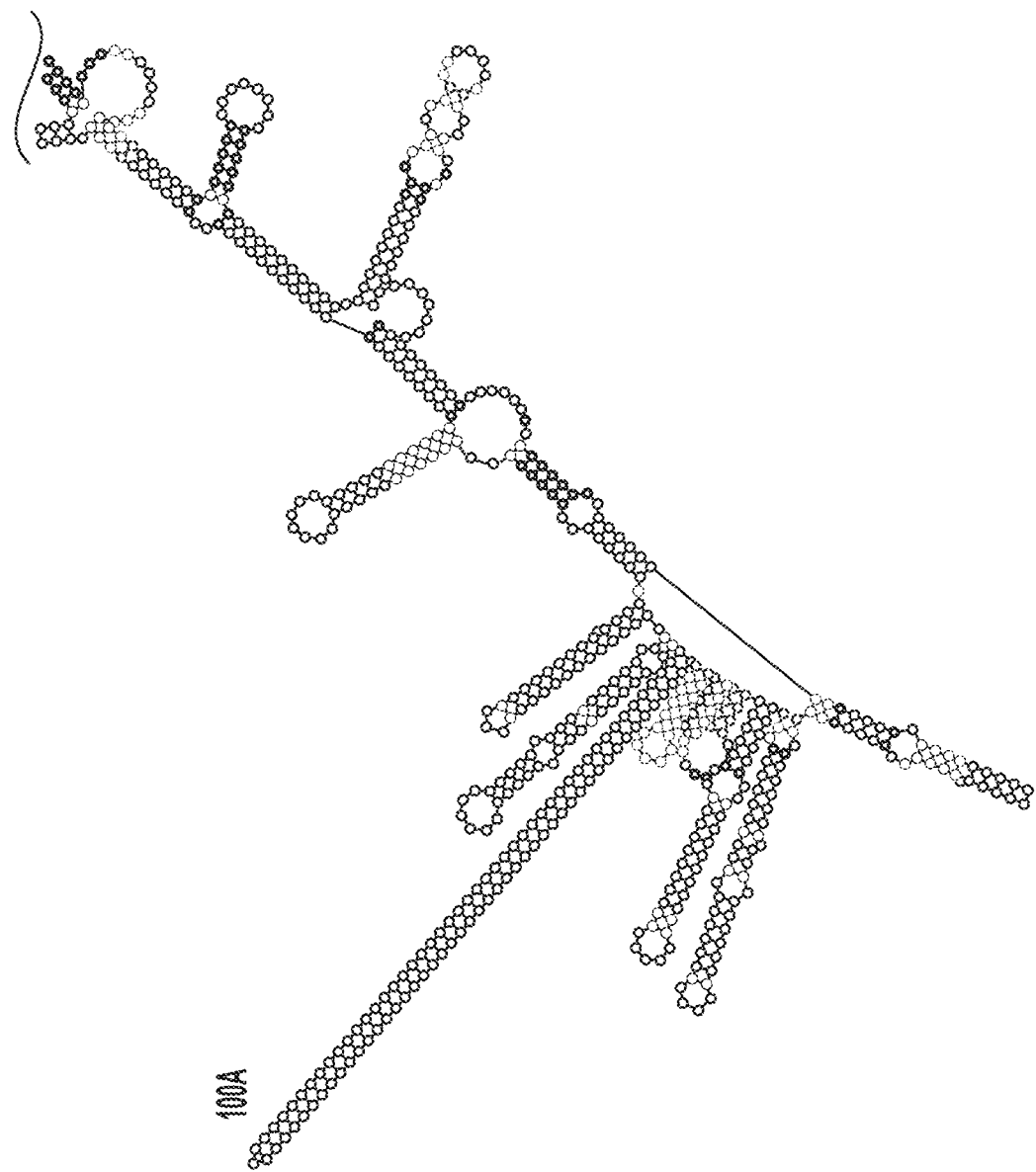
Figure 7B:
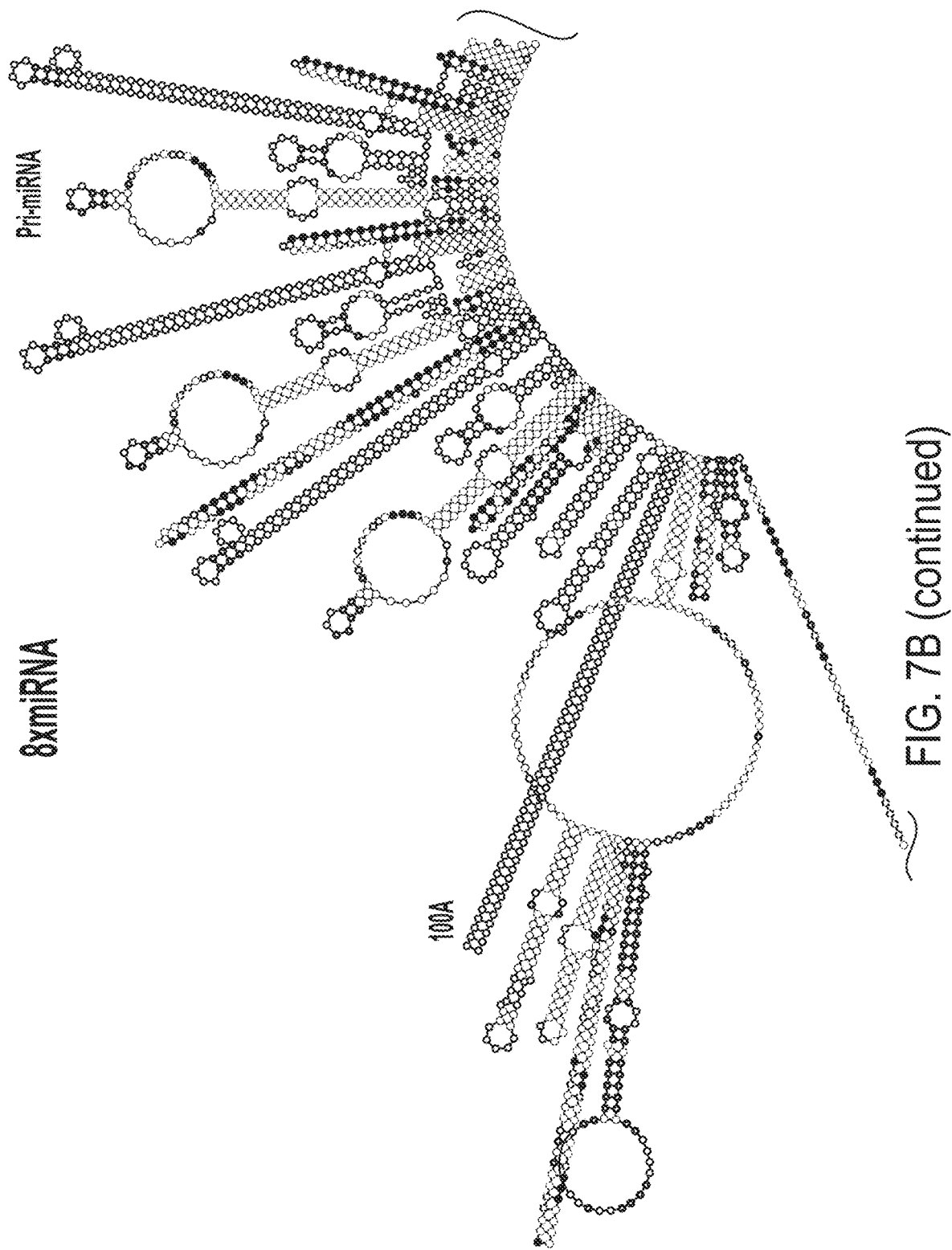
Figure 7B:
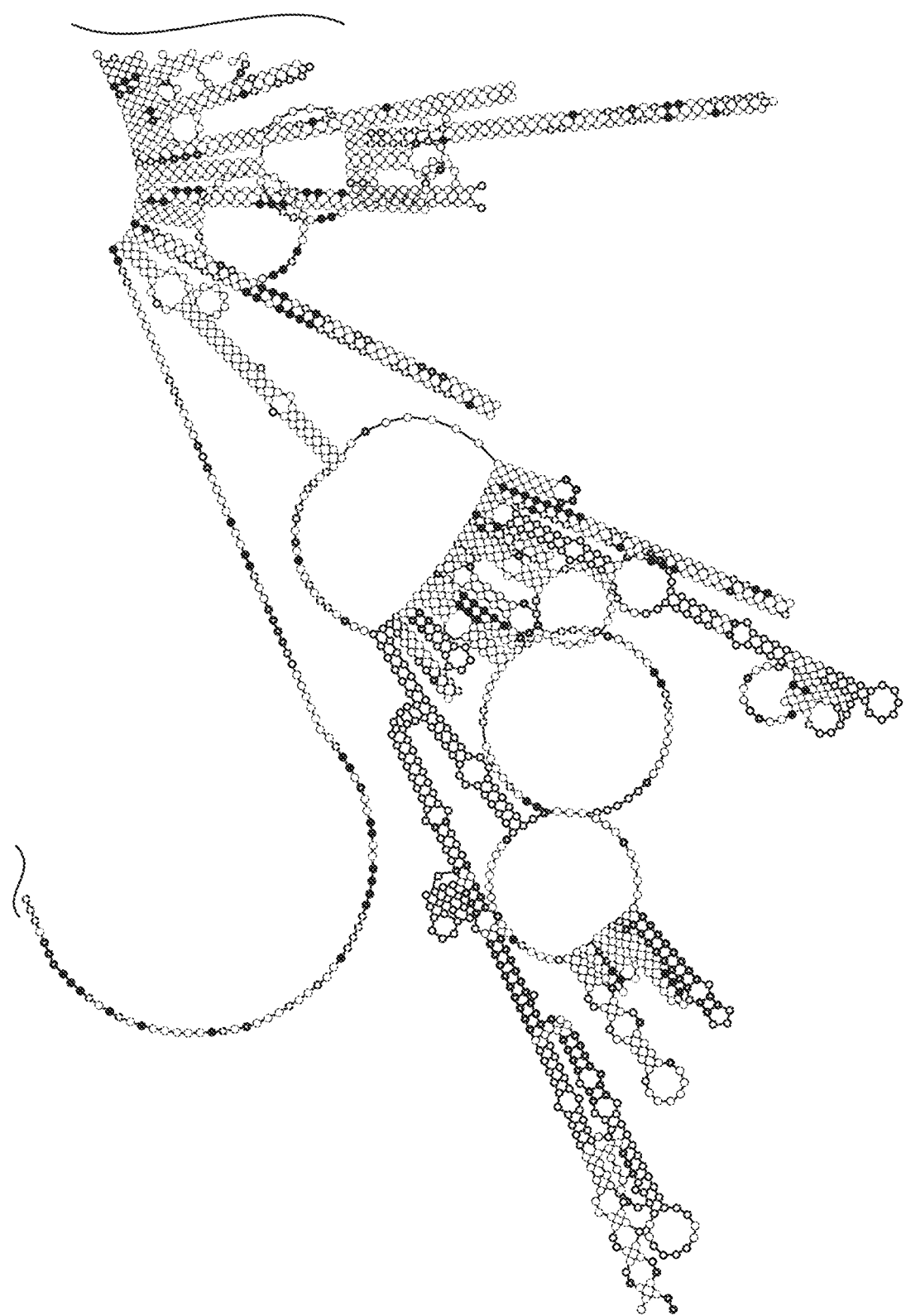
Figure 7B:
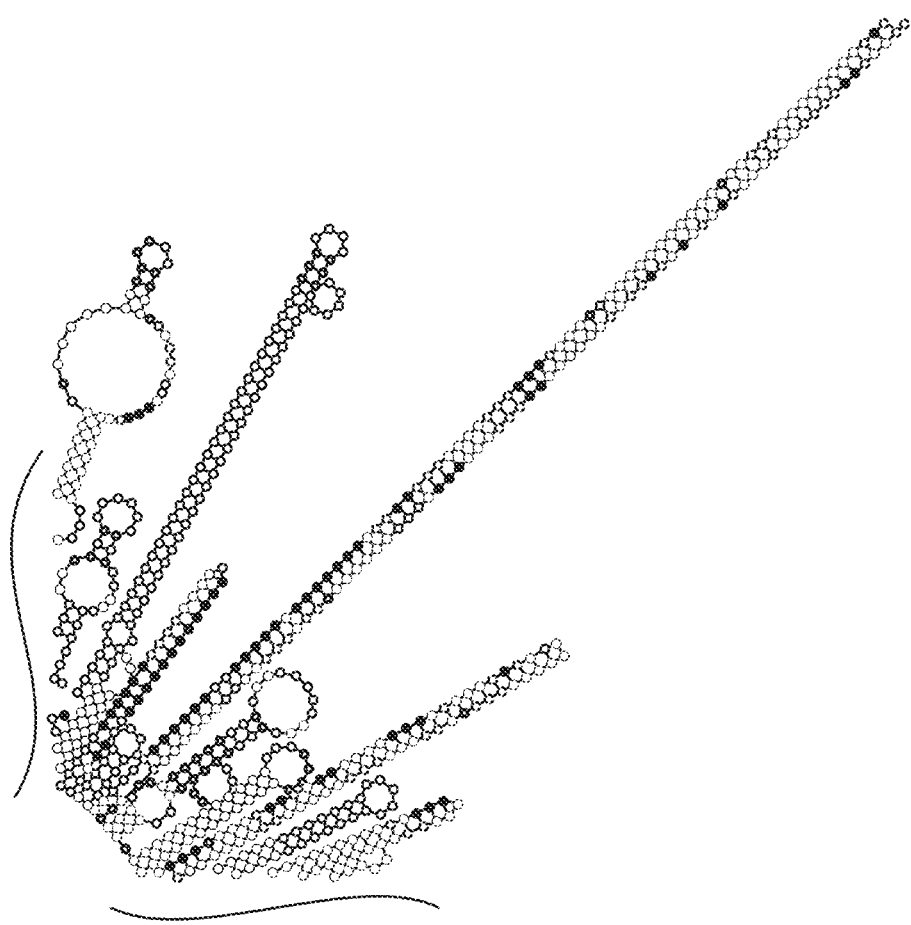
Figure 7C:
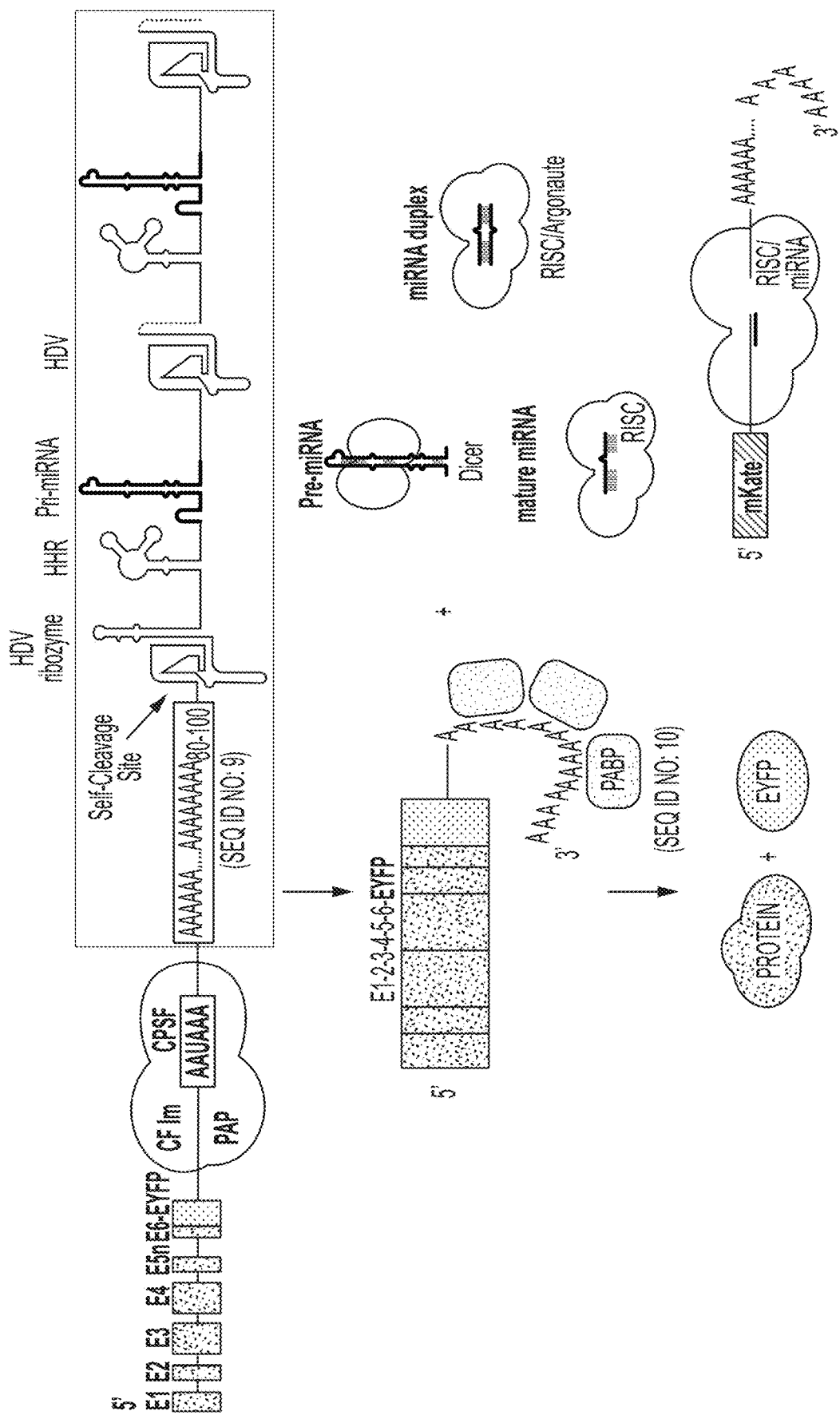
Figure 7D:
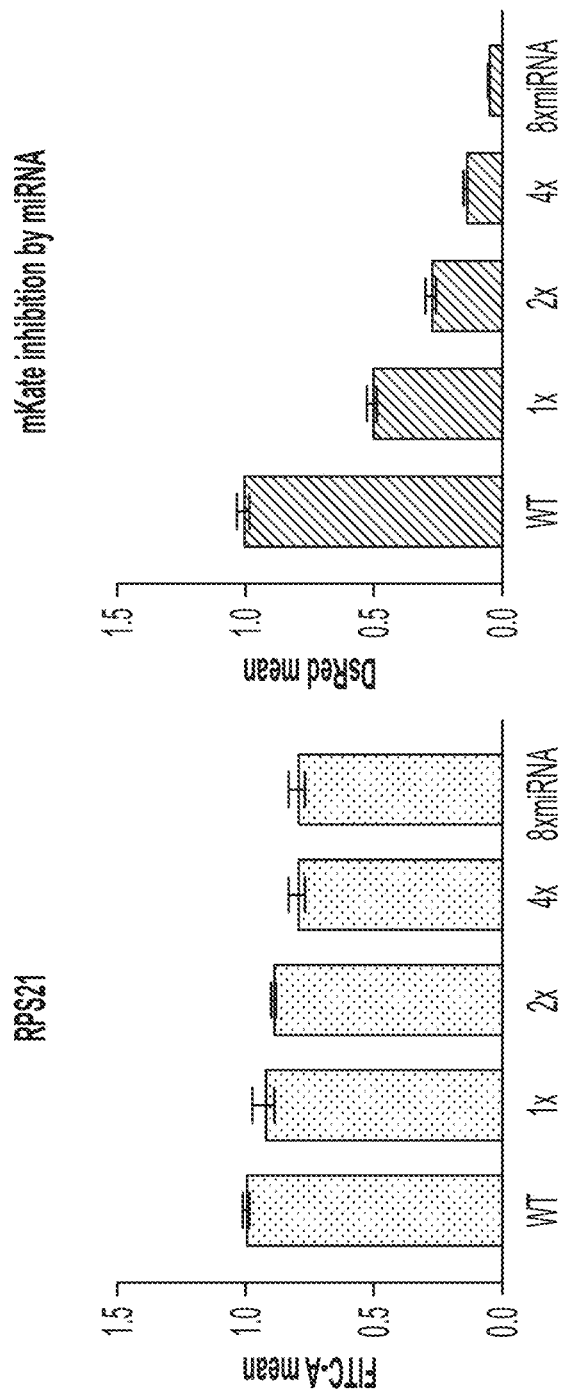
Figure 7E:
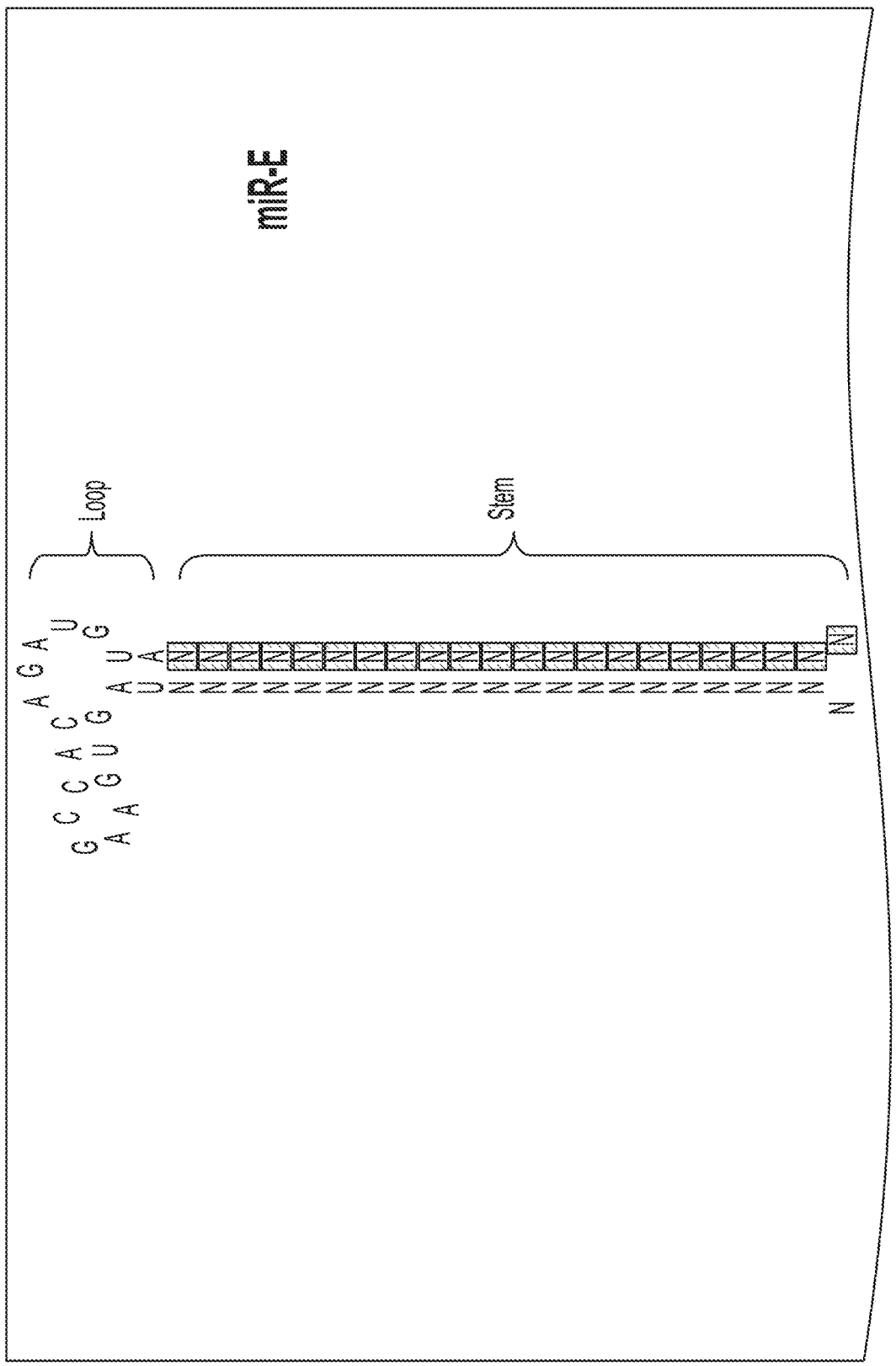
Figure 7E:
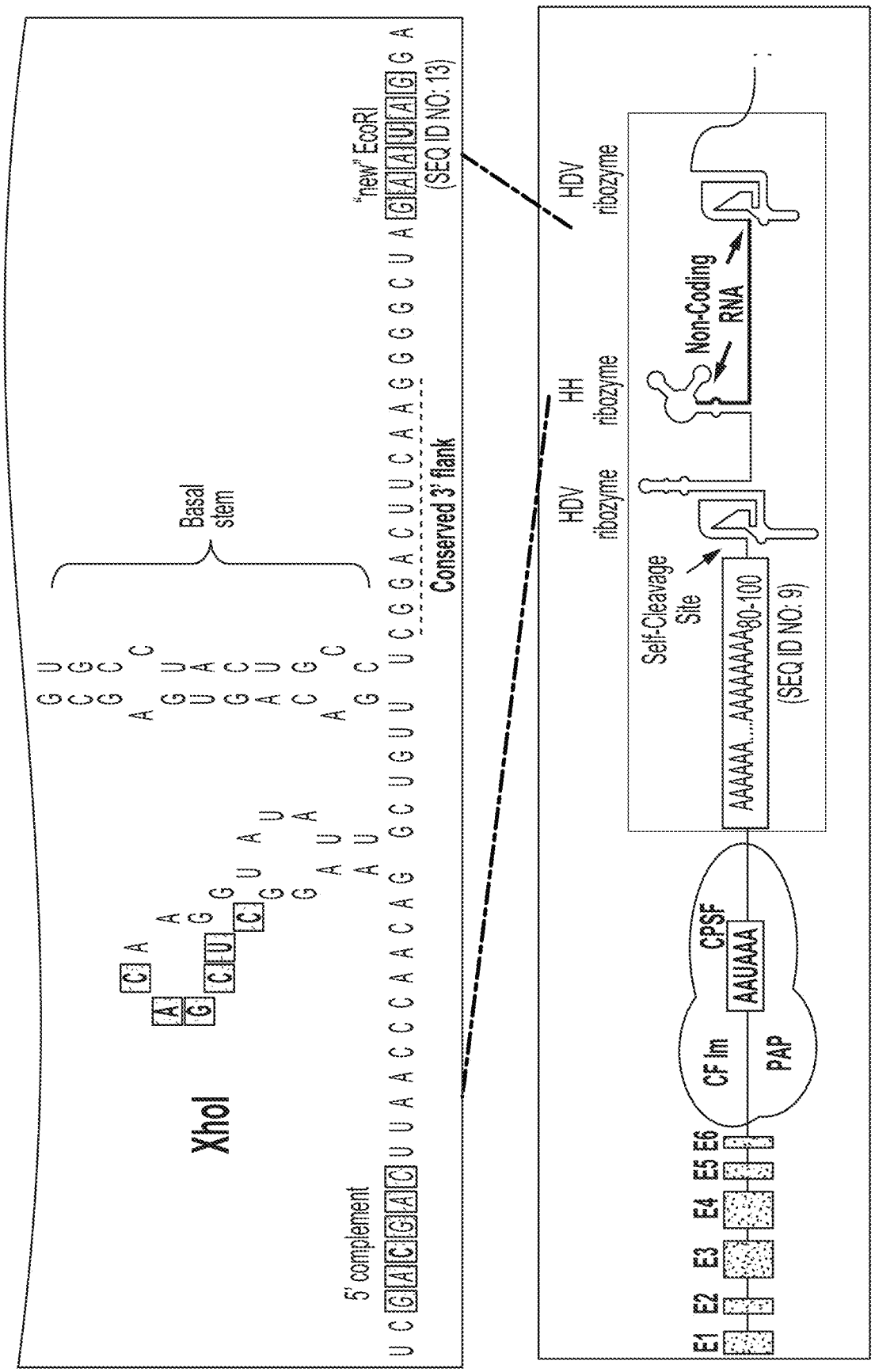
Figure 7F:
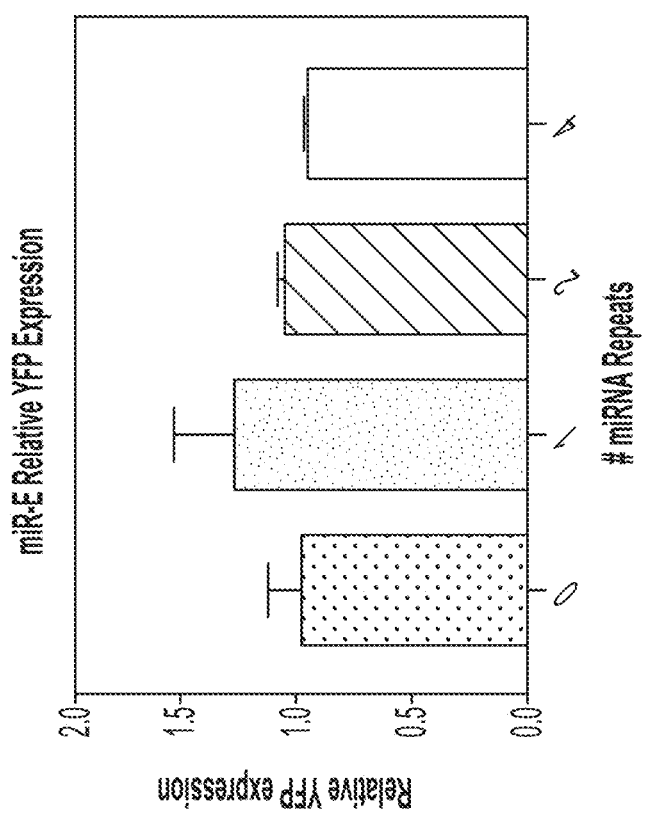

Example 5: Engineered miRNA Expression Cassette at the Terminator Region of an Endogenous Gene The expression of microRNA from the post-PAS RNA was also tested. FIG. 7A shows an exemplary design for a miRNA expression cassette. The construct includes, 5' to 3', a upstream gene (e.g., EYFP), a poly A signal (e.g., NAUAAA), a poly A tail, a wild type HDV ribozyme, a hammer head ribozyme_56 (HHR_56), primary miR-FF4 (pri-miR-FF4), and a HDV_84 ribozyme (HDV_84). FIGS. 7B-7G are a structural illustration of the exemplary miRNA expressing post-PAS RNA in single copy or multiple copies. Once transcribed, the mRNA for EYFP can be cleaved at the wide type HDV site, and further polyadenylation and expression of the mRNA can happen. The miRNA will be cleaved at the HHR_56 and HDV_84 sites and be processed to mature miRNA. The successful expression and processing of the miR-FF4 can be tested using an mKate expression construct having miR-FF4 targeting site at the 3'UTR of mKate gene. FIG. 7H is a schematic illustration of the above described process. FIG. 7I shows that the miRNA is successfully produced from the construct to inhibit mKate expression without affecting upstream EYFP expression. Also, whether multiple copies of gRNA can be produced from one post-PAS RNA was tested. FIG. 7I shows that expressing multiple miRNAs in one post-PAS RNA did not affect upstream gene expression, and including multiple miRNA cassettes in one constructs leads to more miRNA production, as evidenced by stronger mKate inhibition.

In addition, an conserved backbone element, called miR-E was identified to be important for effective production of single-copy miRNA (Christof et al., *Cell Rep.* 2013 Dec. 26;5(6):1704-13). Therefore, a miR-E element can be incorporated to the 3' of the pri-miR sequence in each miRNA cassette (FIGS. 7J-7K). FIG. 7L shows stable YFP expression (representative of constitutive gene expression) with up to four repeats of downstream miRNA expression.

Example 6: Exemplary Functions of Post-PAS RNA Expressing ncRNA

Figure 8A:
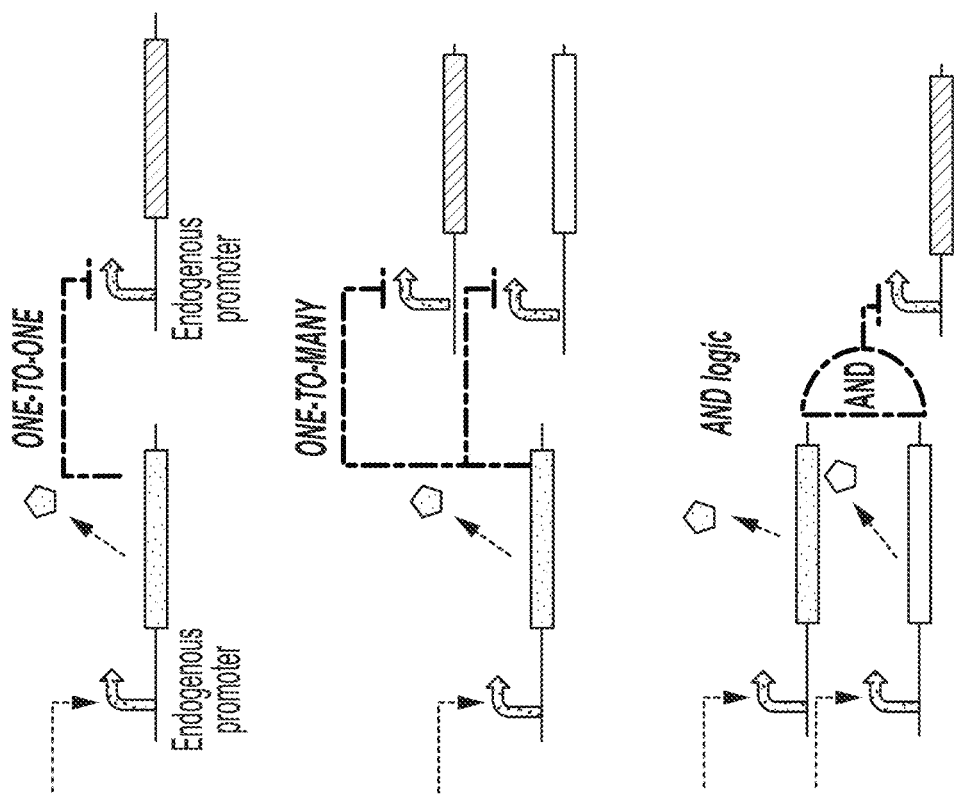
FIG. 8A-8G are figures showing the possible regulatory network the post-PAS RNA encoding gRNA can offer.

In some cases, the engineered post-PAS RNA can be used to rewire endogenous gene applications, including at least one-to-one rewiring of endogenous gene activation, one-to-one rewiring of endogenous gene inhibition, similar one-to-many rewirings, and logic such as "AND" logic rewiring (FIG. 8A).

Figure 8B:
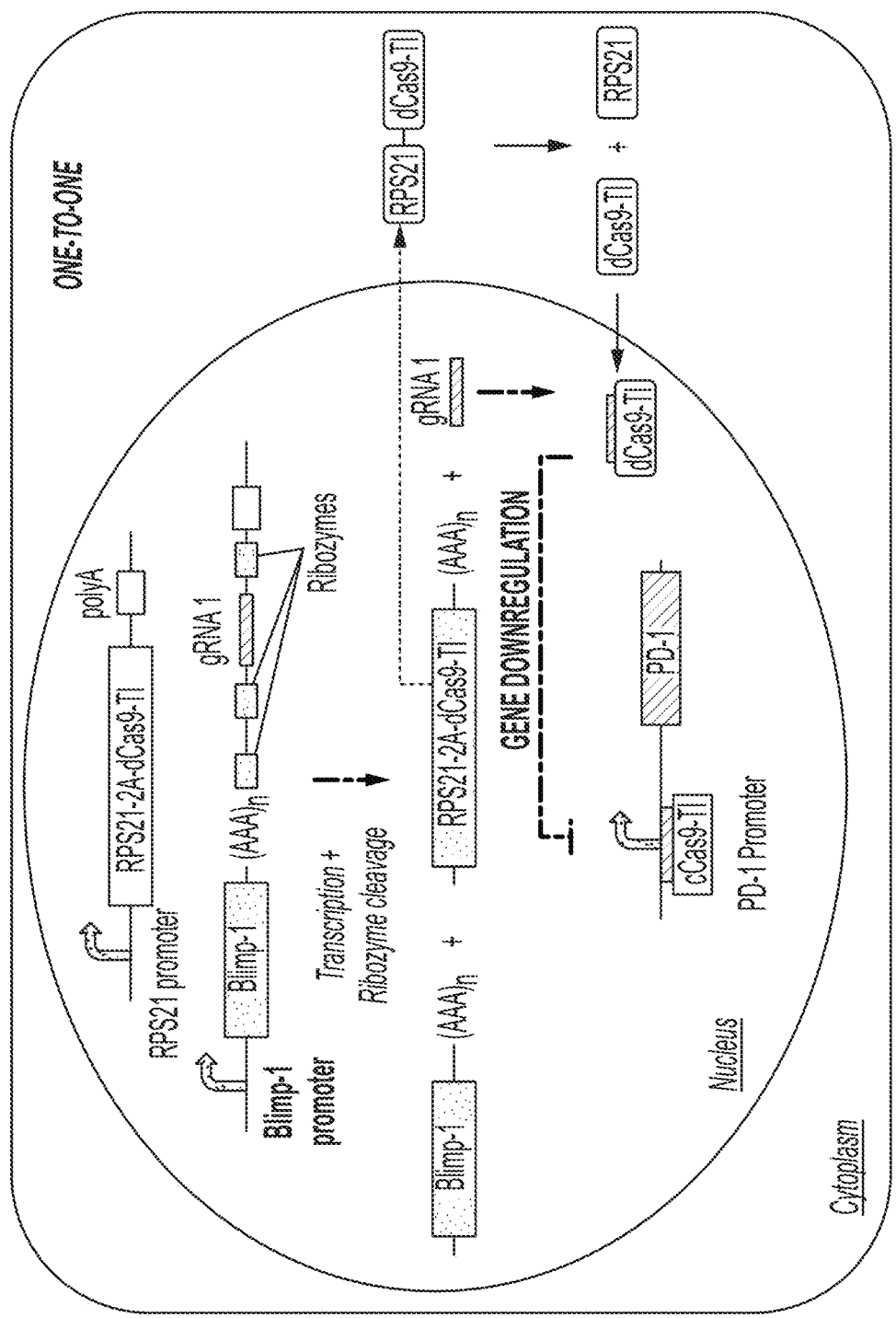
Figure 8C:
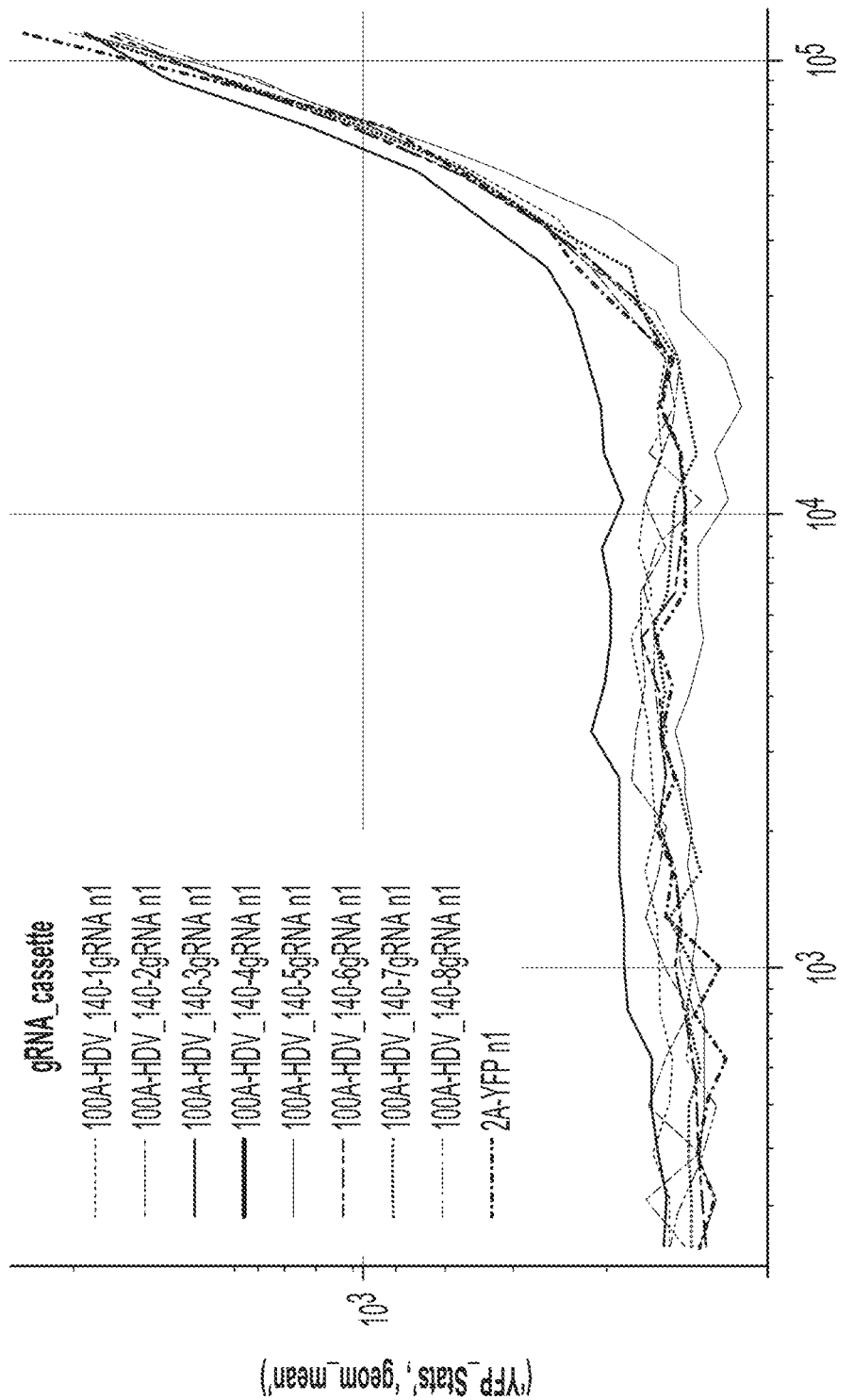
Figure 8D:
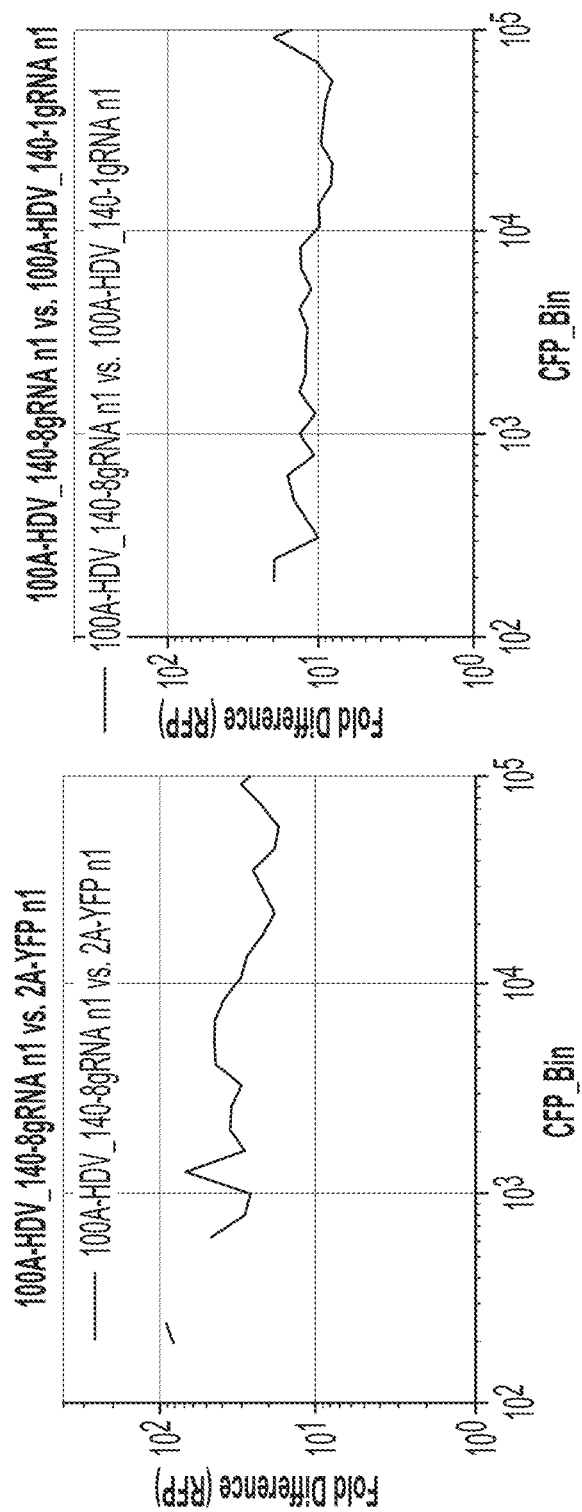
Figure 8E:
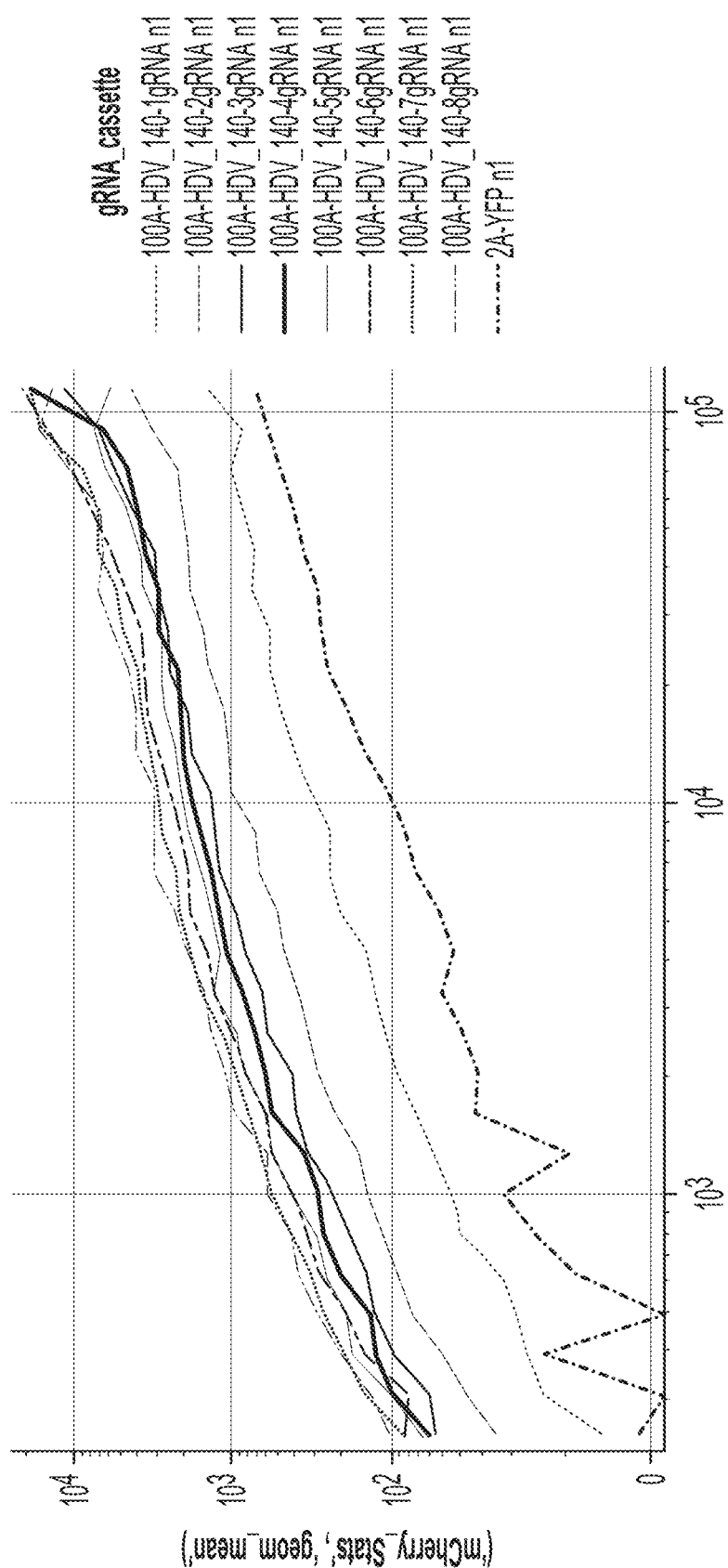

"One-to-one" regulation essentially creates a new direct regulatory link that allows rewiring of cellular event, detected by endogenous promoter activation, to activation or inhibition of a customized response (FIG. 8B). Here, dCas9-TID or dCas-TAD is expressed constitutively from a housekeeping gene via fusion of 2A self-cleaving peptide sequence. A gRNA that specifies which target endogenous promoter to activate is inserted downstream of an endogenous "sensor" gene. is important that the chromosomal integrations of dCas9-TAD and the gRNA do not alter the wild-type expression levels of the modified genes. FIG. 8C and FIG. 8D indicate that 2A fusion of an exogenous gene (e.g., in our case dCas9-TA or dCas9-TI) with a housekeeping gene does not alter wild-type expression levels. Due to the transcript processing requirements, insertion of gRNA requires a more sophisticated approach than insertion of dCAS9 genes. The mRNA of the activated gene was engineered to possess self-cleavage activity that leads to creation of two separate transcripts, one for the endogenous gene and one for the synthetic gRNA. By introducing several synthetic elements that rescue the potential defects of 3' polyA processing, the self-cleaved endogenous gene mRNA will maintain the properties of wild-type transcripts, including nuclear export and translational ability. In terms of customizing the dosage response curve, regulation of the activation level of a gene of interest via the number of sgRNA expressed was shown in FIG. 8E, such that multiple co-expressed sgRNAs produce a corresponding increase in inhibition or activation strength.

Figure 8F:
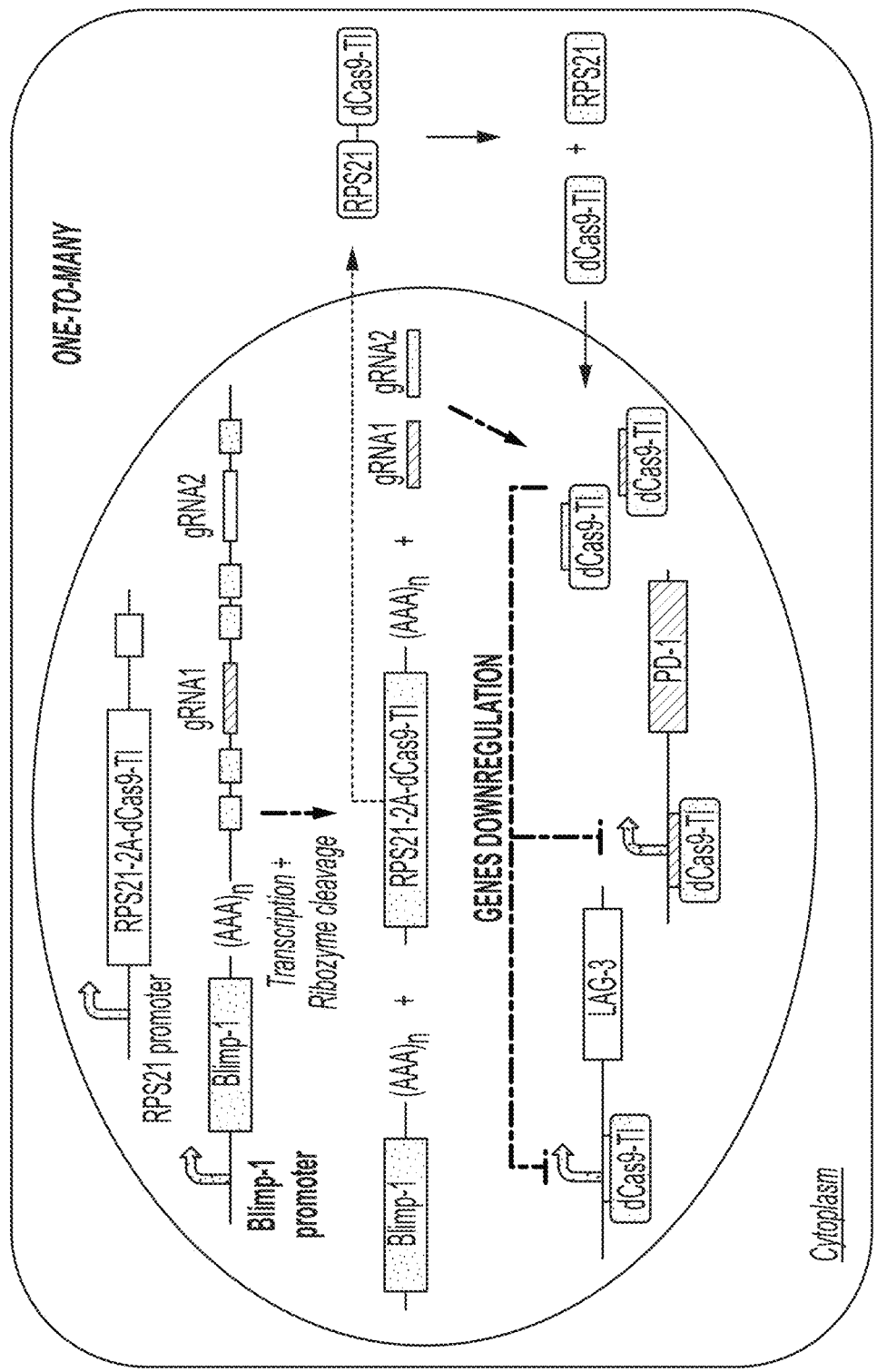

"One-to-many" inhibition means a single endogenous gene transcript generates different gRNAs, thereby inhibiting multiple endogenous genes. In one-to-many rewiring, simultaneous inhibition or activation of different genes can be done by simply by encoding different gRNAs. (FIG. 8F)

Figure 8G:
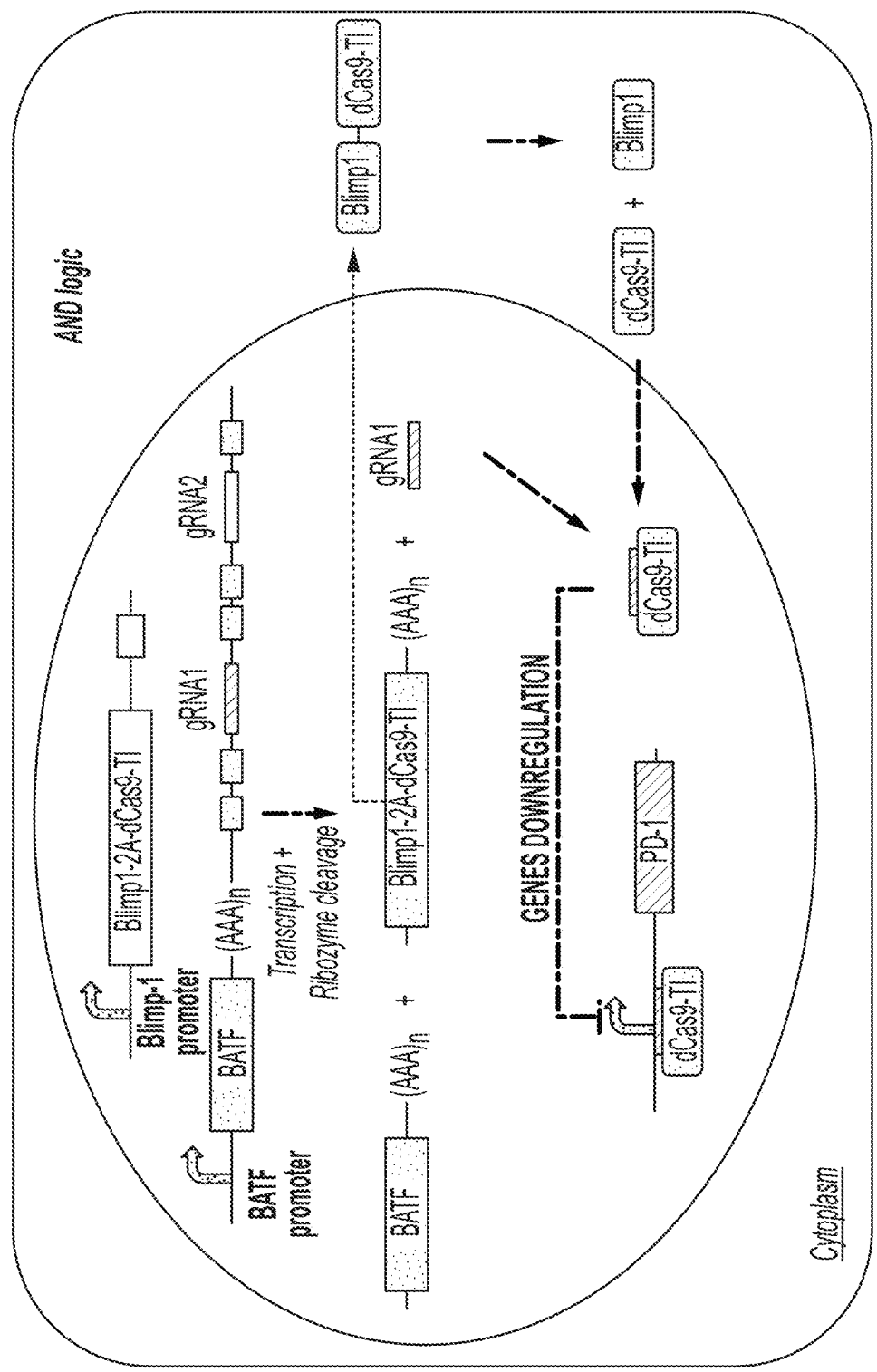

"AND logic" inhibition means Simultaneously expressed endogenous gene transcripts generate dCas9-TI and gRNA, inhibiting an endogenous promoter of interest only when both input conditions are true. In a 2-input AND logic rewiring, two cellular events must occur simultaneously to inhibit or activate an endogenous gene of interest. This is achieved by integration of sgRNA into the first endogenous "sensor" gene as above, and 2A fusion of dCas9-TI or dCas9-TA to a second endogenous "sensor" gene (instead of the housekeeping gene). In the AND logic configuration, activation of the target gene requires that both endogenous sensor genes are simultaneously expressing (FIG. 8G).

The above described cellular rewiring approach is flexible and extensible, allowing sophisticated logic circuits to be implemented, including multi-input AND gates, OR gates, and NOT gates.

Example 7: Generation of a Pancreatic Organoids Using the Post PAS RNA

Figure 10A:
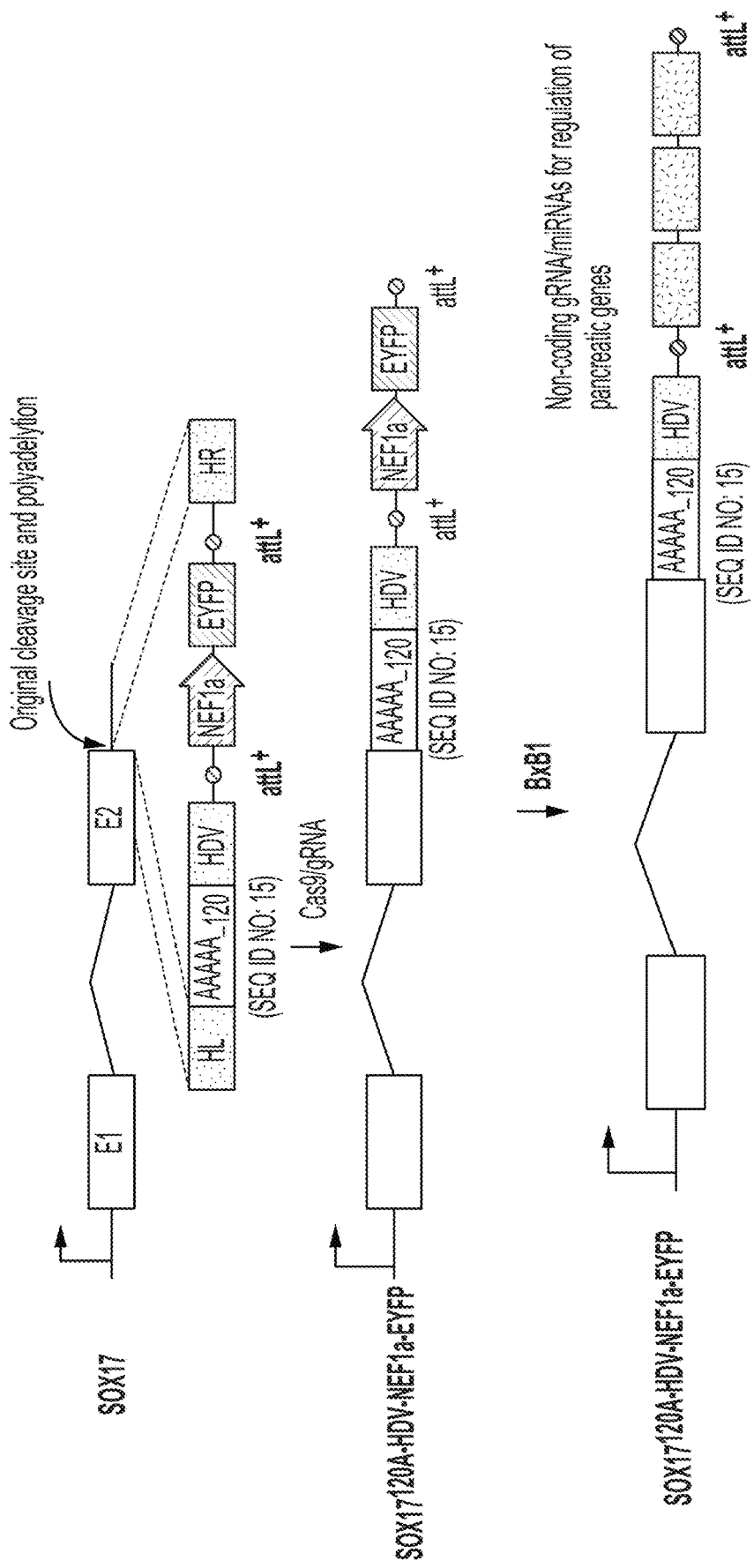
FIGS. 10A-10B show how the post PAS RNA can be used to direct stem cell differentiation.
Figure 10B:
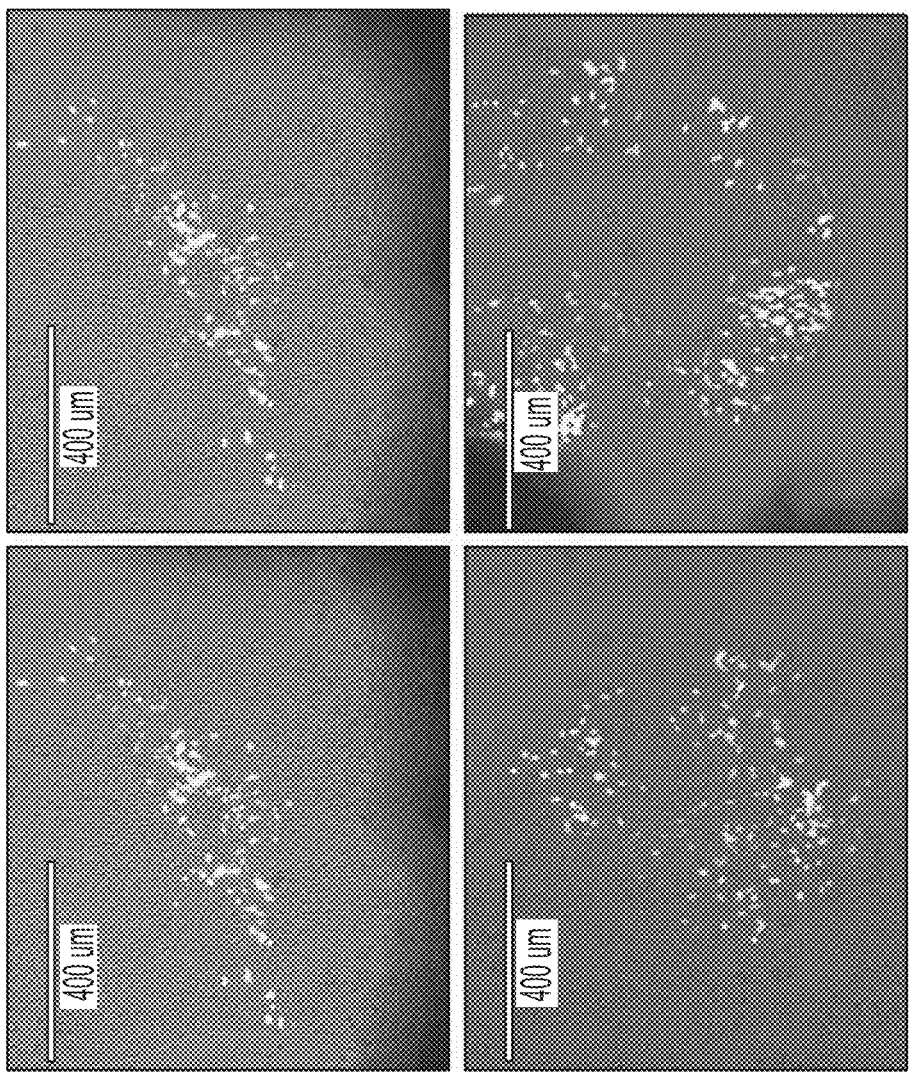

A nucleotide sequence encoding a post PAS RNA with a gRNA expression cassette for a gRNA targeting a pancreas specific gene was placed at the terminator region of an endogenous Sox17 gene in a stem cell. The stem cells were transfected with a Gata6 expression construct driven by a pTREt promoter, which can be activated in the presence of Dox. When Dox is present, the cells that express high to medium level of Dox differentiate into mesoendoderm. Mesoendoderm cells further differentiate into endoderm and mesoderm. The endoderm cells express Sox17 gene, thereby activating the expression of the Post PAS RNA. Integration of the post PAS RNA encoding the gRNA was achieved in two steps. First, a post PAS RNA encoding an EYFP was placed in the Sox17 terminator, and dCas9-transcription factor/gRNA targeting the EYFP promoter were given to the cell. The endoderm cells with successful integration of the post PAS RNA encoding the EYFP were positive for EYFP (FIG. 10B). Second, the post PAS encoding the EYFP in EYFP positive endoderm cells were replaced with a post PAS RNA encoding gRNAs targeting a pancreas specific gene. Once the gRNA was expressed, it guided the dCas9-transcription factor to activate the expression of a pancreas specific gene Pdx1, thereby driving the differentiation of the organoid to a pancreatic organoid (FIG. 10A). The mesoderm cells differentiated into blood vessels. The differentiation of the endoderm cells and the mesoderm cells resulted in a vascularized pancreatic organoid.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the, claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An engineered nucleic acid comprising, from 5' to 3':
   (1) a terminator, wherein the terminator comprises a nucleotide sequence encoding a poly A signal, and
   (2) a nucleotide sequence encoding a post-poly A signal (post-PAS) RNA,
   wherein the nucleotide sequence encoding the post-PAS RNA comprises a protein-coding cassette, wherein the protein-coding cassette from 5' to 3' comprises: a nucleotide sequence encoding a first RNA cleavage site, a nucleotide sequence encoding a 5' cap, a nucleotide sequence encoding an internal ribosome entry site (IRES), a nucleotide sequence encoding the protein, a nucleotide sequence encoding a 3' cap, and a nucleotide sequence encoding a second RNA cleavage site; or
   wherein the nucleotide sequence encoding the post-PAS RNA comprises a non-coding RNA cassette,
   (i) wherein the non-coding RNA cassette is a miRNA cassette that comprises from 5' to 3': a nucleotide sequence encoding a first RNA cleavage site, a nucleotide sequence encoding a primary micro-miRNA (pri-miRNA), and a nucleotide sequence encoding a second RNA cleavage site; or
   (ii) wherein the non-coding RNA cassette is a guide RNA (gRNA) cassette that comprises from 5' to 3': a nucleotide sequence encoding a first RNA cleavage site, a nucleotide sequence encoding a gRNA, and a nucleotide sequence encoding a second RNA cleavage site.

2. The engineered nucleic acid of claim 1, wherein the poly A signal comprises a nucleotide sequence of AAUAAA.

3. The engineered nucleic acid of claim 1, wherein the terminator further comprises a poly A tail or a synthetic poly A mimic 3' to the poly A signal.

4. The engineered nucleic acid of claim 3, wherein the terminator comprises a nucleotide sequence encoding a RNA cleavage site between the poly A signal and the poly A tail or the synthetic poly A mimic, wherein the RNA cleavage site is capable of being cleaved by Cleavage and polyadenylation specificity factor (CPSF).

5. The engineered nucleic acid of claim 4, wherein a nucleotide sequence $(N)_X$ is present between the poly A signal and the poly A tail or the synthetic poly A mimic, wherein N can be any nucleotide, and X is between 10 and 40, optionally wherein X is 25.

6. The engineered nucleic acid of claim 1, wherein the nucleotide sequence encoding the post-PAS RNA comprises 1-10 protein-coding cassettes.

7. The engineered nucleic acid of claim 1, wherein the nucleotide sequence encoding the post-PAS RNA comprises 1-10 miRNA cassettes.

8. The engineered nucleic acid of claim 1, wherein the pri-miRNA further includes a miR-E element at the 3' end of the pri-miRNA.

9. The engineered nucleic acid of claim 1, wherein the nucleotide sequence encoding the post-PAS RNA comprises 1-10 gRNA cassettes.

10. The engineered nucleic acid of claim 1, wherein the first and second RNA cleavage sites are nuclease sites.

11. The engineered nucleic acid of claim 1, further comprising a promoter operably linked to a nucleic acid sequence encoding a transgene 5' to the terminator.

12. A vector comprising the engineered nucleic acid of claim 1.

13. An isolated cell comprising the engineered nucleic acid of claim 1.

14. The engineered nucleic acid of claim 1, wherein the first and second RNA cleavage sites are self-cleavage sites.

15. The engineered nucleic acid of claim 14, wherein the self-cleavage sites are small self-cleaving ribozymes.

16. The engineered nucleic acid of claim 14, wherein the small self-cleaving ribozymes, are selected from a hammerhead ribozyme, a hairpin ribozyme, a hepatitis delta virus (HDV) ribozyme, a Varkud satellite (VS) ribozyme, and a glmS ribozyme.

17. The engineered nucleic acid of claim 1, wherein the first self-cleavage sites and the second self-cleavage sites are different self-cleavage sites.

\* \* \* \* \*